(12) United States Patent
Liu et al.

(10) Patent No.: US 11,613,784 B2
(45) Date of Patent: Mar. 28, 2023

(54) NEXT-GENERATION BIOMARKERS TO DETECT SUN DAMAGE AND PREDICT SKIN CANCER RISK

(71) Applicant: The Trustees of Columbia University in the City of New York, New York, NY (US)

(72) Inventors: Liang Liu, Flushing, NY (US); Yao Shen, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1051 days.

(21) Appl. No.: 16/072,825

(22) PCT Filed: Mar. 16, 2017

(86) PCT No.: PCT/US2017/022848
§ 371 (c)(1),
(2) Date: Jul. 25, 2018

(87) PCT Pub. No.: WO2017/165199
PCT Pub. Date: Sep. 28, 2017

(65) Prior Publication Data
US 2021/0054462 A1 Feb. 25, 2021

Related U.S. Application Data

(60) Provisional application No. 62/458,535, filed on Feb. 13, 2017, provisional application No. 62/313,425, filed on Mar. 25, 2016.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,888,044 B2 | 2/2011 | Spanjaard |
| 8,299,216 B2 | 10/2012 | Alani et al. |
| 9,493,840 B2 | 11/2016 | Hao et al. |
| 2009/0226905 A1* | 9/2009 | Joubert ............ G01N 33/57419 435/7.1 |
| 2013/0072572 A1* | 3/2013 | Papazoglou ............ A61K 31/05 514/731 |
| 2014/0045915 A1 | 2/2014 | Skog et al. |

FOREIGN PATENT DOCUMENTS

| | | | |
|---|---|---|---|
| WO | WO 2008/079269 A2 | * | 12/2006 |
| WO | 2010065944 A1 | | 6/2010 |
| WO | 2013139348 A1 | | 9/2013 |
| WO | 2014082083 A1 | | 5/2014 |

OTHER PUBLICATIONS

Hanke et al. Clinical Chemistry. 2007. 53: 2070-2077 (Year: 2007).*
Heggard et al. International Journal of Cancer. May 4, 2011. 102. 130: 1378-1386 (Year: 2011).*
Min et al BMC Genomics. 2010. 11:96 (Year: 2010).*
Tuttle et al PLoS ONE. Jan. 9, 2014: e87325 (Year: 2014).*
Gokmen-Polar et al. Cancer Research. 2001. 61: 1375-1381 (Year: 2001).*
Haynes et al Electrophoresis. 1998. 19: 1862-1871 (Year: 1998).*
Rachow et al PLoS ONE. Feb. 2013. 8(2): e55116, p. 1-13 (Year: 2013).*
Hintsala et al Int J Clin Exp Pathol. 2013. 6(12): 2855-2865 (Year: 2013).*
Haider et al J Investigative Dermatology. 2006. 126:869-881 (Year: 2006).*
Abiko et al Cancer Letters. 1994. 143: 37-43 (Year: 1994).*
Palumbo, A. & Sonneveld, P. Preclinical and clinical evaluation of elotuzumab, a SLAMF7-targeted humanized monoclonal antibody in development for multiple myeloma. Expert review of hematology 8, 481-491, doi: 10.1586/17474086.2015.1053866 (2015).
Papazoglou E, et al. The role of Syk kinase in UV mediated skin damage. Br J Dermatol. Jul. 2011;165(1):69-77.
Pentland, A. P., et al. Reduction of UV-induced skin tumors in hairless mice by selective COX-2 inhibition. Carcinogenesis 20, 1939-1944 (1999).
Perera, D. et al. Differential DNA repair underlies mutation hotspots at active promoters in cancer genomes. Nature 532, 259-263, doi: 10.1038/nature17437 (2016).
Pfeifer, G. P., et al. Mutations induced by ultraviolet light. Mutation research 571, 19-31, doi: 10.1016/j.mrfmmm.2004.06.057 (2005).
Pickering, C. R. et al. Mutational landscape of aggressive cutaneous squamous cell carcinoma. Clinical cancer research: an official journal of the American Association for Cancer Research 20, 6582-6592, doi: 10.1158/1078-0432. CCR-14-1768 (2014).

(Continued)

*Primary Examiner* — Carla J Myers
(74) *Attorney, Agent, or Firm* — Bryan Cave Leighton Paisner, LLP

(57) ABSTRACT

The present invention provides methods of detecting ultraviolet radiation (UVR)-induced skin damage in a subject. The method includes the steps of: a) obtaining a skin sample from the subject; b) analyzing expression levels in the skin sample of UVR-induced differentially expressed genes (DEGs) listed in Table 8 or a subset thereof; and c) comparing the expression levels of the UVR-induced DEGs to a control skin sample; wherein, when the expression levels of the UVR-induced DEGs in the skin sample is above or below the level of each of the UVR-induced DEGs in the control sample, the subject is identified as likely being afflicted with UVR-induced skin damage. Also provided are methods for measuring the effectiveness of a test agent in reducing ultraviolet radiation (UVR)-induced damage.

8 Claims, 31 Drawing Sheets

(56) References Cited

OTHER PUBLICATIONS

Pleasance, E. D., et al. (2010) A comprehensive catalogue of somatic mutations from a human cancer genome. Nature 463, 191-196.
Rada-Iglesias, A. et al. A unique chromatin signature uncovers early developmental enhancers in humans. Nature 470, 279-283, doi:10.1038/nature09692 (2011).
Ralfkiaer U, et al. Diagnostic microRNA profiling in cutaneous T-cell lymphoma (CTCL). Blood. Nov. 24, 2011;118(22):5891-900.
Rao RC, et al. EZH2, proliferation rate, and aggressive tumor subtypes in cutaneous basal cell carcinoma. JAMA Oncol. Jul. 1, 2016;2(7):962-3.
Rieger, K. E., and Chu, G. (2004) Portrait of transcriptional responses to ultraviolet and ionizing radiation in human cells. Nucleic acids research 32, 4786-4803.
Rippa, A. L., et al. The role of integrins in the development and homeostasis of the epidermis and skin appendages. Acta naturae 5, 22-33 (2013).
Robinson, J. K. (2005) Sun exposure, sun protection, and vitamin D. Jama 294, 1541-1543.
Rogers, H. W., et al. Incidence Estimate of Nonmelanoma Skin Cancer (Keratinocyte Carcinomas) in the U.S. Population, 2012. JAMA dermatology 151, 1081-1086, doi: 10.1001/jamadermatol.2015.1187 (2015).
Santana-Filho AP, et al. NMR metabolic fingerprints of murine melanocyte and melanoma cell lines: application to biomarker discovery. Sci Rep. Feb. 15, 2017;7:42324.
Schick, S. et al. Dynamics of chromatin accessibility and epigenetic state in response to UV damage. Journal of cell science 128, 4380-4394, doi: 10.1242/jcs.173633 (2015).
Schutze, D. M. et al. Longitudinal assessment of DNA methylation changes during HPVE6E7-induced immortalization of primary keratinocytes. Epigenetics 10, 73-81, doi: doi: 10.4161/15592294.2014.990787 (2015).
Seite, S., et al. (2010) Photodamage to human skin by suberythemal exposure to solar ultraviolet radiation can be attenuated by sunscreens: a review. The British journal of dermatology 163, 903-914.
Shain, A. H. et al. The Genetic Evolution of Melanoma from Precursor Lesions. The New England journal of medicine 373, 1926-1936, doi: 10.1056/NEJMoa1502583 (2015).
Shen, Y., et al. Transcriptome Analysis Identifies the Dysregulation of Ultraviolet Target Genes in Human Skin Cancers. PloS one 11, e0163054, doi: 10.1371/journal.pone.0163054 (2016).
Skobowiat, C. & Slominski, A. T. UVB Activates Hypothalamic-Pituitary-Adrenal Axis in C57BL/6 Mice. The Journal of investigative dermatology 135, 1638-1648, doi: 10.1038/jid.2014.450 (2015).
Slominski, A. et al. Steroidogenesis in the skin: implications for local immune functions. The Journal of steroid biochemistry and molecular biology 137, 107-123, doi: 10.1016/j.jsbmb.2013.02.006 (2013).
Slominski, A. T. et al. Key role of CRF in the skin stress response system. Endocrine reviews 34, 827-884, doi: 10.1210/er.2012-1092 (2013).
Slominski, A. T. et al. Local melatoninergic system as the protector of skin integrity. International journal of molecular sciences 15, 17705-17732, doi: 10.3390/ijms151017705 (2014).
Slominski, A. T. et al. Novel non-calcemic secosteroids that are produced by human epidermal keratinocytes protect against solar radiation. The Journal of steroid biochemistry and molecular biology 148, 52-63, doi: 10.1016/j.jsbmb.2015.01.014 (2015).
Slominski, A. T. et al. Sensing the environment: regulation of local and global homeostasis by the skin's neuroendocrine system. Advances in anatomy, embryology, and cell biology 212, v, vii, 1-115 (2012).
Slominski, A.T., et al. Melanin pigmentation in mammalian skin and its hormonal regulation. Physiological reviews 84, 1155-1228, doi: 10.1152/physrev.00044.2003 (2004).
Stern, R. S. Prevalence of a history of skin cancer in 2007: results of an incidence-based model. Archives of dermatology 146, 279-282, doi: 10.1001/archdermatol.2010.4 (2010).
Subramanian, A., et al. (2005) Gene set enrichment analysis: a knowledge-based approach for interpreting genome-wide expression profiles. Proceedings of the National Academy of Sciences of the United States of America 102, 15545-15550.
Sun, X., et al. Distinctive molecular responses to ultraviolet radiation between keratinocytes and melanocytes. Experimental dermatology, doi: 10.1111/exd.13057 (2016).
Szklarczyk, D., et al. (2015) STRING v10: protein-protein interaction networks, integrated over the tree of life. Nucleic acids research 43, D447-452.
Takao, J., et al. (2002) Genomic scale analysis of the human keratinocyte response to broad-band ultraviolet-B irradiation. Photodermatology, photoimmunology & photomedicine 18, 5-13.
Tannour-Louet, M. et al. Increased expression of CYP24A1 correlates with advanced stages of prostate cancer and can cause resistance to vitamin D3-based therapies. FASEB journal: offcial publication of the Federation of American Societies for Experimental Biology 28, 364-372, doi: 10.1096/fj.13-236109 (2014).
The Surgeon General's Call to Action to Prevent Skin Cancer, Washington (DC) (2014).
Thurman, R. E. et al. The accessible chromatin landscape of the human genome. Nature 489, 75-82, doi: 10.1038/nature11232 (2012).
Tieu, E. W. et al. Rat CYP24A1 acts on 20-hydroxyvitamin D3 producing hydroxylated products with increased biological activity. Biochemical pharmacology 84, 1696-1704, doi: 10.1016/j.bcp.2012.09.032 (2012).
Van Eck, N. J., et al. (2010) A Comparison of Two Techniques for Bibliometric Mapping: Multidimensional Scaling and VOS. J Am Soc Inf Sci Tec 61, 2405-2416.
Vandiver, A. R. et al. Age and sun exposure-related widespread genomic blocks of hypomethylation in nonmalignant skin. Genome biology 16, 80, doi: 10.1186/s13059-015-0644-y (2015).
Wang, Y. et al. A complex network of factors with overlapping affinities represses splicing through intronic elements. Nature structural & molecular biology 20, 36-45, doi: 10.1038/nsmb.2459 (2013).
Warr, A. et al. Exome Sequencing: Current and Future Perspectives. G3 5, 1543-1550, doi: 10.1534/g3.115.018564 (2015).
Wei, Y. et al. SEA: a super-enhancer archive. Nucleic acids research 44, D172-179, doi: 10.1093/nar/gkv1243 (2016).
Whyte, W. A. et al. Master transcription factors and mediator establish super-enhancers at key cell identity genes. Cell 153, 307-319, doi: 10.1016/j.cell.2013.03.035 (2013).
Wu, S. et al. History of Severe Sunburn and Risk of Skin Cancer Among Women and Men in 2 Prospective Cohort Studies. American journal of epidemiology 183, 824-833, doi: 10.1093/aje/kwv282 (2016).
Wu, S., et al. (2014) Long-term ultraviolet flux, other potential risk factors, and skin cancer risk: a cohort study. Cancer epidemiology, biomarkers & prevention : a publication of the American Association for Cancer Research, cosponsored by the American Society of Preventive Oncology 23, 1080-1089.
Yang, G., et al. (2006) Expression profiling of UVB response in melanocytes identifies a set of p53-target genes. The Journal of investigative dermatology 126, 2490-2506.
You, Y. N., et al. (2015) Oncotype DX® colon cancer assay for prediction of recurrence risk in patients with stage II and III colon cancer: A review of the evidence. Surgical oncology 24, 61-66.
Zanotti, L., et al. (2014) Diagnostic tests based on gene expression profile in breast cancer: from background to clinical use. Tumour biology: the journal of the International Society for Oncodevelopmental Biology and Medicine 35, 8461-8470.
Zentner, G. E., et al. Epigenetic signatures distinguish multiple classes of enhancers with distinct cellular functions. Genome research 21, 1273-1283, doi: 10.1101/gr.122382.111 (2011).
Zhang, X. et al. Solar Simulated Ultraviolet Radiation Induces Global Histone Hypoacetylation in Human Keratinocytes. PloS one 11, e0150175, doi: 10.1371/journal.pone.0150175 (2016).
International Search Report for PCT/US2017/022848, dated Jul. 19, 2017.
International Written Opinion for PCT/US2017/022848 dated Jul. 19, 2017.

(56) References Cited

OTHER PUBLICATIONS

Afaq, F., et al. Photochemoprevention of ultraviolet B signaling and photocarcinogenesis. Mutation research 571, 153-173, doi: 10.1016/j.mrfmmm.2004.07.019 (2005).
Anders, S., and Huber, W. (2010) Differential expression analysis for sequence count data. Genome biology 11, R106.
Aubin, F. Mechanisms involved in ultraviolet light-induced immunosuppression. European journal of dermatology: EJD 13, 515-523 (2003).
Batagelj, V., and Mrvar, A. (2004) Pajek—Analysis and visualization of large networks. Math Visual, 77-103.
Bens, G. (2014) Sunscreens. Advances in experimental medicine and biology 810, 429-463.
Besaratinia, A. et al. Wavelength dependence of ultraviolet radiation-induced DNA damage as determined by laser iradiation suggests that cyclobutane pyrimidine dimers are the principal DNA lesions produced by terrestrial sunlight. FASEB journal: official publication of the Federation of American Societies for Experimental Biology 25, 3079-3091, doi: 10.1096/fj.11-187336 (2011).
Birch-Machin MA, et al. Mitochondrial DNA damage as a biomarker for ultraviolet radiation exposure and oxidative stress. Br J Dermatol. Jul. 2013; 169(Suppl 2): pp. 9-14.
Boice, J. D., Jr. (2005) Radiation-induced thyroid cancer—what's new? Journal of the National Cancer Institute 97, 703-705.
Bonn, S. et al. Tissue-specific analysis of chromatin state identifies temporal signatures of enhancer activity during embryonic development. Nature genetics 44, 148-156, doi: 10.1038/ng.1064 (2012).
Brash, D. E. UV signature mutations. Photochemistry and photobiology 91, 15-26, doi: 10.1111/php.12377 (2015).
Brozyna, A. A. et al. CYP24A1 expression inversely correlates with melanoma progression: clinic-pathological studies. International journal of molecular sciences 15, 19000-19017, doi: 10.3390/ijms151019000 (2014).
Calo, E. & Wysocka, J. Modification of enhancer chromatin: what, how, and why? Molecular cell 49, 825-837, doi: 10.1016/j.molcel.2013.01.038 (2013).
Cowley, G. S. et al. Parallel genome-scale loss of function screens in 216 cancer cell lines for the identification of context-specific genetic dependencies. Scientific data 1, 140035, doi: 10.1038/sdata.2014.35 (2014).
Creyghton, M. P. et al. Histone H3K27ac separates active from poised enhancers and predicts developmental state. Proceedings of the National Academy of Sciences of the United States of America 107, 21931-21936, doi: 10.1073/pnas.1016071107 (2010).
Dawes, J. M. et al. Genome-wide transcriptional profiling of skin and dorsal root ganglia after ultraviolet-B-induced inflammation. PloS one 9, e93338, doi: 10.1371/journal.pone.0093338 (2014).
Dazard, J. E., et al. (2003) Genome-wide comparison of human keratinocyte and squamous cell carcinoma responses to UVB irradiation: implications for skin and epithelial cancer. Oncogene 22, 2993-3006.
De la Fuente, H., et al. (2009) Identification of genes responsive to solar simulated UV radiation in human monocyte-derived dendritic cells. PloS one 4, e6735.
Dennis, L. K., et al. (2003) Sunscreen use and the risk for melanoma: a quantitative review. Annals of internal medicine 139, 966-978.
Djebali, S. et al. Landscape of transcription in human cells. Nature 489, 101-108, doi: 10.1038/nature11233 (2012).
Elbediwy, A. et al. Integrin signalling regulates YAP and TAZ to control skin homeostasis. Development 143, 1674-1687, doi: 10.1242/dev.133728 (2016).
Ernst, J. et al. Mapping and analysis of chromatin state dynamics in nine human cell types. Nature 473, 43-49, doi: 10.1038/nature09906 (2011).
Fartasch, M., et al. (2012) The Relationship Between Occupational Sun Exposure and Non-Melanoma Skin Cancer. Dtsch Arztebl Int 109, 715-U714.
Fortis SP, et al. Potential prognostic molecular signatures in a preclinical model of melanoma. Anticancer Res. Jan. 2017;37(1):143-148.
Greenberg E, et al. Epigenetic biomarkers in skin cancer. Cancer Lett. Jan. 2012; 342(2): pp. 170-177.
Gronniger, E. et al. Aging and chronic sun exposure cause distinct epigenetic changes in human skin. PLoS genetics 6, e1000971, doi: 10.1371/journal.pgen.1000971 (2010).
Guo, Y. et al. Exome sequencing generates high quality data in non-target regions. BMC genomics 13, 194, doi: 10.1186/1471-2164-13-194 (2012).
Guy, G. P., Jr., et al. (2015) Prevalence and costs of skin cancer treatment in the U.S., 2002-2006 and 2007-2011. American journal of preventive medicine 48, 183-187.
Gyorffy, B., et al. (2015) Multigene prognostic tests in breast cancer: past, present, future. Breast cancer research : BCR 17, 11.
Hacker, E., et al. (2013) The effect of MC1R variants and sunscreen on the response of human melanocytes in vivo to ultraviolet radiation and implications for melanoma. Pigment cell & melanoma research 26, 835-844.
Heckman, C. J., et al. (2013) Minimal Erythema Dose (MED) testing. Journal of visualized experiments : JoVE, e50175.
Heintzman, N. D. et al. Distinct and predictive chromatin signatures of transcriptional promoters and enhancers in the human genome. Nature genetics 39, 311-318, doi: 10.1038/ng1966 (2007).
Hnisz, D. et al. Super-enhancers in the control of cell identity and disease. Cell 155, 934-947, doi: 10.1016/j.cell.2013.09.053 (2013).
Hobaus, J. et al. Impact of CYP24A1 overexpression on growth of colorectal tumour xenografts in mice fed with vitamin D and soy. International journal of cancer. Journal international du cancer 138, 440-450, doi: 10.1002/ijc.29717 (2016).
Hubers, A. J. et al. DNA hypermethylation analysis in sputum for the diagnosis of lung cancer: training validation set approach. British journal of cancer 112, 1105-1113, doi: 10.1038/bjc.2014.636 (2015).
Hudson, L. G., et al. (2010) Microarray analysis of cutaneous squamous cell carcinomas reveals enhanced expression of epidermal differentiation complex genes. Molecular carcinogenesis 49, 619-629.
Kadekaro, A. L. et al. Melanocortin 1 receptor genotype: an important determinant of the damage response of melanocytes to ultraviolet radiation. FASEB journal: official publication of the Federation of American Societies for Experimental Biology 24, 3850-3860, doi: 10.1096/fj.10-158485 (2010).
Khurana, E. et al. Role of non-coding sequence variants in cancer. Nature reviews. Genetics 17, 93-108, doi: 10.1038/nrg.2015.17 (2016).
Konger, R. L., et al. The peroxisome proliferator-activated receptor gamma system regulates ultraviolet B-induced prostaglandin in production in human epidermal keratinocytes. PPAR research 2010, 467053, doi: 10.1155/2010/467053 (2010).
Lahtz, C. et al. UVB irradiation does not directly induce detectable changes of DNA methylation in human keratinocytes. F1000Research 2, 45, doi: 10.12688/f1000research.2-45.v1 (2013).
Lautenschlager, S., et al. (2007) Photoprotection. Lancet 370, 528-537.
Lian CG, et al. Loss of 5-hydroxymethylcytosine is an epigenetic hallmark of melanoma. Cell. Sep. 14, 2012;150(6):1135-46.
Lin, S. W., et al. (2012) Prospective study of ultraviolet radiation exposure and risk of cancer in the United States. International journal of cancer. Journal international du cancer 131, E1015-1023.
Liu, L. et al. Hairless is a histone H3K9 demethylase. FASEB journal: official publication of the Federation of American Societies for Experimental Biology 28, 1534-1542, doi: 10.1096/fj.13-237677 (2014).
Loven, J. et al. Selective inhibition of tumor oncogenes by disruption of super-enhancers. Cell 153, 320-334, doi: 10.1016/j.cell.2013.03.036 (2013).
Mao, P., et al. Chromosomal landscape of UV damage formation and repair at single nucleotide resolution. Proceedings of the National Academy of Sciences of the United States of America 113, 9057-9062, doi: 10.1073/pnas.1606667113 (2016).

(56) References Cited

OTHER PUBLICATIONS

Mukhopadhyay, P., et al. Murine melanomas accelerated by a single UVR exposure carry photoproduct footprints but lack UV signature C > T mutations in critical genes. Oncogene 35, 3342-3350, doi: 10.1038/onc.2015.386 (2016).

Niederriter, A. R., et al. Super Enhancers in Cancers, Complex Disease, and Developmental Disorders. Genes 6, 1183-1200, doi: 10.3390/genes6041183 (2015).

Osterwalder, U., and Herzog, B. (2009) Sun protection factors: worldwide confusion. The British journal of dermatology 161 Suppl 3, 13-24.

* cited by examiner

FIG. 8C

| 4 h | DGE > 1 | DGE (-1,1) | DGE < -1 |
|---|---|---|---|
| DHA > 1 | 24 | 38 | 12 |
| DHA (-1,1) | 1275 | 9010 | 2643 |
| DHA < -1 | 39 | 226 | 56 |

| 72 h | DGE > 1 | DGE (-1,1) | DGE < -1 |
|---|---|---|---|
| DHA > 1 | 74 | 78 | 15 |
| DHA (-1,1) | 800 | 10700 | 443 |
| DHA < -1 | 54 | 965 | 170 |

FIG. 9A

| Top ranked motifs | TFs | P-value |
|---|---|---|
| ATGAcTCAT | FOSL1 | 1e-856 |
| ATGACTCAT | ATF3 | 1e-820 |
| TGACTCA | JUN | 1e-477 |
| CATGCC | TP53 | 1e-214 |
| TGCTGAcTCA | BACH2 | 1e-185 |
| TTCC | FLI1 | 1e-184 |
| CTAATTG | ISL1 | 1e-66 |
| CCGGAAGT | ETV1 | 1e-45 |
| CCGGAAT | TEAD4 | 1e-28 |
| TCA TTAC | SIX1 | 1e-22 |
| CACGTG | ARNTL | 1e-13 |

NEXT-GENERATION BIOMARKERS TO DETECT SUN DAMAGE AND PREDICT SKIN CANCER RISK

CROSS-REFERENCE TO RELATED APPLICATIONS

The present application is the National Stage of International Application No. PCT/US17/22848 filed Mar. 16, 2017, which claims benefit to U.S. Provisional Application No. 62/458,535 filed Feb. 13, 2017, and U.S. Provisional Application No. 62/313,425 filed Mar. 25, 2016. The entire contents of the aforementioned applications are incorporated by reference as if recited in full herein.

GOVERNMENT FUNDING

This invention was made with government support under ES009089 and AR064315 awarded by National Institutes of Health. The government has certain rights in the invention.

BACKGROUND OF THE INVENTION

Skin cancer is the most prevalent cancer worldwide. (Guy 2015; Rogers 2015) Every year in the United States, nearly 5 million people are treated for skin cancer, at an estimated cost of $8.1 billion. (The surgeon General 2014) Solar ultraviolet radiation (UVR), especially the UVB spectrum of sunlight, is widely recognized as the major carcinogen that promotes skin cancer development; and interplay with genetic factors is also involved. (Wu 2014; Robinson 2005; Pleasance 2010) Most skin cancer cases are preventable through proper protection against harmful UVR exposure, and sunscreen is one of the commonly used sun protection strategies especially in skin-cancer susceptible populations. (Lautenschlger 2007) However, there are controversies surrounding the efficacy of sunscreen products. (Osterwalder 2009; Bens 2014; Dennis 2003; Hacker 2013)

Despite recent efforts to address risk factors, skin cancer rates continue to rise, mainly due to unprotected UV exposure. More importantly, there are no sensitive biomarkers available for monitoring solar UVR damage and predicting skin cancer risk. The current method for monitoring sun damage relies on the use of minimal erythema dose (MED), which refers to the amount of UVR that produces visible skin redness within 24 hours following exposure. As an indicator of sun damage, MED is both insensitive and inadequate because significant molecular and cellular damage occurs at sub-erythema doses lower than one MED. (Seite 2010; Heckman 2013) The lack of sensitive biomarkers for accurate assessment of sun damage and to test the ability of sunscreens in preventing sun damage and reducing skin cancer risk remains the greatest unmet clinical need in skin cancer research.

Numerous studies in the past have attempted to identify UVR biomarkers focusing on UVR-induced changes in the activity of individual genes as biomarkers to detect skin damage and cancer risk. (Dawes 2014; da le Fuente 2009; Yang 2006; Rieger 2004; Dazard 2003; Takao 2002) Such individual markers are simple and easy to characterize, but it is difficult for them to produce consistent and reliable information on UVR damage and skin cancer risk due to the complex effects of UVR on multiple biological pathways leading to skin neoplastic growth in addition to the variations in skin type-dependent UVR sensitivity.

In view of the foregoing, there exists an ongoing need to provide new and improved methods for detecting sun damage and predicting skin cancer risk. The present disclosure is directed towards solving this and other needs.

SUMMARY OF THE INVENTION

Numerous studies in the past have attempted to identify UVR biomarkers focusing on UVR-induced changes in the activity of individual genes as biomarkers to detect skin damage and cancer risk. Such individual markers are simple and easy to characterize, but it is difficult for them to produce consistent and reliable information on UVR damage and skin cancer risk due to the complex effects of UVR on multiple biological pathways leading to skin neoplastic growth in addition to the variations in skin type-dependent UVR sensitivity. To obtain UVR biomarkers with better reliability and accuracy, a panel of UVR-responsive genes has been identified through comprehensive transcriptomic profiling studies. Functions of these carefully selected UVR biomarker genes span several biological pathways including inflammation, cell growth and proliferation, DNA repair, and cancer pathogenesis. This panel of genes has been subjected to rigorous validation by both bioinformatics and experimental approaches to confirm that their mRNA expressions are consistently responsive to UVR among different skin types. Furthermore, the UVR-induced mRNA expression changes in the biomarker genes persist long after UVR, highlighting their potential as reliable UVR biomarkers.

The UVR biomarker panel can serve to set a new industrial standard in testing UVR-protective effects of sunscreen products to prevent cancer-inducing sun damage. Such a panel may also be used in clinical diagnosis to assist health care providers with a sensitive tool in assessing excessive sun exposure and skin cancer risk. To facilitate its future industrial and clinical applications, a gene array system is being designed in a 384-well plate format to allow simultaneous detection of the expression of the UVR biomarker genes from multiple samples. Ultimately, we anticipate that our UVR biomarker panel together with the high capacity screening assay system will revolutionize how we assess sun damage and predict skin cancer risk to achieve effective prevention and reduction of skin cancer-related illness, death, and health care costs.

The present invention provides methods of detecting ultraviolet radiation (UVR)-induced skin damage in a subject. In some embodiments, this method comprises the steps of: a) obtaining a skin sample from the subject; b) analyzing expression levels in the skin sample of UVR-induced differentially expressed genes (DEGs) listed in Table 8 or a subset thereof; and c) comparing the expression levels of the UVR-induced DEGs to a control skin sample; wherein, when the expression levels of the UVR-induced DEGs in the skin sample is above or below the level of each of the UVR-induced DEGs in the control sample, the subject is identified as likely being afflicted with UVR-induced skin damage.

The present invention also provides a method of identifying or monitoring skin cancer in a test subject. In some embodiments, this method comprises the steps of: a) analyzing expression levels in a biological sample obtained from the subject of UVR-induced differentially expressed genes (DEGs) listed in Table 8, or a subset thereof; b) comparing the expression levels of the UVR-induced DEGs in the biological sample with a predetermined reference standard for the genes; and c) identifying or monitoring skin cancer in the test subject based on the comparison in b).

The present invention also provides a kit for detecting ultraviolet radiation (UVR)-induced skin damage in a subject. In some embodiments, this kit comprises: a set of primers or probes that specifically bind to UVR-induced differentially expressed genes (DEGs) listed in Table 8 or a subset thereof, packaged together with instructions for its use.

The present invention also provides a kit for identifying or monitoring skin cancer in a subject. In some embodiments, this kit comprises: a set of primers or probes that specifically bind to UVR-induced differentially expressed genes (DEGs) listed in Table 8 or a subset thereof, packaged together with instructions for its use.

The present invention also provides a method for measuring the effectiveness of a test agent in reducing ultraviolet radiation (UVR)-induced damage. In some embodiments, this method comprises the steps of: a) irradiating a test skin sample, to which the test agent has been applied, with UV radiation; b) obtaining an expression profile of the UVR-induced differentially expressed genes (DEGs) listed in Table 8, or a subset thereof, in the test skin sample; and c) comparing the expression profile of the UVR-induced DEGs, or a subset thereof, from the test skin sample, with an expression profile of the same genes in a reference skin sample and a control skin sample, wherein the reference skin sample is irradiated in the absence of the test agent, and the normal, control skin sample is not irradiated; wherein if the gene expression profile of the test skin sample is the same or substantially similar to the gene expression profile of the normal, control skin sample, the test agent is effective at reducing UVR-induced damage, whereas if the gene expression profile of the test skin sample is the same or substantially similar to the gene expression profile of the reference skin sample, the test agent is not effective at reducing UVR-induced damage.

The present invention also provides a method for diagnosing UVR-induced skin damage in a subject by analyzing a sample from the subject for an expression profile of UVR-induced DEGs listed in Table or a subset thereof that is different from an expression profile of the same genes in a normal, control sample, wherein the subject is diagnosed with UVR-induced skin damage if the expression profile of the subject differs from the expression profile from the normal, control sample.

The present invention also provides a method for diagnosing skin cancer in a subject by analyzing a sample from the subject for the presence or absence of squamous cell carcinoma or pre-cancerous skin lesion cells by analyzing a sample from the subject for an expression profile of UVR-induced DEGs listed in Table 8 or a subset thereof that is different from an expression profile of the same genes in a normal, control sample, wherein the subject is diagnosed with skin cancer if squamous cell carcinoma or pre-cancerous skin lesion cells are detected.

The present invention also provides a method for diagnosing and treating UVR-induced skin damage in a subject comprising: analyzing a sample from the subject for an expression profile of UVR-induced DEGs listed in Table 8 or a subset thereof that is different from an expression profile of the same genes in a normal, control sample, wherein the patient is diagnosed with UVR-induced skin damage if the expression profile of the subject differs from the expression profile from the normal, control sample; and administering a treatment for UVR-induced skin damage to the diagnosed subject.

The present invention also provides a method for treating skin cancer in a subject comprising: requesting a test providing the results of an analysis of whether the subject has an expression profile of UVR-induced DEGs listed in Table 8 or a subset thereof that is different from an expression profile of the same genes in a normal, control sample; and administering a treatment for skin cancer to the subject if the expression profile of the subject differs from the expression profile from the normal, control sample.

BRIEF DESCRIPTION OF THE DRAWINGS

FIG. 8C shows a summary of the overall correlations between DGE and DHA changes among UV-responsive genes at 4 h or 72 h after UVR. Pink highlights positive correlations; green highlights inverse correlations between DGE and DHA.

FIG. 9A is a motif analysis showing a significant enrichment of multiple TF motifs in UV-induced DHA regions in keratinocytes following UVR.

DETAILED DESCRIPTION OF THE INVENTION

Figure 1A:
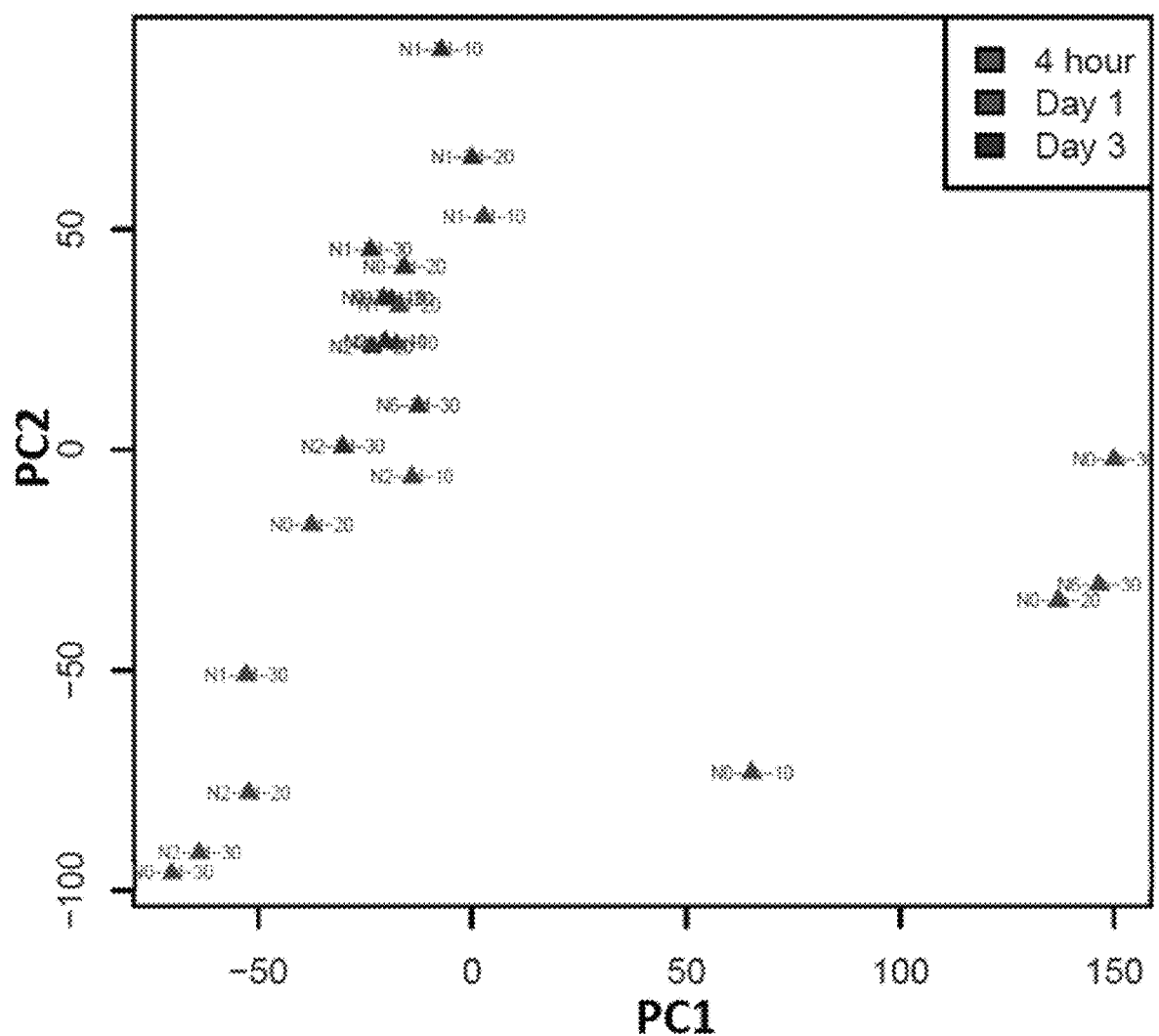
FIG. 1A shows PCA analysis demonstrating time-dependent clustering of UVR-responsive transcriptomic profiles in human keratinocytes.

The present invention provides methods of detecting ultraviolet radiation (UVR)-induced skin damage in a subject. In some embodiments, this method comprises the steps of: a) obtaining a skin sample from the subject; b) analyzing expression levels in the skin sample of UVR-induced differentially expressed genes (DEGs) listed in Table 8 or a subset thereof; and c) comparing the expression levels of the UVR-induced DEGs to a control skin sample; wherein, when the expression levels of the UVR-induced DEGs in the skin sample is above or below the level of each of the UVR-induced DEGs in the control sample, the subject is identified as likely being afflicted with UVR-induced skin damage.

As used herein, "ultraviolet radiation (UVR)-induced skin damage" is any damage to the skin caused by exposure to UV radiation and includes, for example, photocarcinogenesis (e.g., melanoma), photoaging (e.g., wrinkles, loss of elasticity), immunosuppression, and oxidative stress. In some embodiments, the radiation is solar UV, comprising UVA, UVB, and/or UVC. In other embodiments, the UV radiation is generated by a lamp.

As used herein, a "subject" is a mammal, preferably, a human. In addition to humans, categories of mammals within the scope of the present invention include, for example, agricultural animals, domestic animals, laboratory animals, etc.

The phrase "skin sample" or "biological sample" as used herein, is intended to mean any sample comprising a skin cell or skin tissue in which expression of a gene or gene product can be detected. For example, skin cells or skin tissue may be taken from the dermis or epidermis, or a combination of both. The skin sample can be used either directly as obtained from the source or following a pre-treatment to modify the character of the sample. The sample may be obtained by a variety of methods including, but not limited to, punch biopsy, surgical excision, and non-invasive or minimally invasive skin sampling methods such as a wet swabbing, tapelift, cotton tip swabbing, scraping of skin using a sterile surgical blade, scraping of skin using a wooden scraper, sticky surface of an adhesive pad (CapSure™ Clean-up Pad, Arcturus), film from LCM MacroCap™ (Arcturus), heated film from LCM MacroCap™ (Arcturus) and employing a small gauge needle (for example, 28 gauge), to collect micro-cores of skin tissue. These methods are well known in the art.

Alternatively, a skin sample may be a skin equivalent or a human or non-human cultured cell, for example, a keratinocyte, a melanocyte, a dermal fibroblast, a mast cell, an endothelial cell, a sebocyte, a hair papilla, or a matrix cell.

A "control" refers to a sample or standard used for comparison with an experimental sample, such as a skin sample obtained from a test subject exposed to UVR. In some embodiments, the control is a sample that has not been exposed to UVR or a non-UVR exposed sample obtained from the test subject. In some embodiments, the control is a skin sample whose exposure to UVR has been blocked or attenuated. In some embodiments, the control is a historical control or standard reference value or range of values (i.e. a previously tested control sample, such as a group of skin samples that were not exposed to UVR, or group of samples that represent baseline or normal values, such as the level of gene expression in non-UVR exposed tissue).

The differentially-expressed genes (DEGs) listed in Table 8 are genes or gene products that are modulated in skin in response to UVR exposure. Accordingly, using an assay to measure the level of the expression, function, or activity of DEGs in skin is diagnostic and prognostic of UVR-induced skin damage, photoaging, or photocarcinogenesis. A DEG may be detected at either the nucleic acid or protein level. The expression level of a given gene measured at the nucleotide level refers to the amount of RNA transcribed from the gene measured on a relevant or absolute quantitative scale, and in general refers to the relative abundance of the accumulated mRNA transcript. The expression level of a given gene measured at the protein level refers to the amount of protein translated from the transcribed RNA measured on a relevant or absolute quantitative scale.

Differential expression, as used herein, means that the expression levels of certain genes, as measured at the RNA or protein level, are different between biological samples in different states, tissues, or type of cells. Differential expression may also be observed relative to a reference standard. Such standard may be determined based on the context of the expression experiments, the biological properties of the genes under study, and/or statistical significance criteria.

In some embodiments, comparing the expression levels of the UVR-induced DEGs to a control skin sample may require a quantitative or semi-quantitative determination. Other embodiments may involve a relative determination (e.g. a ratio relative to another marker, or a measurement relative to the same marker in a control sample), and other embodiments may involve a threshold determination (e.g. a yes/no determination whether a level is above or below a threshold).

In some embodiments, the analyzing step comprises carrying out next-generation sequencing of an RNA sample from the subject to identify genes from Table 8, or a subset thereof, that have a different expression profile compared to controls.

Preferably, the next-generation sequencing is whole transcriptome shotgun sequencing (RNA-Seq). Other methods of analyzing expression levels are well known in the art, and may include microarrays, ChIP sequencing, SAGE (serial analysis of gene expression), tiling arrays, nucleic acid hybridization techniques, nucleic acid reverse transcription methods, nucleic acid amplification methods, western blots, northern blots, southern blots, ELISA, immunoprecipitation, immunofluorescence, flow cytometry, and immunocytochemistry.

The present invention also provides methods of identifying or monitoring skin cancer in a test subject. In some embodiments, the method comprises: a) analyzing expression levels in a biological sample obtained from the subject of UVR-induced differentially expressed genes (DEGs) listed in Table 8, or a subset thereof; b) comparing the expression levels of the UVR-induced DEGs in the biological sample with a predetermined reference standard for the genes; and c) identifying or monitoring skin cancer in the test subject based on the comparison in b).

A "predetermined reference standard" as used herein may be determined empirically or historically from a single or multiple control samples. For monitoring a test subject, the predetermined reference standard may be a prior level of expression from the same test subject, a control subject or subjects, or a previously established range of normal, control values.

The present invention also provides kits for detecting ultraviolet radiation (UVR)-induced skin damage in a subject. In some embodiments, the kit comprises: a set of primers or probes that specifically bind to UVR-induced differentially expressed genes (DEGs) listed in Table 8 or a subset thereof, packaged together with instructions for its use.

The phrase "specifically bind" and the like refers to a binding reaction between two molecules that is at least two times the background and more typically more than 10 to 100 times background molecular associations under physiological conditions.

The present invention also provides methods for measuring the effectiveness of a test agent in reducing ultraviolet radiation (UVR)-induced damage. In some embodiments, the method comprises: a) irradiating a test skin sample, to which the test agent has been applied, with UV radiation; b) obtaining an expression profile of the UVR-induced differentially expressed genes (DEGs) listed in 8 Table 8, or a subset thereof, in the test skin sample; and c) comparing the expression profile of the UVR-induced DEGs, or a subset thereof, from the test skin sample, with an expression profile of the same genes in a reference skin sample and a control skin sample, wherein the reference skin sample is irradiated in the absence of the test agent, and the normal, control skin sample is not irradiated; wherein if the gene expression profile of the test skin sample is the same or substantially similar to the gene expression profile of the normal, control skin sample, the test agent is effective at reducing UVR-induced damage, whereas if the gene expression profile of the test skin sample is the same or substantially similar to the gene expression profile of the reference skin sample, the test agent is not effective at reducing UVR-induced damage.

As used herein, the phrase "same or substantially similar to" refers to statistically no significant difference in the expression level between the test skin sample and the control skin sample. Conversely, the phrase "different from" and the like refers to a statistically significant difference in expression.

The present invention also provides methods for diagnosing and treating UVR-induced skin damage in a subject. In some embodiments, the method comprises: analyzing a sample from the subject for an expression profile of UVR-induced DEGs listed in Table 8 or a subset thereof that is different from an expression profile of the same genes in a normal, control sample, wherein the subject is diagnosed with UVR-induced skin damage if the expression profile of the subject differs from the expression profile from the normal, control sample; and administering a treatment for UVR-induced skin damage to the diagnosed subject.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods of the present invention may be used to slow the development of symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

Skin cancer is the most common cancer in the United States. According to Skin Cancer Foundation statistics, one in every five Americans will develop skin cancer in their lifetime. Skin cancer greatly affects quality of life and creates substantial health care costs for individuals, families and the nation. Despite the fact that most skin cancer cases are preventable, its rates continue to rise mainly due to unnecessary UV radiation exposure and a lack of reliable biomarkers that can effectively monitor UV damage to help evaluate and predict skin cancer risk. Accordingly, embodiments of the disclosure relate to a UV radiation biomarker panel that can serve as sensitive tool for UV damage assessment and risk prediction to facilitate skin cancer prevention and reduce skin cancer-related illness, death and health care costs.

In one embodiment, an assay is provided for evaluating the effect of ultraviolet radiation (UVR) on a tissue sample. The assay comprises a system to evaluate expression of a plurality of UVR-responsive biomarker genes in the tissue sample, wherein expression of one or more of the plurality of UVR-responsive biomarker genes is associated with exposure of the tissue sample to ultraviolet radiation. In one embodiment, the system is a gene array system to evaluate expression of the plurality of UVR-responsive biomarker genes. In another embodiment, the assay is a high-capacity screening assay configured to evaluate the expression of the plurality of UVR-responsive biomarker genes in a plurality of tissue samples.

In one embodiment, the plurality of UVR-responsive biomarker genes are those associated with at least one of skin damage due to UV exposure, cancer risk and cancer progression. In yet another embodiment, the plurality of UVR-responsive biomarker genes are those that are involved at least one of inflammation, cell growth and proliferation, DNA repair, and cancer pathogenesis. In yet a further embodiment, the plurality of UVR-responsive biomarker genes are those selected from the group consisting of CYP24A1, GJA5, SLAMF7 and ETV1.

In one embodiment, the tissue sample that is evaluated by the assay is a mammalian tissue sample. For example, in one embodiment, the tissue sample is a human tissue sample. As yet another example, in one embodiment, the tissue sample comprises human keratinocytes.

In one embodiment, the assay is capable of correlating the expression of each of the UVR-responsive biomarker genes with at least one of UV damage to the tissue sample and/or a disease state, such as via a gene expression profile correlation system to correlate.

In one embodiment, a method of evaluating ultraviolet damage to tissue comprises evaluating the expression of a plurality of UVR-responsive biomarker genes in a sample of the tissue, and determining whether the expression of one or more of the plurality of UVR-responsive biomarker genes is indicative of ultraviolet damage. For example, in one embodiment, the plurality of UVR-responsive biomarker genes are those associated with at least one of skin damage due to UV exposure, cancer risk and cancer progression. In yet another embodiment, the plurality of UVR-responsive biomarker genes are those selected from the group consisting of CYP24A1, GJA5, SLAMF7 and ETV1. In one embodiment, the expression of the plurality of UVR-responsive biomarker genes is evaluated via a high-capacity gene array screening system.

Accordingly to one embodiment, the tissue that is evaluated for UV damage is mammalian tissue. According to yet another embodiment, the tissue that is evaluated for UV damage is human tissue.

In one embodiment, a method of diagnosing skin cancer or predicting skin cancer risk in a subject comprises evaluating the expression of a plurality of UVR-responsive biomarker genes in a sample of the tissue, and determining whether the expression is indicative of skin cancer or skin cancer risk. For example, in one embodiment, the plurality of UVR-responsive biomarker genes are those selected from the group consisting of CYP24A1, GJA5, SLAMF7 and ETV1. In one embodiment, the subject is a mammalian subject. In yet another embodiment, the subject is a human subject.

In one embodiment, a method of evaluating a sunscreen formulation comprises applying the sunscreen formulation to a tissue sample, irradiating the tissue sample with ultraviolet radiation, evaluating the expression of a plurality of UVR-responsive biomarker genes in the tissue sample, and determining whether the expression of the plurality of UVR-responsive biomarker genes is indicative of efficacy of sunscreen formulation in providing a UV protective effect to the tissue sample.

One embodiment of the present disclosure is directed to providing UVR biomarkers having better reliability and accuracy. Accordingly, to obtain UVR biomarkers with better reliability and accuracy, a panel of UVR-responsive genes have been identified through comprehensive transcriptomic profiling studies. Functions of these carefully selected UVR biomarker genes span several biological pathways including inflammation, cell growth and proliferation, DNA repair, and cancer pathogenesis. The panel of genes has been subjected to rigorous validations by both bioinformatics and experimental approaches to confirm that their mRNA expressions are consistently responsive to UVR among different skin types. Furthermore, the UVR-induced mRNA expression changes in the biomarker genes persist long after UVR, highlighting their potential as reliable UVR biomarkers.

According to one embodiment, the UV biomarker panel can serve to set a new industrial standard in testing UVR-protective effects of sunscreen products in preventing cancer-inducing dose of sun damage. According to yet another embodiment, it can be used in clinical diagnosis to assist health care providers with a sensitive tool in assessing excessive sun exposure and skin cancer risk. In yet another embodiment, to facilitate industrial and clinical applications, a gene array system in a 96-well plate format is designed to allow simultaneous detections of the expression of the UVR biomarker genes from multiple samples. In one embodiment, the UVR biomarker panel together with the high capacity screening assay system may be capable of revolutionizing the assessment of sun damage and skin cancer risk predication to allow for early prevention and effective reduction of skin cancer-related illness, death, and health care costs.

Embodiments of the disclosure may involve (1) validation and optimization of the selection of biomarker genes for gene-array preparation; (2) development and optimization of a compact gene array system that can process multiple samples on the same array to achieve high screening capacity; and (2) development of algorithms to enable autonomous processing of gene expression data.

In one embodiment, a UVR biomarker panel is provided for monitoring sun damage and predicting skin cancer risk with a high level of sensitivity and accuracy. Associated analytical regents, test kits and diagnostic models for sun damage detection and cancer risk prediction can also be provided.

In one embodiment, the UVR biomarker panel can be applied in the sunscreen industry to evaluate the efficacy of sunscreen products in UVR protection and reducing sun exposure damage of the skin.

In one embodiment, the tissue and/or subject being evaluated is mammalian, such as preferably human. In other aspects of this embodiment, the tissue and or subject is that of a laboratory animal. In addition to humans, categories of mammals within the scope of aspects of the present disclosure include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

In one embodiment, methods and/or steps in methods described herein may be carried out in vitro. In other embodiments, the methods and/or steps in the methods described herein are carried out in vivo or ex vivo.

As used herein, in vitro refers to a process performed in an artificial environment created outside a living multicellular organism (e.g., a test tube or culture plate) used in experimental research to study a disease or process. As used herein, in vitro includes processes performed in intact cells growing in culture.

As used herein, in vivo means that which takes place inside an organism and more specifically to a process performed in or on the living tissue of a whole, living multicellular organism (animal), such as a mammal, as opposed to a partial or dead one.

As used herein, ex vivo refers to a process performed in an artificial environment outside the organism on living cells or tissue which are removed from an organism and subsequently returned to an organism.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

EXAMPLES

First Series of Experiments

Example 1

Materials and Methods

Human Keratinocyte Cultures, Human SCC and Normal Skin Tissues

Primary human keratinocytes were established from neonatal foreskins through the Columbia University Skin Disease Research Center tissue culture core facility. The protocol was exempt by our Institutional Review Board. Keratinocytes were isolated from separate individual neonatal foreskins (NO, N1, N2, and N6), and cells from each individual were maintained and analyzed separately for assessing individual variations. Keratinocytes were cultured in 154CF medium supplemented with human keratinocyte growth supplement (Life Technologies, Grand Island, N.Y.). Human SCC tumor tissues and matched normal skin tissues from two patients were obtained from the Molecular Pathology Shared Resource/Tissue Bank of the Herbert Irving Comprehensive Cancer Center of Columbia University under CUMC IRB protocol AAAB2667.

UVB Radiation

Keratinocytes were rinsed once with PBS and irradiated with UVB supplied by four FS20T12/UVB tubes (National Biological Corp., Beachwood, Ohio). The intensity of UVB lights was measured using an IL1400 radiometer connected to a SEL240/UVB-1/TD detector (International Light, Newburyport, Mass.). Cells were irradiated with a total dose of 10, 20, and 30 mJ/cm$^2$, respectively. Cells were collected at different times points after exposure including four hours or one, three, or 21 days as indicated.

RNA Isolation and RNA-Seq Analysis

Total RNA was isolated from cultured keratinocytes and human tissues using the RNeasy Kit (QIAGEN, Gaithersburg, Md.) and treated with DNase I (Life Technologies, Grand Island, N.Y.) according to the manufacturers' protocols. All RNA samples were subsequently analyzed using an RNA 6000 nano chip (Agilent Technologies, Wilmington, Del.) to confirm that the RNA integrity index was 8.0 or above. For RAN-Seq, 500 ng of total RNA from each sample was subjected to poly-A pull-down to enrich mRNAs for library preparation by using Illumina TruSeq RNA prep kit (Illumina, San Diego, Calif.). The resulting libraries were sequenced using Illumina HiSeq2000 at Columbia Genome Center. Samples were multiplexed in each lane, which yielded targeted number of paired-end 100 bp reads for each sample, as a fraction of 180 million reads for the whole lane. We used RTA (Illumina) for base calling and bcl2fastq (version 1.8.4, Illumina) for converting BCL to fastq format, coupled with adaptor trimming. The reads were mapped to the human reference genome (NCBI/build37.2) using Tophat (version 2.0.4). Relative gene expression levels were calculated using Cufflinks (version 2.0.2) with default settings. Differentially expressed genes (DEGs) under various UVR conditions were determined using the DESeq software package (Anders 2010), with a fold change cutoff set at >2 or <0.5 between irradiation and non-irradiated keratinocytes. Genes with FPKM values <10 were subjected to higher FC cutoffs to be selected in the final DEG list (details available upon request). A False Discovery rate (FDR)<0.05 was used to control for false discoveries.

Bioinformatics and Statistical Analyses

DEG lists were used in principal component analysis (PCA) to characterize the variations in transcriptomic responses to different UVR conditions among the keratinocyte lines. To uncover pathways that were most significantly affected by UVR, we performed pathway analysis using DAVID to identify which biological pathways the differentially expressed genes were enriched in. Gene enrichment analysis (GSEA) was performed to determine the overlap between UVR signature genes and gene sets that were dysregulated in different human malignancies. Paired t-test was used to identify genes displaying time-dependent UVR responses from Day 1 to Day 3 following exposure. To identifying genes manifesting dose-dependent changes in response to UVR, we constructed a linear regression model using UVR dosage as an independent variable and gene expression as a dependent variable for each gene in the same keratinocyte line and at the same time point. We then performed the same analysis for all three keratinocyte lines (N0, N1, and N2) and at both time points (Day 1 and 3), which generated six expression models for each gene. In each model, a low coefficient p-value ($p<0.05$) indicated a significant association between UVR dosage and gene expression. To evaluate the overall effects of the various UVR dosage on the expression of a specific gene, we integrated the multiple p-values from every regression analysis for that gene using Fisher's Method. P-values from the above analyses were FDR-corrected. To obtain cancer-specific gene signatures for various human malignancies, we retrieved and selected RNA-Seq data sets from the TOGA database that were available for both primary tumor cases and matched normal control tissues from same patient for each tumor type. We used DESeq package to normalize the raw counts and determine genes that were differentially expressed between each primary tumor and matched normal control tissue to obtain dysregulated gene sets for each tumor type. To identify genes that are critical to skin cancer cell proliferation or survival, we queried the Achilles database with 67 of the UVR signature genes that were upregulated by UVR. (Cowley 2014) Genes were considered essential to skin cancer cell survival if their corresponding shRNAs became depleted after 40 days or 16 population doublings following shRNA infection. Normalized shRNA depletion scores were downloaded from the "cBOTv8_sbsv3_allreps_log.gct2" file in Achilles database. For multiple shRNAs targeting the same gene, we selected the ones whose depletion scores were consistent across all cancer cell lines and then took the median value as the final depletion score for each shRNA. All statistical analyses were performed using R.

Example 2

Transcriptomic Responses to Different UVR Conditions

In addition to its mutagenic effect, UVR has been shown to cause transcriptomic instability affecting thousands of genes. To fully characterize UVR-induced transcriptomic changes, we took advantage of the recent advances in RNA-Seq to profile UVR-induced kinetic changes in human primary keratinocytes exposed to different UVR conditions (Table 1). We used keratinocytes isolated from four individual neonatal foreskins to generate UVR-induced differentially expressed gene (DEG) lists in response to each of the UVR conditions (Table 1). Together with four DEG lists representing transcriptomic profiles at four hours after exposure, we performed principle component analysis (PCA) to differentiate the DEG profiles under various UVR conditions. As shown in the PCA plot (FIG. 1A), DEG profiles from Day 1 and 3 groups, but not the 4 hour group, demonstrated great similarities with each other in the first principle component (PC1). Along the second principle component (PC2) axis, however, the range of differences within the Day 3 DEG group appeared smaller than that of the Day 1 DEG group, demonstrating a clear time-dependent transcriptomic effect of UVR that became less differentiated among different UVR conditions 3 days after exposure.

To uncover the biological pathways that were mostly affected by UVR, we took the average of the fold change (FC) of each gene between irradiated and non-irradiated cells from the 19 DEG lists (Table 1). Using a FC cutoff of 2, we obtained a total of 531 genes that were up-regulated ($FC>2$) and 610 genes that were down-regulated ($FC<0.5$) in response to different UVR conditions (Table 2 and Table 3). We performed DAVID pathway analysis to categorize the functions of the up-regulated genes and down-regulated genes, respectively, which revealed multiple pathways that were significantly modulated by UVR. The down-regulated genes were significantly enriched in the following top four biological pathways: cell cycle regulation (83 genes), chromosome structure (19 genes), DNA damage response (59 genes) and microtubule organization (23 genes); whereas the up-regulated genes were largely enriched in pathways such as apoptosis (33 genes), defense inflammatory response (43 genes), ectoderm epithelium development (36 genes), cell adhesion (4 genes) and leukocyte activation (9 genes) (FIG. 1B).

TABLE 1

Keratinocyte lines and experimental UVR conditions

| | | UVR conditions | | | | | |
|---|---|---|---|---|---|---|---|
| | | 10 $mJ/cm^2$ 24 h | 20 $mJ/cm^2$ 24 h | 30 $mJ/cm^2$ 24 h | 10 $mJ/cm^2$ 72 h | 20 $mJ/cm^2$ 72 h | 30 $mJ/cm^2$ 72 h |
| Keratinocyte lines | N0 | 1 | 2 | 3 | 4 | 5 | 6 |
| | N1 | 7 | 8 | 9 | 10 | 11 | 12 |
| | N2 | 13 | 14 | 15 | 16 | 17 | 18 |
| | N3 | | | | | | 19 |

TABLE 2

Genes up-regulated by UVR

| Gene ID | Log2FC |
|---|---|
| A2ML1 | 1.25542 |
| A4GALT | 1.217168 |
| ABCA12 | 1.377908 |
| ABCD1 | 1.252331 |
| ABHD4 | 1.15769 |
| ABLIM3 | 1.065562 |
| ACAP1 | 1.359902 |
| ACBD4 | 1.075352 |
| ACER2 | 2.006333 |
| ACTA2 | 1.169663 |
| ADAMTS13 | 1.111708 |
| ADAMTS7 | 1.803072 |
| ADAMTSL4 | 1.579834 |
| ADCK3 | 1.407755 |
| ADH6 | 1.037455 |
| ADHFE1 | 1.308802 |
| ADSSL1 | 1.567365 |
| AIFM3 | 1.051368 |
| AIM1L | 1.309328 |
| AKR1B10 | 1.680432 |
| AKR1C1 | 1.734541 |
| AKR1C2 | 1.63357 |
| AKR1C3 | 1.442466 |
| ALDH3B2 | 1.885289 |
| ALOX12B | 1.627145 |
| ALOX15B | 1.148359 |
| ANKRD22 | 1.505822 |
| ANKRD29 | 1.004008 |
| APOE | 1.10496 |
| ARHGAP30 | 2.227763 |
| ARNT2 | 2.347534 |
| ARRDC4 | 1.377681 |
| ASPRV1 | 2.393802 |
| ATF3 | 2.600626 |
| ATP12A | 1.440183 |
| AVPI1 | 1.283781 |
| B3GALT4 | 1.300773 |
| B3GNT3 | 1.049928 |
| BBC3 | 1.612703 |
| BCL2L1 | 1.077692 |

TABLE 2-continued

Genes up-regulated by UVR

| Gene ID | Log2FC |
|---|---|
| BCL6 | 1.022801 |
| BIK | 1.899355 |
| BIRC3 | 1.411982 |
| BLNK | 2.166166 |
| BMF | 2.369338 |
| BNIP3L | 1.036609 |
| BST2 | 1.416924 |
| BTBD19 | 1.135608 |
| BTG1 | 1.148244 |
| BTG2 | 1.403243 |
| C10orf99 | 2.924011 |
| C11orf35 | 1.369906 |
| C11orf9 | 1.682084 |
| C16orf5 | 1.006965 |
| C17orf103 | 1.565166 |
| C18orf56 | 1.11554 |
| C19orf46 | 1.466501 |
| C1orf126 | 1.008004 |
| C1orf38 | 1.298954 |
| C1orf51 | 1.552331 |
| C1orf74 | 1.732929 |
| C1orf88 | 1.324512 |
| C20orf46 | 1.04507 |
| C5orf41 | 1.546868 |
| C6orf138 | 1.094879 |
| C7orf10 | 1.941839 |
| C7orf53 | 1.249614 |
| C9orf7 | 1.060832 |
| CA2 | 1.243123 |
| CALML3 | 1.255207 |
| CALML5 | 2.024878 |
| CAPNS2 | 1.210126 |
| CARD14 | 1.278924 |
| CARD18 | 2.472437 |
| CASP9 | 1.091866 |
| CBX7 | 1.169991 |
| CCDC11 | 1.24824 |
| CCDC64B | 1.433373 |
| CCK | 1.062617 |
| CCL20 | 1.568576 |
| CD55 | 1.028517 |
| CD68 | 1.471241 |
| CD74 | 1.002605 |
| CDKN1A | 1.898547 |
| CDKN1C | 1.344886 |
| CDKN2B | 1.337026 |
| CDKN2D | 1.103006 |
| CDSN | 2.193489 |
| CEACAM1 | 1.521198 |
| CEBPA | 1.068886 |
| CEL | 1.833995 |
| CES3 | 1.495162 |
| CES4A | 1.145926 |
| CFB | 1.525458 |
| CGN | 1.243352 |
| CHI3L2 | 2.22442 |
| CHST2 | 1.153737 |
| CITED2 | 1.362391 |
| CLCF1 | 1.746694 |
| CLDN1 | 2.164861 |
| CLDN23 | 1.949484 |
| CLDN4 | 3.387876 |
| CLDN7 | 1.756154 |
| CLEC2B | 1.823128 |
| CLIC3 | 1.327201 |
| CLU | 1.438944 |
| CNFN | 2.155499 |
| COX6B2 | 1.34408 |
| CPT1C | 1.277061 |
| CRB3 | 1.066881 |
| CRCT1 | 3.196832 |
| CRISPLD2 | 2.63943 |
| CRYAB | 2.080253 |
| CSF1 | 1.150493 |
| CSF3 | 1.528244 |
| CST6 | 3.096074 |
| CTSS | 1.384918 |
| CUL9 | 1.146301 |
| CYFIP2 | 2.012293 |
| CYGB | 1.278952 |
| CYP2S1 | 1.111609 |
| CYP3A5 | 2.134077 |
| DAPK1 | 2.489445 |
| DBNDD1 | 1.697917 |
| DBP | 1.548785 |
| DCN | 1.917867 |
| DEFB1 | 4.538491 |
| DENND1C | 1.052741 |
| DGAT2 | 1.066686 |
| DHDH | 1.977426 |
| DHRS3 | 1.150886 |
| DKFZp434J0226 | 1.581589 |
| DPP4 | 1.635675 |
| DQX1 | 1.282541 |
| DUSP10 | 2.217671 |
| DYRK1B | 1.133527 |
| EDA2R | 1.650437 |
| EGR3 | 1.055599 |
| ELFN2 | 1.454605 |
| ENO2 | 1.176432 |
| ENTPD3 | 1.13432 |
| EPHB2 | 1.0814 |
| EPHB3 | 1.28144 |
| EPPK1 | 1.03793 |
| ERBB3 | 1.176234 |
| ESPN | 1.898346 |
| ETV7 | 1.992978 |
| FAM131C | 1.195041 |
| FAM13C | 1.660195 |
| FAM198B | 1.546092 |
| FAM43A | 2.281964 |
| FAM46A | 1.142838 |
| FAM84A | 1.217675 |
| FAM86HP | 1.398758 |
| FBXO32 | 1.762987 |
| FDXR | 1.123815 |
| FGF11 | 1.057493 |
| FLJ32255 | 1.396227 |
| FLJ35776 | 1.045777 |
| FLJ43663 | 1.505095 |
| FLJ45831 | 1.688516 |
| FLNC | 1.840758 |
| FN3K | 1.042252 |
| FOLR3 | 1.453421 |
| FTH1 | 1.02617 |
| FTL | 1.293257 |
| FUT2 | 1.130622 |
| FUT3 | 1.400397 |
| FXYD3 | 1.235707 |
| G0S2 | 1.507978 |
| GABARAPL1 | 1.12635 |
| GALK1 | 1.028271 |
| GAMT | 1.499196 |
| GBP2 | 2.981328 |
| GDA | 1.668244 |
| GDF15 | 4.934651 |
| GGT1 | 1.76415 |
| GGT6 | 2.012062 |
| GIPR | 1.443944 |
| GJA5 | 1.128834 |
| GJB4 | 1.442723 |
| GLRX | 1.411782 |
| GLS2 | 1.635732 |
| GPNMB | 1.547934 |
| GPR172B | 2.315739 |
| GPR37 | 1.273549 |
| GPRASP1 | 1.081898 |
| GPRC5A | 3.036593 |
| GRB7 | 1.812811 |
| GREB1 | 3.918492 |
| GRHL1 | 1.549886 |
| GRHL3 | 2.137244 |

TABLE 2-continued

Genes up-regulated by UVR

| Gene ID | Log2FC |
|---|---|
| GRIN3B | 1.04264 |
| GRIP2 | 1.741655 |
| GSDMA | 1.531598 |
| GTF2IP1 | 1.31404 |
| GUCA1B | 1.103181 |
| H1F0 | 1.009822 |
| H1FX-AS1 | 1.000064 |
| HAP1 | 2.66275 |
| HAPLN3 | 1.002183 |
| HBEGF | 1.037813 |
| HBP1 | 1.070321 |
| HCAR2 | 2.227049 |
| HCAR3 | 2.061033 |
| HCP5 | 1.022373 |
| HDAC5 | 1.191311 |
| HDAC9 | 1.014098 |
| HEPHL1 | 1.084285 |
| HES2 | 1.815118 |
| HIST1H1C | 2.570588 |
| HIST1H2AC | 1.751416 |
| HIST1H2BD | 2.723667 |
| HIST1H2BK | 1.243929 |
| HIST2H2BE | 1.850329 |
| HIST3H2A | 1.005484 |
| HLA-G | 2.460471 |
| HMOX1 | 2.320076 |
| HSD17B14 | 1.463513 |
| HSD17B2 | 1.779269 |
| HSD3B7 | 1.356109 |
| HSH2D | 1.030704 |
| HSPB8 | 2.738695 |
| ICAM1 | 2.087607 |
| ICAM4 | 1.355522 |
| ID2 | 1.7539 |
| IDUA | 1.182603 |
| IFI27 | 1.601052 |
| IFIT2 | 1.077206 |
| IGFBP3 | 1.96108 |
| IGFL3 | 1.932189 |
| IL1B | 1.223292 |
| IL1R2 | 2.283708 |
| IL1RN | 1.278581 |
| IL23A | 1.378554 |
| IL32 | 1.122006 |
| IL33 | 1.109746 |
| IL36RN | 2.089587 |
| IL8 | 1.751882 |
| INPP5D | 1.925148 |
| INPP5J | 1.016762 |
| IRAK2 | 1.116631 |
| IRF5 | 1.327517 |
| IRF6 | 1.395184 |
| ISG20 | 1.350179 |
| ISYNA1 | 1.381921 |
| ITIH4 | 1.029668 |
| ITPKC | 1.126402 |
| IVL | 2.375886 |
| KCNN4 | 1.802118 |
| KCTD11 | 1.081291 |
| KIAA1257 | 1.865952 |
| KIAA1370 | 1.146223 |
| KLHDC9 | 1.432303 |
| KLHL24 | 1.889937 |
| KLK10 | 1.414561 |
| KLK11 | 1.551882 |
| KLK5 | 1.255347 |
| KLK7 | 1.405181 |
| KLRG2 | 1.233281 |
| KRT13 | 4.582385 |
| KRT15 | 2.227083 |
| KRT16 | 1.445009 |
| KRT19 | 1.292513 |
| KRT23 | 2.654857 |
| KRT34 | 2.056054 |
| KRT37 | 2.786469 |
| KRT42P | 1.383759 |
| KRT6B | 1.218162 |
| KRT7 | 1.20472 |
| KRT75 | 1.204212 |
| KRT80 | 2.425273 |
| KRTDAP | 1.404801 |
| KYNU | 1.234901 |
| LACC1 | 1.348361 |
| LBH | 1.964427 |
| LCE1B | 2.863596 |
| LCE1C | 1.5978 |
| LCN2 | 1.410005 |
| LIF | 2.020803 |
| LINC00086 | 2.475568 |
| LMO7 | 1.453974 |
| LOC100049716 | 1.166231 |
| LOC100129781 | 1.088847 |
| LOC100131096 | 1.015925 |
| LOC100131564 | 1.109901 |
| LOC100132909 | 1.081642 |
| LOC100133190 | 1.059472 |
| LOC100287177 | 1.060091 |
| LOC100505623 | 1.290074 |
| LOC100505974 | 1.072712 |
| LOC100506119 | 1.199105 |
| LOC100506377 | 1.931858 |
| LOC100506538 | 1.582621 |
| LOC100506746 | 1.093062 |
| LOC100507429 | 1.577794 |
| LOC100507452 | 1.034674 |
| LOC100507656 | 1.387791 |
| LOC151475 | 2.864213 |
| LOC151534 | 1.798543 |
| LOC284080 | 1.116795 |
| LOC284440 | 1.232691 |
| LOC284837 | 2.507131 |
| LOC441869 | 1.405387 |
| LOC554223 | 1.05486 |
| LOC646471 | 1.010308 |
| LOC728975 | 1.150382 |
| LOC730755 | 1.127336 |
| LY6D | 2.375439 |
| LY6G6C | 1.478579 |
| LYNX1 | 1.569974 |
| LYPD3 | 1.202858 |
| LYPD5 | 1.938955 |
| MAFB | 1.976484 |
| MAP1LC3A | 1.524844 |
| MAP3K8 | 1.266091 |
| MAPK8IP2 | 1.267615 |
| MCHR1 | 2.376182 |
| MDM2 | 1.857866 |
| MEG3 | 1.680548 |
| METRNL | 1.850228 |
| MEX3B | 1.293473 |
| MIR21 | 1.056403 |
| MLPH | 1.048951 |
| MME | 1.279362 |
| MNT | 1.093418 |
| MUC1 | 1.323749 |
| MXD1 | 1.221816 |
| MXD4 | 1.119169 |
| MXI1 | 1.012704 |
| MYBPHL | 2.469553 |
| MYH16 | 1.669449 |
| MYO15B | 1.769726 |
| N4BP2L1 | 1.302932 |
| NCCRP1 | 2.25184 |
| NCF2 | 1.956338 |
| NDRG4 | 1.724837 |
| NEAT1 | 1.17292 |
| NFATC4 | 1.144891 |
| NFKBIA | 1.085284 |
| NFKBIZ | 1.055574 |
| NHLH2 | 1.783285 |
| NINJ1 | 1.360009 |
| NIPAL4 | 1.035101 |

TABLE 2-continued

Genes up-regulated by UVR

| Gene ID | Log2FC |
|---|---|
| NLRP10 | 2.908381 |
| NOD2 | 1.045928 |
| NOTCH3 | 2.10179 |
| NR1D1 | 1.830782 |
| NR1D2 | 1.034866 |
| NR4A1 | 1.502722 |
| NR4A2 | 1.09004 |
| NUPR1 | 1.436536 |
| OCLN | 1.834442 |
| OVGP1 | 1.381053 |
| OVOL1 | 2.085033 |
| P4HTM | 1.543172 |
| PADI1 | 1.763089 |
| PAPL | 1.978976 |
| PCDH1 | 2.520425 |
| PDE6B | 1.230008 |
| PGPEP1 | 1.267001 |
| PHLDB3 | 1.019073 |
| PHYHIP | 1.46292 |
| PI3 | 2.404414 |
| PIDD | 1.246663 |
| PIK3IP1 | 1.63279 |
| PKIB | 1.88435 |
| PLA2G4C | 1.366493 |
| PLA2G4D | 1.768802 |
| PLA2G4E | 1.233771 |
| PLAC2 | 1.196007 |
| PLAUR | 1.160952 |
| PLEKHG1 | 1.058571 |
| PLEKHG6 | 1.612271 |
| PLIN4 | 2.008771 |
| PNLIPRP3 | 1.06203 |
| PNMAL1 | 1.138815 |
| PNRC1 | 1.363591 |
| POU2F3 | 1.906488 |
| POU3F1 | 1.472181 |
| PPL | 1.079871 |
| PPP1R15A | 1.250187 |
| PPP1R3B | 1.200822 |
| PRDM1 | 1.492528 |
| PRICKLE4 | 1.141436 |
| PRODH | 1.239592 |
| PROM2 | 1.239982 |
| ProSAPiP1 | 1.008596 |
| PRSS22 | 3.207114 |
| PRSS8 | 1.194038 |
| PSORS1C1 | 1.553438 |
| PTGES | 1.511422 |
| PTGS2 | 1.301506 |
| PVRL4 | 3.274905 |
| QPCT | 1.121274 |
| RAB11FIP1 | 1.050886 |
| RAET1G | 1.355114 |
| RASSF5 | 1.541771 |
| REEP6 | 1.077737 |
| RET | 1.243314 |
| RGAG4 | 1.507274 |
| RGS16 | 2.736892 |
| RGS2 | 1.778959 |
| RHBDL1 | 1.204067 |
| RHCG | 2.079265 |
| RHPN1 | 1.365829 |
| RIBC1 | 1.098573 |
| RINL | 1.033176 |
| RNASE7 | 1.870734 |
| RND2 | 1.440745 |
| RNF208 | 1.265198 |
| RORA | 1.140093 |
| RRAD | 3.850695 |
| RRM2B | 1.324419 |
| RSAD2 | 1.549139 |
| RUNDC3A | 1.48569 |
| RYR1 | 1.065997 |
| S100A4 | 1.430196 |
| S100A6 | 1.054154 |
| S100A8 | 2.129619 |
| SAA1 | 1.335856 |
| SALL4 | 2.057745 |
| SAMD10 | 1.014837 |
| SBK1 | 2.558557 |
| SBSN | 1.878689 |
| SCNN1A | 1.524209 |
| SDPR | 1.22298 |
| SELPLG | 1.687573 |
| SEMA3B | 2.411019 |
| SEMA3G | 1.572456 |
| SERPINB1 | 1.159593 |
| SERPINB2 | 1.49504 |
| SERPINB3 | 1.529827 |
| SERPINB7 | 1.343932 |
| SERTAD1 | 1.03668 |
| SESN1 | 1.171176 |
| SGPP2 | 1.075454 |
| SIK1 | 1.048194 |
| SIRPB2 | 1.315647 |
| SLAMF7 | 2.122482 |
| SLC28A3 | 1.767182 |
| SLC2A12 | 1.185052 |
| SLC44A3 | 1.096887 |
| SLC46A1 | 1.177566 |
| SLC7A4 | 1.156152 |
| SLPI | 2.205451 |
| SMOC1 | 1.596494 |
| SNCG | 1.231876 |
| SORT1 | 1.427147 |
| SPATA18 | 1.077252 |
| SPINK6 | 1.288906 |
| SPNS2 | 1.783244 |
| SPOCD1 | 1.028304 |
| SPON2 | 3.073135 |
| SPRR1A | 1.79158 |
| SPRR1B | 1.458382 |
| SPRR2A | 1.281665 |
| SPRR2D | 1.021259 |
| SPRR2E | 1.628479 |
| SPRR3 | 2.813864 |
| SQSTM1 | 1.526918 |
| STEAP4 | 4.22635 |
| SULT1A1 | 1.332854 |
| SULT2B1 | 1.729219 |
| SYNGR3 | 1.134232 |
| SYTL2 | 1.420285 |
| TACSTD2 | 1.167671 |
| TCP11L2 | 1.288639 |
| TGFB2 | 1.111166 |
| TGM1 | 1.556176 |
| THBD | 1.570713 |
| TIMP2 | 1.624976 |
| TLCD2 | 1.203551 |
| TLR2 | 1.209706 |
| TM7SF2 | 1.094312 |
| TMEM125 | 1.769122 |
| TMEM184A | 1.403734 |
| TMEM27 | 2.26327 |
| TMEM38A | 1.428279 |
| TMEM45B | 1.329869 |
| TMEM61 | 1.417963 |
| TMEM86A | 1.280883 |
| TMEM91 | 1.277979 |
| TMPRSS11D | 1.097904 |
| TMPRSS13 | 2.538018 |
| TMPRSS4 | 1.673327 |
| TNF | 1.380011 |
| TNFAIP2 | 2.133214 |
| TNFAIP8L3 | 1.078872 |
| TNFRSF10C | 4.084906 |
| TNFRSF14 | 1.154539 |
| TNFSF4 | 1.328395 |
| TOB1 | 1.129999 |
| TP53INP1 | 1.898305 |
| TP53INP2 | 1.709985 |
| TPPP | 1.126332 |

TABLE 2-continued

Genes up-regulated by UVR

| Gene ID | Log2FC |
|---|---|
| TRAF1 | 1.270284 |
| TRAF3IP3 | 1.885624 |
| TREM2 | 1.406591 |
| TRIM17 | 1.097686 |
| TRIM22 | 1.107816 |
| TSPAN1 | 1.043978 |
| TSPAN10 | 1.145679 |
| TTC39A | 1.513684 |
| TTC9 | 1.775748 |
| TTLL3 | 1.07677 |
| TXNIP | 1.324999 |
| UCA1 | 3.144775 |
| ULBP1 | 1.718077 |
| ULK1 | 1.155636 |
| UNC13D | 1.284158 |
| VAMP5 | 1.10333 |
| VASN | 1.070314 |
| VGLL3 | 1.526916 |
| VNN1 | 1.585207 |
| VWCE | 2.339601 |
| WDR63 | 1.100921 |
| WFDC5 | 1.623134 |
| YPEL2 | 1.093046 |
| YPEL3 | 1.333902 |
| YPEL4 | 2.050039 |
| ZFHX2 | 1.14507 |
| ZFYVE1 | 1.004115 |
| ZNF185 | 1.058878 |
| ZNF425 | 1.493712 |
| ZNF432 | 1.264009 |
| ZNF610 | 1.214798 |
| ZNF702P | 1.114955 |
| ZNF750 | 1.98419 |
| ZNF763 | 1.068978 |
| ZNF812 | 1.677638 |

TABLE 3

Genes down-regulated by UVR

| Gene ID | Log2FC |
|---|---|
| ABCC4 | -1.348205778 |
| ABI3BP | -1.592845354 |
| ADAMTSL1 | -3.057818112 |
| AGTPBP1 | -1.059225614 |
| AKAP6 | -1.065270643 |
| AKAP7 | -1.191007938 |
| AKT3 | -1.063141722 |
| ALDH1L2 | -1.71329721 |
| ALG14 | -1.390158117 |
| ALMS1 | -1.39725398 |
| ANK2 | -2.852547236 |
| ANKRD44 | -3.201509809 |
| ANLN | -2.074462024 |
| ANO1 | -1.455452126 |
| ANXA6 | -1.214603625 |
| APBA1 | -1.03839454 |
| APCDD1 | -1.068852998 |
| APLN | -1.995875214 |
| ARHGAP11A | -1.932775855 |
| ARHGAP11B | -1.97626487 |
| ARHGAP18 | -1.090237869 |
| ARHGAP19 | -1.34032156 |
| ARHGAP33 | -1.316757909 |
| ARSB | -1.490168103 |
| ASF1B | -1.507991707 |
| ASNS | -1.325921219 |
| ASPM | -2.485501797 |
| ATAD2 | -1.092034263 |
| ATAD5 | -1.198810998 |
| ATG10 | -1.012583207 |
| AURKA | -1.605879285 |

TABLE 3-continued

Genes down-regulated by UVR

| Gene ID | Log2FC |
|---|---|
| AURKB | -2.266234804 |
| B3GALTL | -1.098025255 |
| BARD1 | -1.245055616 |
| BBS9 | -1.716979874 |
| BCAS3 | -1.500580847 |
| BCAT1 | -1.262972667 |
| BCL2 | -1.345519919 |
| BEND6 | -1.554214214 |
| BIRC5 | -2.468776552 |
| BLM | -1.833991479 |
| BORA | -1.11351262 |
| BRCA1 | -1.433568205 |
| BRCA2 | -1.738870791 |
| BRIP1 | -1.365404961 |
| BUB1 | -2.232101679 |
| BUB1B | -2.463047443 |
| C11orf82 | -1.734657367 |
| C12orf26 | -1.02533073 |
| C12orf48 | -1.731440454 |
| C12orf55 | -1.155331766 |
| C14orf49 | -1.046892915 |
| C14orf80 | -1.158411353 |
| C15orf42 | -1.43469073 |
| C16orf59 | -1.251575133 |
| C1orf112 | -1.026418432 |
| C21orf58 | -1.347413053 |
| C3orf26 | -1.633777304 |
| C4orf21 | -1.638019979 |
| C5 | -1.896229619 |
| C9orf100 | -1.416508411 |
| C9orf140 | -1.512229 |
| C9orf93 | -3.645734034 |
| CADPS2 | -2.749447365 |
| CAMKMT | -1.560519775 |
| CASC2 | -1.210566387 |
| CASC5 | -2.254998502 |
| CBS | -1.047490252 |
| CCBE1 | -1.49186818 |
| CCDC109B | -1.008132116 |
| CCDC150 | -1.777877107 |
| CCDC152 | -1.563498921 |
| CCDC18 | -1.539219671 |
| CCDC3 | -2.188282435 |
| CCNA2 | -2.040850548 |
| CCNB1 | -1.992477017 |
| CCNB2 | -2.023197257 |
| CCNE2 | -1.166174946 |
| CCNF | -1.319421617 |
| CDC20 | -2.788887669 |
| CDC25A | -1.345444577 |
| CDC25C | -1.941854577 |
| CDC45 | -1.66938146 |
| CDC6 | -1.746559274 |
| CDC7 | -1.022925655 |
| CDCA2 | -1.900385914 |
| CDCA3 | -2.659044568 |
| CDCA5 | -1.747593013 |
| CDCA7 | -1.343204821 |
| CDCA8 | -1.959093261 |
| CDH4 | -2.389925028 |
| CDK1 | -1.949360908 |
| CDK14 | -1.182597074 |
| CDKAL1 | -1.326316704 |
| CDKN2C | -1.321626434 |
| CDKN3 | -2.415696295 |
| CDON | -1.278358612 |
| CDT1 | -1.295120529 |
| CENPA | -2.730714266 |
| CENPE | -1.89935139 |
| CENPF | -2.568066958 |
| CENPH | -1.270674947 |
| CENPI | -1.767622737 |
| CENPJ | -1.102370738 |
| CENPK | -1.271103299 |
| CENPM | -1.567908583 |
| CENPN | -1.330259855 |

TABLE 3-continued

Genes down-regulated by UVR

| Gene ID | Log2FC |
|---|---|
| CENPO | −1.394874643 |
| CENPW | −1.348316188 |
| CEP112 | −1.785492351 |
| CEP128 | −1.931644843 |
| CEP170P1 | −3.902232714 |
| CEP55 | −2.535959714 |
| CHAF1A | −1.060713699 |
| CHEK1 | −1.204412215 |
| CHRNA5 | −1.310278551 |
| CHSY3 | −2.63674892 |
| CIT | −2.093026219 |
| CKAP2L | −2.259036313 |
| CKS1B | −1.089031731 |
| CLDN11 | −1.745869165 |
| CLMP | −2.630409593 |
| CLSPN | −1.755066048 |
| CMTM1 | −1.092242876 |
| CNTLN | −1.002235788 |
| CNTN1 | −1.717727031 |
| CNTNAP3 | −1.50024013 |
| COL12A1 | −1.225388115 |
| COL18A1 | −1.039211617 |
| COL24A1 | −1.275030048 |
| COL4A1 | −1.469924365 |
| COL4A2 | −1.669276381 |
| COL4A4 | −1.048165114 |
| COL5A1 | −1.270708967 |
| COL8A1 | −1.928088788 |
| COMMD1 | −1.133528646 |
| COMMD10 | −1.332882925 |
| CPS1 | −1.70577865 |
| CREB5 | −1.013904928 |
| CRELD2 | −1.101683675 |
| CSRNP3 | −1.459413081 |
| CTNNAL1 | −1.404403365 |
| CYP39A1 | −1.023008589 |
| DBF4 | −1.254245876 |
| DBF4B | −1.335142658 |
| DCDC2 | −1.495206045 |
| DCHS1 | −1.786705555 |
| DDX12P | −1.054548291 |
| DENND1A | −1.056858676 |
| DEPDC1 | −2.480768329 |
| DEPDC1B | −1.167668186 |
| DERL3 | −2.51482921 |
| DHFR | −1.297735908 |
| DIAPH2 | −1.696949962 |
| DIAPH3 | −2.033597387 |
| DLEU1 | −1.121028106 |
| DLEU2 | −2.107581325 |
| DLGAP5 | −2.608879588 |
| DLL1 | −1.015920318 |
| DMC1 | −3.630542564 |
| DNAH5 | −1.37639111 |
| DOCK10 | −1.918039738 |
| DOCK11 | −1.395693649 |
| DOCK4 | −1.143979182 |
| DPY19L2 | −1.056133483 |
| DPYD | −3.389239421 |
| DPYSL3 | −1.926485306 |
| DRP2 | −2.641906925 |
| DSCAM | −1.906670101 |
| DSCC1 | −1.403031606 |
| DTL | −1.948891786 |
| DTWD2 | −1.523560971 |
| DUSP9 | −1.171136132 |
| DYNC2H1 | −1.083013559 |
| DZIP3 | −1.080806672 |
| E2F1 | −1.637960738 |
| E2F2 | −1.587033082 |
| E2F8 | −1.073325681 |
| EDA | −1.827607348 |
| EDNRA | −1.659792405 |
| EFCAB11 | −1.584503864 |
| EFCAB2 | −1.527976301 |
| EFHC2 | −1.933530011 |
| ELAVL2 | −1.125514972 |
| ELOVL6 | −1.188535907 |
| ELP4 | −1.033572654 |
| EME1 | −1.532128786 |
| ENOX1 | −2.429551313 |
| EPB41L2 | −1.070473848 |
| ERCC6L | −1.837917859 |
| ESCO2 | −1.704405316 |
| ESPL1 | −1.810339548 |
| ETV1 | −1.384595787 |
| EXO1 | −2.035852802 |
| EXOC4 | −1.386101999 |
| EXTL2 | −1.239584151 |
| FAAH2 | −1.104705621 |
| FAF1 | −1.009982162 |
| FAM111B | −2.120125967 |
| FAM132B | −1.187212606 |
| FAM151B | −1.125962764 |
| FAM167A | −1.03677525 |
| FAM172A | −1.639239582 |
| FAM54A | −1.308473296 |
| FAM64A | −2.300111494 |
| FAM72A | −2.02193515 |
| FAM72B | −2.376888348 |
| FAM72D | −2.569570317 |
| FAM83D | −1.9457666 |
| FANCA | −1.30500965 |
| FANCB | −1.681934488 |
| FANCC | −1.226225604 |
| FANCD2 | −1.605305539 |
| FANCI | −1.236564911 |
| FAR2 | −1.708513767 |
| FARS2 | −1.344824882 |
| FBN2 | −1.282186621 |
| FBXL17 | −1.373090742 |
| FBXL7 | −2.52127296 |
| FBXO43 | −2.669021178 |
| FBXO5 | −1.501898367 |
| FEN1 | −1.059637367 |
| FGFBP1 | −1.649445744 |
| FGGY | −1.201858562 |
| FHIT | −2.966326239 |
| FIGN | −1.270062012 |
| FKBP11 | −1.262078361 |
| FOXD2 | −1.119795421 |
| FOXM1 | −2.05641668 |
| FOXP2 | −1.900599816 |
| FRAS1 | −1.154333269 |
| FUT4 | −1.003805317 |
| FUT8 | −1.067042768 |
| GALNT10 | −1.185419938 |
| GALNTL4 | −1.125279056 |
| GAS2L3 | −2.204825541 |
| GHR | −1.168281527 |
| GINS1 | −1.262554478 |
| GINS2 | −1.836989185 |
| GINS4 | −1.304293072 |
| GIPC2 | −1.366213219 |
| GJB2 | −1.157268298 |
| GLI1 | −1.607809436 |
| GLT8D2 | −1.021420114 |
| GMDS | −1.894237011 |
| GNB3 | −1.024028547 |
| GNG11 | −1.308698968 |
| GNG2 | −1.267535939 |
| GPC6 | −3.413041607 |
| GPHN | −1.639685734 |
| GPR113 | −1.006074874 |
| GPR39 | −1.182345041 |
| GPR63 | −1.082603164 |
| GPSM2 | −1.114318389 |
| GRB14 | −1.016641502 |
| GREB1L | −1.343457163 |
| GRIA1 | −3.531086354 |
| GRIP1 | −2.0507268 |
| GSG2 | −1.568691237 |

TABLE 3-continued

Genes down-regulated by UVR

| Gene ID | Log2FC |
| --- | --- |
| GTDC1 | −1.532315383 |
| GTSE1 | −2.383747263 |
| H2AFX | −1.343555024 |
| HAUS8 | −1.092972486 |
| HELLS | −1.088366116 |
| HIST1H2BH | −1.024808608 |
| HJURP | −2.4592233 |
| HMCN1 | −2.204217467 |
| HMGB2 | −1.263166086 |
| HMGCS1 | −1.182070599 |
| HMMR | −2.404579608 |
| HNRNPA3P1 | −1.036139918 |
| HPDL | −1.042909973 |
| HS6ST2 | −1.493151016 |
| HSP90B1 | −1.544477225 |
| HSP90B3P | −1.317944538 |
| HSPA5 | −1.420064786 |
| HYOU1 | −1.068804209 |
| IL7R | −1.477457922 |
| IMMP2L | −1.066160828 |
| INCENP | −1.107627737 |
| IQCK | −1.064764335 |
| IQGAP3 | −2.061688996 |
| ISPD | −1.879226849 |
| ITGA1 | −1.353730434 |
| ITGA4 | −1.756671957 |
| ITPR1 | −1.290522642 |
| ITPR2 | −1.233472544 |
| KCNK10 | −2.68829958 |
| KCNQ5 | −2.008072711 |
| KHDRBS3 | −1.145560989 |
| KIAA0101 | −1.461639006 |
| KIAA0825 | −1.622878808 |
| KIAA1524 | −1.392420329 |
| KIAA1644 | −1.799956723 |
| KIF11 | −1.878590906 |
| KIF14 | −2.53528912 |
| KIF15 | −2.216792744 |
| KIF18A | −2.041415274 |
| KIF18B | −2.456303841 |
| KIF20A | −2.8739185 |
| KIF20B | −1.335643536 |
| KIF23 | −1.80247136 |
| KIF24 | −1.392867165 |
| KIF26B | −1.838433497 |
| KIF2C | −2.287148765 |
| KIF4A | −2.522518287 |
| KIF4B | −2.278006561 |
| KIFC1 | −2.018332665 |
| KLHL13 | −1.355922156 |
| KNTC1 | −1.005796394 |
| KPNA2 | −1.290854042 |
| L3MBTL4 | −1.577144676 |
| LARGE | −2.256213738 |
| LBR | −1.031056323 |
| LEF1 | −1.277296868 |
| LEPR | −1.166781312 |
| LFNG | −1.599869881 |
| LHFP | −1.064934578 |
| LIMCH1 | −1.292609661 |
| LINC00341 | −1.013052052 |
| LMCD1 | −1.009878102 |
| LMNB1 | −2.526637995 |
| LNP1 | −1.303478188 |
| LOC100128191 | −1.134938013 |
| LOC100128881 | −1.090189815 |
| LOC100129961 | −1.331714119 |
| LOC100288637 | −1.889382704 |
| LOC100506711 | −1.459828788 |
| LOC100506844 | −1.238994387 |
| LOC100506994 | −1.030046919 |
| LOC100507552 | −3.443851009 |
| LOC100652789 | −1.082283866 |
| LOC285141 | −1.573604306 |
| LOC642846 | −1.033203026 |
| LOC647946 | −2.25998556 |
| LRBA | −1.087162349 |
| LRIG1 | −1.024924857 |
| LRP8 | −1.42572786 |
| LRRC6 | −1.488389369 |
| LRRIQ1 | −1.751414291 |
| LTBP1 | −1.813158937 |
| LZTS1 | −1.66064357 |
| MAD2L1 | −1.591320994 |
| MAGI3 | −1.089745698 |
| MAP6 | −1.031260549 |
| MAPK10 | −1.33357193 |
| MATN3 | −1.028109037 |
| MBOAT1 | −1.196601248 |
| MCM10 | −2.303622809 |
| MCM3 | −1.173047908 |
| MCM5 | −1.300923302 |
| MCM6 | −1.364315385 |
| MCM7 | −1.074498906 |
| MEF2C | −2.000689675 |
| MELK | −1.057551244 |
| METAP1D | −1.067957808 |
| MGC16121 | −1.04238246 |
| MKI67 | −2.74797697 |
| MMP2 | −1.17402456 |
| MMS22L | −1.149026385 |
| MND1 | −1.741478459 |
| MOXD1 | −1.460995365 |
| MPHOSPH9 | −1.15786143 |
| MSH5-C6orf26 | −1.040129645 |
| MSRA | −2.240412801 |
| MTBP | −1.01902842 |
| MYBL1 | −1.698796151 |
| MYBL2 | −2.022262666 |
| MYH15 | −2.192048185 |
| MYLK4 | −1.05279565 |
| NAV3 | −1.110567684 |
| NCALD | −1.199097373 |
| NCAPD2 | −1.224817576 |
| NCAPG | −2.247458098 |
| NCAPG2 | −1.585127369 |
| NCAPH | −2.170881812 |
| NCKAP5 | −1.342371268 |
| NCOA1 | −1.154674374 |
| NDC80 | −2.165240026 |
| NEIL3 | −2.29503331 |
| NEK11 | −1.026289133 |
| NEK2 | −2.208099443 |
| NOS1 | −1.310961641 |
| NRGN | −1.689312634 |
| NTM | −2.048027621 |
| NTNG1 | −1.415593761 |
| NUBPL | −1.096121588 |
| NUCB2 | −1.074994468 |
| NUF2 | −2.143706843 |
| NUSAP1 | −1.570361409 |
| ODC1 | −1.192092225 |
| ODZ3 | −1.844793468 |
| ODZ4 | −1.318047355 |
| OIP5 | −1.387288305 |
| ORC1 | −1.957553549 |
| ORC6 | −1.113974953 |
| OSBPL6 | −1.004909427 |
| OXCT1 | −1.088317263 |
| P4HA3 | −3.230028297 |
| PALM2 | −1.258674299 |
| PALMD | −1.231475809 |
| PARD3B | −2.825199287 |
| PBK | −2.22936512 |
| PCDH18 | −1.489762025 |
| PCDHAC2 | −1.484449311 |
| PCLO | −1.276919308 |
| PCSK5 | −1.300996825 |
| PDE4D | −1.179913183 |
| PDGFC | −1.025319775 |
| PDIA2 | −1.385271 |
| PDIA4 | −1.259521447 |

TABLE 3-continued

Genes down-regulated by UVR

| Gene ID | Log2FC |
| --- | --- |
| PEG10 | −1.227483825 |
| PFAS | −1.051620468 |
| PHGDH | −1.227080584 |
| PID1 | −1.453305805 |
| PIF1 | −2.616987868 |
| PIK3C2G | −2.501961882 |
| PKI55 | −1.083926432 |
| PKMYT1 | −1.844074552 |
| PLCB4 | −1.013542456 |
| PLK1 | −2.434416727 |
| PLK4 | −1.534332316 |
| PLXDC2 | −1.404520551 |
| PLXNC1 | −1.085076724 |
| PLXND1 | −1.348170161 |
| POLA1 | −1.343856772 |
| POLE2 | −1.769737957 |
| POLN | −1.486625284 |
| POLQ | −2.072375564 |
| POLR3G | −1.005696232 |
| PRC1 | −1.947640952 |
| PRDM5 | −1.585370558 |
| PRICKLE1 | −1.498603086 |
| PRIM1 | −1.160571677 |
| PRIM2 | −1.004231581 |
| PRKCA | −1.601780357 |
| PRR11 | −1.833215683 |
| PRTFDC1 | −1.228474421 |
| PRUNE2 | −3.224761055 |
| PSAT1 | −1.204185638 |
| PSMC3IP | −1.085977037 |
| PSRC1 | −2.121773024 |
| PTGS1 | −1.085302707 |
| PTPRG | −1.65358899 |
| PTPRZ1 | −1.507226274 |
| PYCR1 | −1.057369077 |
| RABGAP1L | −1.289087491 |
| RACGAP1 | −1.234902292 |
| RAD51 | −1.480782503 |
| RAD51AP1 | −1.372089728 |
| RAD51B | −1.42302095 |
| RAD54B | −1.21691423 |
| RAD54L | −1.432880045 |
| RANBP17 | −1.427466251 |
| RAPGEF4 | −1.594354405 |
| RBL1 | −1.430172588 |
| RBMS3 | −1.312042071 |
| RECQL4 | −1.184607991 |
| RFC3 | −1.107780232 |
| RFX3 | −1.411661589 |
| RGMB | −1.153194674 |
| RGPD5 | −1.371696038 |
| RGS5 | −1.453690846 |
| RMI1 | −1.121325391 |
| RNLS | −1.262777743 |
| ROBO1 | −1.187476219 |
| ROR1 | −1.51612717 |
| RPL22L1 | −1.338137604 |
| RPS6KA2 | −1.461033057 |
| RRM2 | −1.991311534 |
| RSRC1 | −1.178787776 |
| RUNDC2A | −1.265189228 |
| RUNDC3B | −2.323290022 |
| RYR3 | −1.010652199 |
| S1PR1 | −1.018299255 |
| SAMD3 | −1.661703151 |
| SCAPER | −1.144478129 |
| SCFD2 | −1.922440965 |
| SCLT1 | −1.080112469 |
| SCMH1 | −1.052116405 |
| SCN9A | −1.398160949 |
| SDF2L1 | −1.284992898 |
| SDK1 | −2.13313528 |
| SEMA3D | −2.01252048 |
| SEMA3E | −2.516404159 |
| SEMA5A | −2.929174239 |
| SERGEF | −1.093861415 |
| SFTA1P | −1.191338272 |
| SFXN2 | −1.409000972 |
| SGOL1 | −2.176977698 |
| SGOL2 | −1.985641318 |
| SHCBP1 | −2.176358987 |
| SIRPB1 | −1.073654141 |
| SKA1 | −2.292700912 |
| SKA3 | −2.130705608 |
| SKP2 | −1.100554338 |
| SLC16A9 | −1.437744237 |
| SLC2A13 | −1.400132755 |
| SLC43A1 | −1.088907499 |
| SLC43A3 | −1.115380732 |
| SLC7A11 | −1.101550321 |
| SLC7A2 | −1.316982859 |
| SLC7A5 | −1.092962509 |
| SLC8A1 | −3.890468578 |
| SLC9A9 | −1.772424605 |
| SLFN11 | −1.344303011 |
| SLFN13 | −1.001484977 |
| SLIT2 | −1.635335628 |
| SLIT3 | −2.106888295 |
| SMC2 | −1.07784523 |
| SMC4 | −1.372671433 |
| SMYD3 | −1.914279342 |
| SNORA51 | −1.176748219 |
| SNORD101 | −1.349751243 |
| SNORD12 | −1.264153814 |
| SNORD14C | −1.373015383 |
| SNORD14E | −1.065302198 |
| SNORD17 | −1.364493668 |
| SNORD28 | −1.221337171 |
| SNORD88B | −1.055543084 |
| SNX10 | −1.079060213 |
| SNX29 | −1.410602348 |
| SOX11 | −1.223375096 |
| SOX6 | −1.032166298 |
| SPAG17 | −1.659735287 |
| SPAG5 | −1.65235008 |
| SPATA13 | −1.075647439 |
| SPATA17 | −2.430679132 |
| SPATA5 | −1.14726314 |
| SPATA6 | −1.379798818 |
| SPC24 | −1.942352943 |
| SPC25 | −2.181086004 |
| SPEF2 | −1.218600348 |
| SSBP2 | −1.270375221 |
| ST8SIA4 | −1.171785056 |
| STAG1 | −1.211513978 |
| STAG3L1 | −1.346197566 |
| STAMBPL1 | −1.060856801 |
| STAR | −1.769078887 |
| STIL | −1.496402119 |
| STK32B | −2.069785601 |
| STK33 | −2.30665232 |
| STS | −1.532500152 |
| STX8 | −1.127540559 |
| STXBP4 | −1.351053971 |
| SULT1E1 | −1.560657669 |
| SUPT3H | −1.559626944 |
| SUV39H1 | −1.055427461 |
| SVEP1 | −1.172034978 |
| SYT1 | −1.850488964 |
| TACC3 | −1.807917227 |
| TBC1D3P1-DHX40P1 | −1.718629676 |
| TBC1D5 | −1.034717598 |
| TBX1 | −1.002975218 |
| TCF19 | −1.331891307 |
| TDRD9 | −1.056032287 |
| TGM4 | −1.037262874 |
| THBS1 | −1.017293581 |
| THBS2 | −1.724598457 |
| TIMELESS | −1.088272778 |
| TK1 | −1.51351299 |
| TLL1 | −1.746038163 |
| TLR6 | −1.761305528 |

TABLE 3-continued

Genes down-regulated by UVR

| Gene ID | Log2FC |
|---|---|
| TMEM117 | −1.208085002 |
| TMEM97 | −1.212401251 |
| TMTC2 | −1.815467237 |
| TNC | −1.600248019 |
| TNS1 | −1.554340131 |
| TOP2A | −2.386015457 |
| TPK1 | −2.246074973 |
| TPX2 | −1.813159472 |
| TRAIP | −1.18054426 |
| TRAPPC9 | −1.031296849 |
| TRIM59 | −1.075976395 |
| TRIP13 | −1.57140204 |
| TROAP | −2.358691763 |
| TTC26 | −1.066910781 |
| TTC28 | −1.43380084 |
| TTK | −2.183953926 |
| TUBA1B | −1.549605554 |
| TUBA1C | −1.06766931 |
| TXNDC5 | −1.014330286 |
| TYW1B | −1.055561674 |
| UBE2C | −2.550014168 |
| UBE2S | −1.293876674 |
| UCHL1 | −1.000277324 |
| UHRF1 | −1.654077016 |
| USP13 | −1.211411674 |
| UTP20 | −1.159131427 |
| WDPCP | −1.986624455 |
| WDR17 | −1.469613807 |
| WDR4 | −1.122037801 |
| WDR62 | −1.327456068 |
| WDR65 | −1.366210497 |
| WDR7 | −1.053132054 |
| WDR76 | −1.760139175 |
| WHSC1 | −1.36218294 |
| WNT10B | −1.302096355 |
| WWOX | −2.010534417 |
| XRCC2 | −2.075258306 |
| XRCC4 | −1.285559504 |
| XYLT1 | −1.538493127 |
| ZNF367 | −1.804784888 |
| ZNF492 | −1.476335538 |
| ZNF546 | −1.044266261 |
| ZNF724P | −1.23386724 |
| ZNF730 | −1.15988286 |
| ZRANB3 | −1.691812182 |
| ZWINT | −1.120333991 |

Example 3

Time-Dependent Transcriptomic Changes in Response to UVR

Figure 1B:
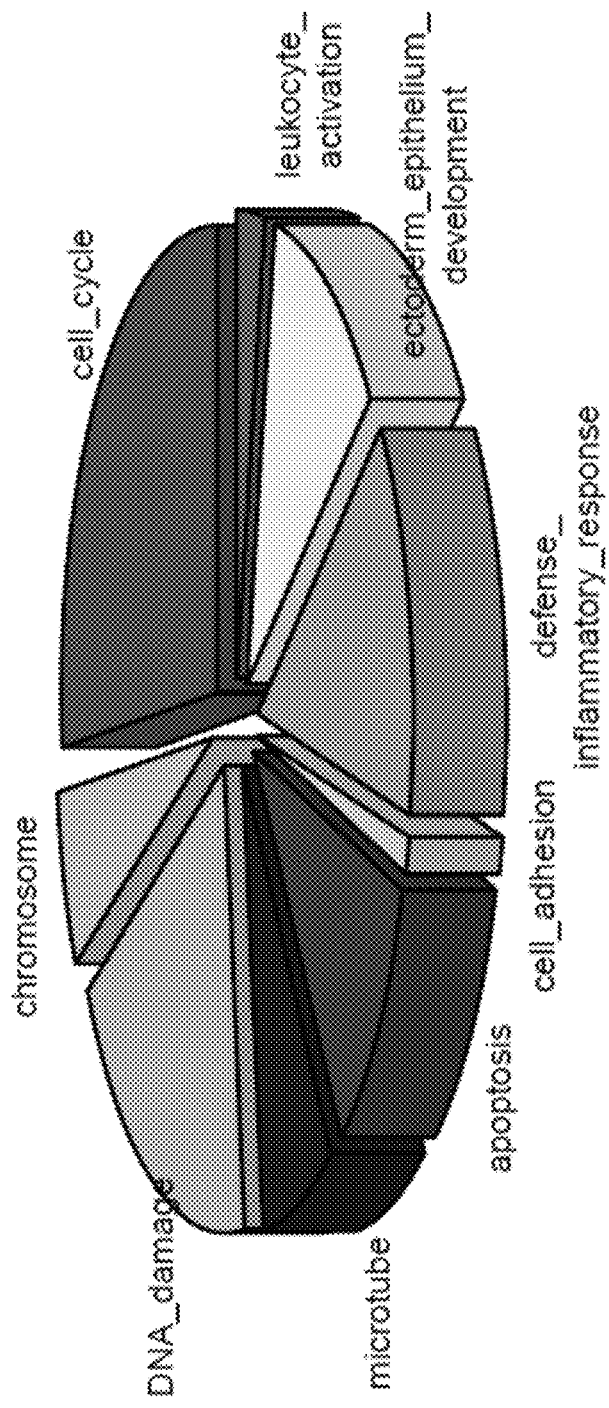
FIG. 1B shows functional annotation of differentially expressed genes by DAVID pathway analysis. The size of the pie chart is proportional to the number of genes in each pathway.
Figure 2:
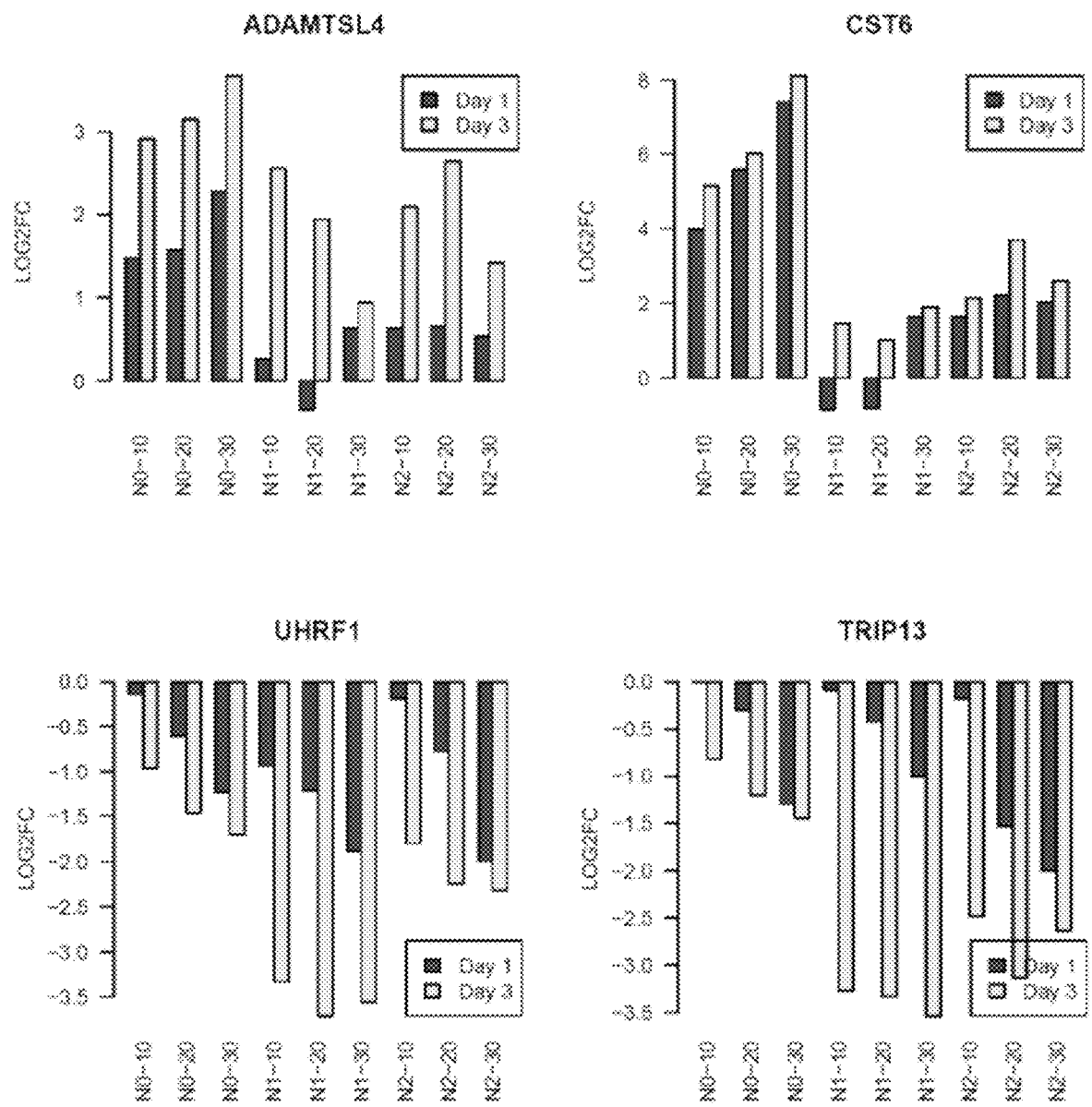
FIG. 2 shows graphs showing the time-dependent pattern of differential gene signatures by comparing Day 3 (yellow) and Day 1 (red). The y-axis shows the log 2 fold change of gene expression between irradiated and non-irradiated control cells. The x-axis indicates the sample names. ADAMTSL4 and CST6 demonstrated time-dependent up-regulation, while UHRF1 and TRIP13 displayed time-dependent down-regulation in response to UVR.

Our PCA analysis in FIG. 1A revealed time-dependent variations in UVR-responsiveness. To identify genes exhibiting time-dependent cumulative UVR responsiveness, we performed paired t-tests to compare the gene expression signatures of Day 3 versus those of Day 1 for each keratinocyte cell line (NO, N1 and N2) under the same UVR dose. 164 out of the 531 up-regulated genes showed higher expressions at Day 3 than at Day 1 (FDR-corrected p-value <0.05); while 239 out of the 610 down-regulated genes were more repressed at Day 3 than at Day 1 at the same p-value threshold (Table 4). Two examples of time-dependent up-regulation include ADAMTSL4, encoding a disintegrin and metalloproteinase; and CST6, encoding a cystatin superfamily protein. Examples of time-dependent down-regulation include UHRF1, encoding a member of a subfamily of RING-finger type E3 ubiquitin ligases; and TRIP13, which encodes a protein that interacts with thyroid hormone receptors (FIG. 2).

TABLE 4

Genes displaying time-dependent changes in mRNA expression following UVR

Down-regulated

ANLN
ARHGAP11A
ARHGAP11B
ASF1B
ASPM
ATAD2
ATAD5
AURKA
AURKB
BARD1
BIRC5
BLM
BORA
BRCA1
BRCA2
BRIP1
BUB1
BUB1B
C11orf82
C14orf80
C15orf42
C16orf59
C1orf112
C9orf100
CASC5
CCDC150
CCNA2
CCNB1
CCNB2
CCNE2
CCNF
CDC20
CDC25A
CDC25C
CDC45
CDC6
CDC7
CDCA2
CDCA3
CDCA5
CDCA8
CDK1
CDKN2C
CDKN3
CDT1
CENPA
CENPE
CENPF
CENPH
CENPI
CENPJ
CENPK
CENPM
CENPN
CENPO
CENPW
CEP55
CHAF1A
CHEK1
CHRNA5
CKAP2L
CKS1B
CLSPN
DBF4
DBF4B
DDX12P
DEPDC1
DHFR
DLEU1
DLGAP5
DSCC1
DTL
DUSP9
E2F1
E2F8

TABLE 4-continued

Genes displaying time-dependent changes
in mRNA expression following UVR

EDNRA
EME1
ERCC6L
ESCO2
ESPL1
EXO1
FAM111B
FAM167A
FAM54A
FAM64A
FAM72A
FAM72B
FAM83D
FANCA
FANCB
FANCD2
FANCI
FBXO5
FEN1
FKBP11
FOXM1
GINS1
GINS2
GINS4
GLT8D2
GPR63
GSG2
GTSE1
H2AFX
HAUS8
HELLS
HIST1H2BH
HJURP
HMGB2
HMMR
HPDL
HYOU1
IL7R
INCENP
IQGAP3
KIAA0101
KIAA1524
KIF11
KIF14
KIF15
KIF18A
KIF18B
KIF20A
KIF20B
KIF23
KIF24
KIF2C
KIF4A
KIF4B
KIFC1
KPNA2
LBR
LMNB1
LOC100128191
LOC100506711
MAD2L1
MCM10
MCM3
MCM5
MCM7
MELK
MKI67
MMP2
MMS22L
MND1
MTBP
MYBL1
MYBL2
MYH15
NCAPG
NCAPG2
NCAPH

NDC80
NEIL3
NEK2
NRGN
NUF2
NUSAP1
OIP5
ORC1
ORC6
PALMD
PBK
PCDH18
PCDHAC2
PEG10
PFAS
PKMYT1
PLK1
PLK4
POLE2
POLQ
POLR3G
PRC1
PRIM1
PSMC3IP
PTGS1
RACGAP1
RAD51
RAD51AP1
RAD54B
RAD54L
RBL1
RECQL4
RFC3
RGMB
RMI1
RRM2
S1PR1
SEMA3D
SFTA1P
SFXN2
SGOL1
SGOL2
SHCBP1
SKA1
SKA3
SKP2
SLC43A3
SLFN13
SMC2
SMC4
SNORD17
SNORD28
SOX11
SPAG5
SPC24
SPC25
STAMBPL1
STIL
SULT1E1
SUV39H1
TACC3
TCF19
TGM4
THBS1
TIMELESS
TK1
TMEM97
TOP2A
TPX2
TRAIP
TRIM59
TRIP13
TROAP
TTK
UBE2C
UBE2S
UHRF1

TABLE 4-continued

Genes displaying time-dependent changes in mRNA expression following UVR

UTP20
WDR4
WDR62
WDR65
WDR76
XRCC2
ZNF367
ZNF492
ZNF724P
ZWINT

Up-regulated

ABCA12
ABLIM3
ACBD4
ACTA2
ADAMTS13
ADAMTS7
ADAMTSL4
ADHFE1
ADSSL1
AIFM3
ALDH3B2
ALOX15B
ANKRD29
APOE
ATP12A
B3GALT4
BLNK
BNIP3L
BTBD19
C11orf35
C19orf46
C1orf126
C1orf38
C1orf88
C5orf41
C6orf138
C7orf10
C9orf7
CARD14
CBX7
CCDC64B
CCL20
CD68
CLDN7
COX6B2
CRCT1
CST6
CTSS
CUL9
CYGB
DKFZp434J0226
DPP4
DQX1
DYRK1B
EPHB2
ESPN
FBXO32
FGF11
FN3K
FOLR3
FTH1
FTL
FXYD3
G0S2
GABARAPL1
GAMT
GDA
GGT1
GIPR
GPNMB
GRIN3B
HBEGF
HIST1H2AC
HLA-G
HSD17B14

HSD17B2
ICAM1
ICAM4
IDUA
IL32
IL33
IRAK2
IRF5
ITIH4
ITPKC
KCTD11
KIAA1370
KLHDC9
KLHL24
KLK11
KRT15
KRT19
KRT23
KRT37
KYNU
LCN2
LINC00086
LOC100049716
LOC100129781
LOC100131096
LOC100131564
LOC100505623
LOC100507452
LOC284080
LOC284440
LOC646471
LOC728975
LYNX1
MEG3
MIR21
MLPH
MME
MNT
MUC1
MXD4
MXI1
MYO15B
N4BP2L1
NDRG4
NFATC4
NOTCH3
NUPR1
PAPL
PIK3IP1
PLA2G4C
PLEKHG1
PNLIPRP3
ProSAPiP1
PRSS22
PRSS8
PSORS1C1
QPCT
REEP6
RET
RHBDL1
RNF208
RUNDC3A
RYR1
S100A4
S100A6
SAA1
SGPP2
SIRPB2
SLC28A3
SLPI
SORT1
SPNS2
SULT1A1
TCP11L2
TIMP2
TLCD2
TLR2

TABLE 4-continued

Genes displaying time-dependent changes
in mRNA expression following UVR

TM7SF2
TMEM38A
TMEM61
TMEM91
TMPRSS4
TNFAIP8L3
TNFRSF14
TREM2
TSPAN10
TTC39A
TTC9
TTLL3
TXNIP
VAMP5
VNN1
WFDC5
YPEL2
YPEL3
YPEL4
ZFHX2
ZNF185
ZNF610

Example 4

Dose-Dependent Transcriptomic Changes in Response to UVR

In addition to the time-dependent UVR-responsiveness described above, we were also interested in identifying genes that may display dose-dependent changes in response to UVR. To do so, we fitted linear regression models for each of the differentially expressed genes using UVR doses (10, 20 and 30 mJ/cm$^2$) as independent variables and gene expression as the dependent variable for each keratinocyte cell line (N0, N1, N2) at the same time point (Day 1 or 3). For each gene, we constructed six models representing the following six conditions: N0-1d, N0-3d, N1-1d, N1-3d, N2-1d and N2-3d, We then integrated the six coefficient p-values from the six models using Fisher's method. We found that 285 out of the 531 up-regulated genes showed dose-dependent up-regulation with FDR-corrected p-value <0.05; and 452 out of the 610 down-regulated genes demonstrated significant dose-dependent decreases in gene expression at the same FDR threshold (Table 5). Dose-dependent changes in four representative genes from each group were illustrated in FIG. 3.

TABLE 5

Genes displaying dose-dependent changes
in mRNA expression following UVR

Down-regulated

ABCC4
ABI3BP
ADAMTSL1
AGTPBP1
AKAP6
AKAP7
ALDH1L2
ALG14
ALMS1
ANKRD44
ANLN
ANXA6
APLN
ARHGAP11A
ARHGAP11B

TABLE 5-continued

Genes displaying dose-dependent changes
in mRNA expression following UVR

ARHGAP19
ARHGAP33
ARSB
ASF1B
ASNS
ASPM
ATAD2
ATAD5
AURKA
AURKB
B3GALTL
BARD1
BBS9
BCAT1
BCL2
BEND6
BIRC5
BLM
BORA
BRCA1
BRCA2
BRIP1
BUB1
BUB1B
C11orf82
C12orf26
C12orf48
C14orf80
C15orf42
C16orf59
C21orf58
C3orf26
C4orf21
C5
C9orf100
C9orf93
CADPS2
CAMKMT
CASC2
CASC5
CBS
CCDC150
CCDC152
CCDC18
CCDC3
CCNA2
CCNB1
CCNB2
CCNF
CDC20
CDC25C
CDC45
CDC6
CDC7
CDCA2
CDCA3
CDCA5
CDCA7
CDCA8
CDH4
CDK1
CDKAL1
CDKN3
CDON
CDT1
CENPA
CENPE
CENPF
CENPH
CENPI
CENPJ
CENPM
CENPN
CENPO
CENPW
CEP112
CEP128

TABLE 5-continued

Genes displaying dose-dependent changes
in mRNA expression following UVR

| |
|---|
| CEP55 |
| CHAF1A |
| CHEK1 |
| CHRNA5 |
| CHSY3 |
| CIT |
| CKAP2L |
| CKS1B |
| CLMP |
| CLSPN |
| CNTLN |
| CNTN1 |
| COL12A1 |
| COL18A1 |
| COL4A1 |
| COL4A2 |
| COL8A1 |
| COMMD1 |
| COMMD10 |
| CPS1 |
| CREB5 |
| CTNNAL1 |
| DBF4 |
| DBF4B |
| DCHS1 |
| DDX12P |
| DEPDC1 |
| DEPDC1B |
| DHFR |
| DIAPH2 |
| DIAPH3 |
| DLEU1 |
| DLEU2 |
| DLGAP5 |
| DLL1 |
| DMC1 |
| DNAH5 |
| DOCK10 |
| DPYD |
| DPYSL3 |
| DRP2 |
| DSCC1 |
| DTL |
| DTWD2 |
| DYNC2H1 |
| DZIP3 |
| E2F1 |
| E2F8 |
| EDA |
| EFCAB11 |
| EFCAB2 |
| EFHC2 |
| ELAVL2 |
| ELOVL6 |
| ELP4 |
| EME1 |
| ENOX1 |
| EPB41L2 |
| ERCC6L |
| ESPL1 |
| EXO1 |
| EXTL2 |
| FAF1 |
| FAM111B |
| FAM167A |
| FAM172A |
| FAM54A |
| FAM64A |
| FAM72A |
| FAM72B |
| FAM72D |
| FAM83D |
| FANCA |
| FANCB |
| FANCC |
| FANCD2 |
| FANCI |
| FAR2 |
| FARS2 |
| FBN2 |
| FBXL17 |
| FBXL7 |
| FBXO43 |
| FBXO5 |
| FGFBP1 |
| FGGY |
| FHIT |
| FIGN |
| FKBP11 |
| FOXM1 |
| GALNT10 |
| GALNTL4 |
| GINS1 |
| GINS2 |
| GINS4 |
| GIPC2 |
| GLI1 |
| GLT8D2 |
| GMDS |
| GNB3 |
| GPC6 |
| GPHN |
| GPR39 |
| GPR63 |
| GPSM2 |
| GRB14 |
| GRIA1 |
| GRIP1 |
| GSG2 |
| GTDC1 |
| GTSE1 |
| H2AFX |
| HAUS8 |
| HELLS |
| HJURP |
| HMCN1 |
| HMGB2 |
| HMGCS1 |
| HMMR |
| HS6ST2 |
| INCENP |
| IQCK |
| IQGAP3 |
| ISPD |
| ITGA1 |
| ITGA4 |
| ITPR1 |
| ITPR2 |
| KCNK10 |
| KCNQ5 |
| KHDRBS3 |
| KIAA0825 |
| KIAA1524 |
| KIF11 |
| KIF14 |
| KIF15 |
| KIF18A |
| KIF18B |
| KIF20A |
| KIF20B |
| KIF23 |
| KIF24 |
| KIF26B |
| KIF2C |
| KIF4A |
| KIF4B |
| KIFC1 |
| KLHL13 |
| KNTC1 |
| KPNA2 |
| L3MBTL4 |
| LARGE |
| LBR |
| LEF1 |

TABLE 5-continued

Genes displaying dose-dependent changes in mRNA expression following UVR

LFNG
LHFP
LMCD1
LMNB1
LNP1
LOC100128191
LOC100288637
LOC100506711
LOC100506994
LOC100507552
LOC100652789
LOC642846
LOC647946
LRIG1
LRP8
LRRC6
LRRIQ1
LTBP1
LZTS1
MAD2L1
MAGI3
MAP6
MATN3
MBOAT1
MCM10
MCM3
MCM5
MCM6
MCM7
MELK
METAP1D
MGC16121
MKI67
MMP2
MMS22L
MND1
MOXD1
MSRA
MTBP
MYBL2
NCAPD2
NCAPG
NCAPG2
NCAPH
NCKAP5
NCOA1
NDC80
NEIL3
NEK2
NTM
NUF2
NUSAP1
ODZ3
ORC1
ORC6
OSBPL6
OXCT1
P4HA3
PALM2
PBK
PCDHAC2
PDE4D
PDGFC
PEG10
PFAS
PHGDH
PID1
PIF1
PIK3C2G
PKI55
PKMYT1
PLK1
PLK4
PLXNC1
PLXND1
POLA1
POLE2

TABLE 5-continued

Genes displaying dose-dependent changes in mRNA expression following UVR

POLQ
POLR3G
PRC1
PRDM5
PRICKLE1
PRIM1
PRKCA
PRR11
PRTFDC1
PRUNE2
PSAT1
PSMC3IP
PSRC1
PTGS1
PTPRG
PTPRZ1
PYCR1
RACGAP1
RAD51
RAD51AP1
RAD51B
RAD54B
RAD54L
RANBP17
RAPGEF4
RBL1
RECQL4
RFC3
RMI1
RNLS
ROBO1
ROR1
RPL22L1
RPS6KA2
RRM2
RSRC1
RUNDC2A
ZNF730
RUNDC3B
RYR3
SCAPER
SCFD2
SCLT1
SCMH1
SCN9A
SDF2L1
SDK1
SEMA3D
SEMA3E
SEMA5A
SERGEF
SFXN2
SGOL1
SGOL2
SHCBP1
SKA1
SKA3
SKP2
SLC16A9
SLC2A13
SLC43A1
SLC7A5
SLC8A1
SLFN13
SLIT3
SMC2
SMC4
SMYD3
SNORA51
SNX29
SPAG17
SPAG5
SPATA13
SPATA17
SPATA5
SPATA6
SPC24

TABLE 5-continued

Genes displaying dose-dependent changes
in mRNA expression following UVR

SPC25
SPEF2
STAG1
STIL
STK33
STS
STXBP4
SUPT3H
SUV39H1
SYT1
TACC3
TBX1
TCF19
TDRD9
THBS1
THBS2
TIMELESS
TK1
TLL1
TLR6
TMEM97
TMTC2
TNC
TNS1
TOP2A
TPK1
TPX2
TRAIP
TRAPPC9
TRIM59
TRIP13
TROAP
TTC26
TTK
TUBA1C
TYW1B
UBE2C
UHRF1
USP13
UTP20
WDPCP
WDR4
WDR62
WDR65
WDR7
WDR76
WHSC1
WWOX
XRCC2
XRCC4
XYLT1
ZNF367
Up-regulated A4GALT
ABCD1
ABHD4
ABLIM3
ACAP1
ACER2
ADCK3
AIM1L
AKR1B10
AKR1C1
AKR1C2
ARHGAP30
ARNT2
ATF3
AVPI1
B3GNT3
BCL2L1
BCL6
BIK
BIRC3
BMF
BNIP3L
BTBD19

TABLE 5-continued

Genes displaying dose-dependent changes
in mRNA expression following UVR

BTG1
C11orf35
C11orf9
C16orf5
C17orf103
C1orf51
C1orf74
C5orf41
C9orf7
CARD18
CASP9
CCDC11
CCK
CD55
CD68
CD74
CDKN1A
CDKN2B
CDKN2D
CDSN
CGN
CHST2
CITED2
CLCF1
CLDN1
CLDN23
CLDN4
CLDN7
CLEC2B
CLU
CNFN
CRB3
CRCT1
CRISPLD2
CRYAB
CSF1
CST6
CTSS
CYP2S1
DAPK1
DBNDD1
DEFB1
DENND1C
DHDH
DHRS3
DKFZp434J0226
DPP4
DUSP10
DYRK1B
EDA2R
ENO2
ENTPD3
ERBB3
FAM131C
FAM43A
FAM46A
FAM84A
FAM86HP
FDXR
FLJ32255
FLJ43663
FLNC
FN3K
FOLR3
FTH1
FTL
FUT2
FUT3
G0S2
GDA
GDF15
GGT1
GGT6
GIPR
GJB4
GLRX
GLS2

TABLE 5-continued

Genes displaying dose-dependent changes in mRNA expression following UVR

GPR172B
GPR37
GPRASP1
GPRC5A
GRB7
GREB1
GRHL3
GSDMA
H1F0
HAP1
HAPLN3
HBEGF
HBP1
HCAR2
HCAR3
HDAC5
HDAC9
HEPHL1
HES2
HIST1H1C
HIST1H2AC
HIST1H2BD
HIST1H2BK
HIST2H2BE
HIST3H2A
HLA-G
HMOX1
HSD17B14
HSD3B7
HSPB8
ICAM1
ID2
IL1B
IL1RN
IL23A
IL36RN
IL8
INPP5J
IRAK2
IRF5
IRF6
ISG20
ISYNA1
ITPKC
KCNN4
KCTD11
KIAA1257
KIAA1370
KLHL24
KLK10
KLK11
KLRG2
KRT13
KRT15
KRT19
KRT34
KRT37
KRT7
KRT80
LACC1
LBH
LCE1B
LCE1C
LCN2
LIF
LOC100133190
LOC100505974
LOC100506377
LOC100506746
LOC100507429
LOC100507452
LOC151475
LOC441869
LOC728975
LYPD5
MAP1LC3A
MCHR1

MDM2
MEG3
MUC1
MXD1
MXD4
MYBPHL
MYH16
NCF2
NDRG4
NEAT1
NFKBIA
NFKBIZ
NIPAL4
NLRP10
NR1D1
NR4A1
OCLN
P4HTM
PAPL
PCDH1
PDE6B
PGPEP1
PHLDB3
PI3
PIDD
PLAUR
PLEKHG6
PNLIPRP3
PNMAL1
PNRC1
PPP1R15A
PPP1R3B
PRDM1
PRICKLE4
ProSAPiP1
PRSS22
PRSS8
PTGS2
PVRL4
QPCT
RAB11FIP1
RASSF5
REEP6
RET
RGAG4
RGS16
RGS2
RHCG
RHPN1
RNASE7
RND2
RORA
RRAD
RRM2B
RUNDC3A
S100A4
SALL4
SAMD10
SBK1
SCNN1A
SELPLG
SEMA3B
SERPINB1
SERPINB2
SERTAD1
SESN1
SLAMF7
SLC46A1
SLPI
SMOC1
SPRR1B
SPRR3
SQSTM1
SYNGR3
TCP11L2
THBD
TLR2

TABLE 5-continued

Genes displaying dose-dependent changes
in mRNA expression following UVR

TM7SF2
TMEM125
TMEM184A
TMEM27
TMEM61
TMPRSS13
TNFAIP2
TNFRSF10C
TNFRSF14
TOB1
TP53INP1
TP53INP2
TPPP
TRAF1
TRAF3IP3
TRIM17
TSPAN10
TTC9
UCA1
ULBP1
ULK1
VAMP5
VNN1
VWCE
YPEL3
YPEL4
ZFYVE1
ZNF425
ZNF432
ZNF610
ZNF702P

Example 5

Identification of Conserved UVR Transcriptomic Signature Genes

Figure 4:
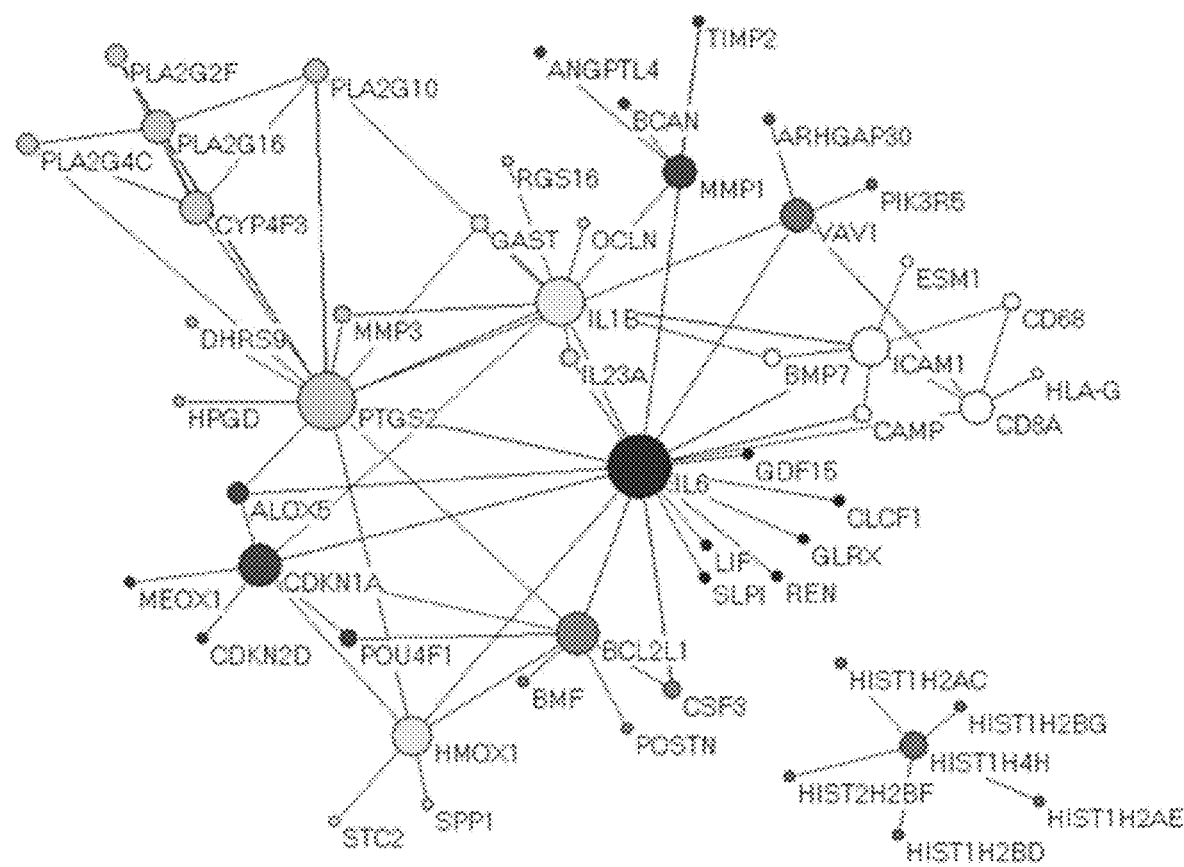
FIG. 4 shows protein-protein interaction network map illustrating hub genes as well as their interacting partners among UVR signature genes. Each vertice represents a gene and each edge indicates an interaction between the two genes. Genes belong to different clusters are colored in different colors respectively. The sizes of the vertices are proportionally to their degrees (number of interacting genes).
Figure 5A:
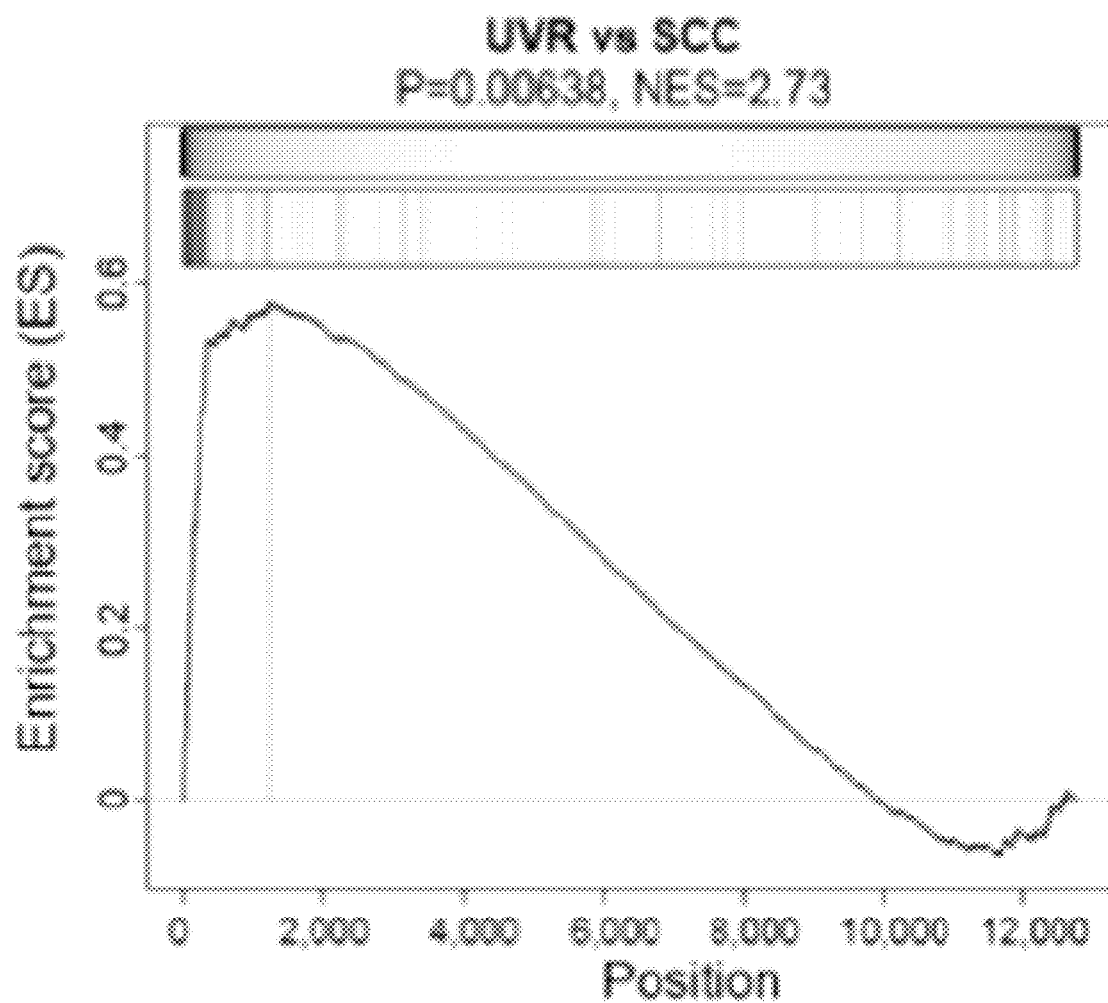
FIG. 5A shows a gene set enrichment analysis of UVR signatures (red bars) against the gene set dysregulated in human SCCs. UVR transcriptomic signature genes were sorted from the highest (left) to the lowest (right) based on their UVR-induced fold change. The normalized enrichment score (NES) and p values are indicated.
Figure 5B:
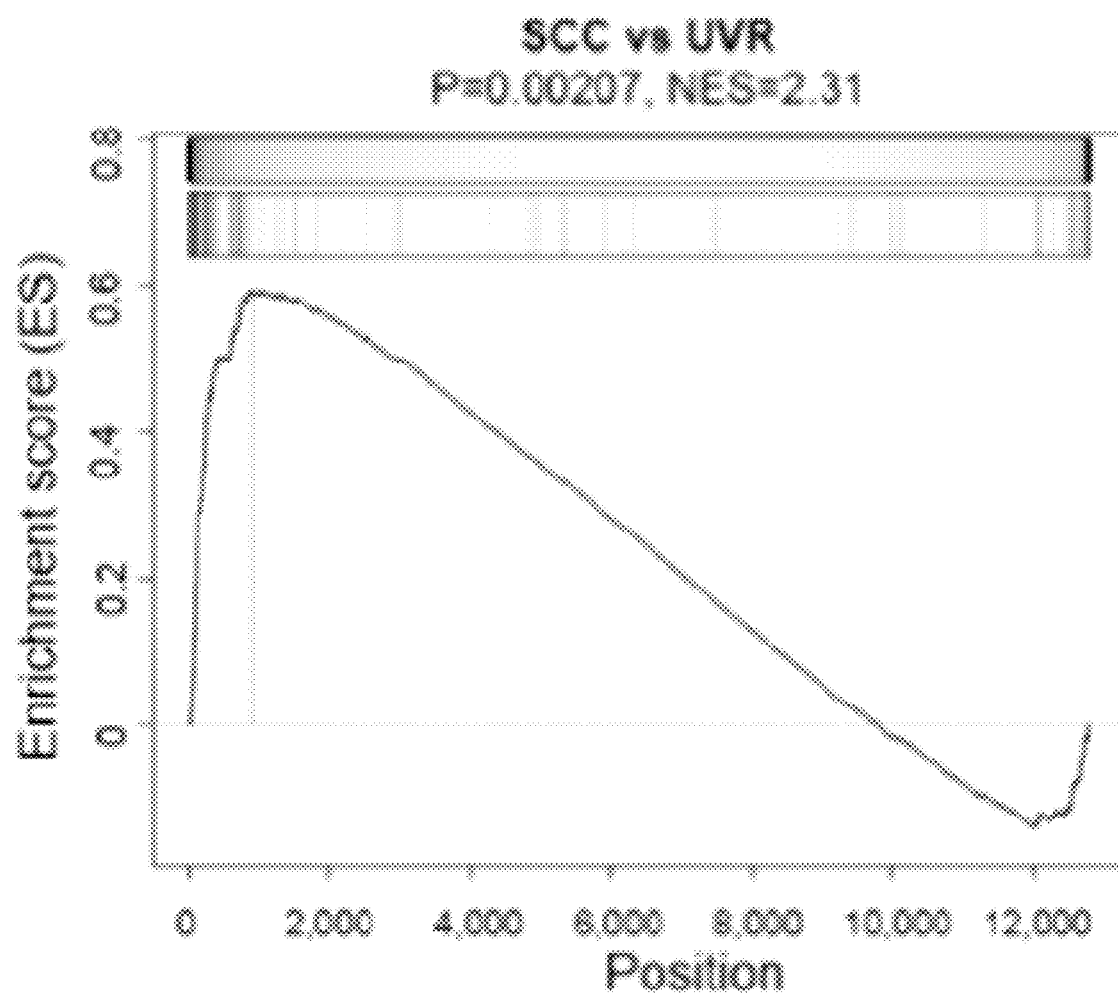
FIG. 5B shows gene set enrichment analysis of the human SCC signatures (red bars) against the UVR transcriptomic signature. SCC signature genes were sorted from the highest (left) to the lowest (right) based on the fold change between SCC and normal control tissues.
Figure 5C:
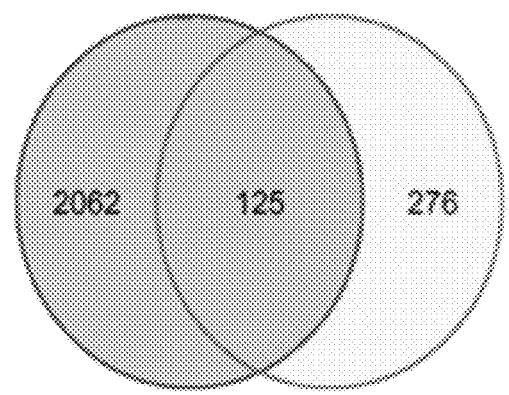
FIG. 5C shows Venn diagram showing the overlapping genes between UVR transcriptomic signatures and DEGs at 21 days after UVR.
Figure 5D:
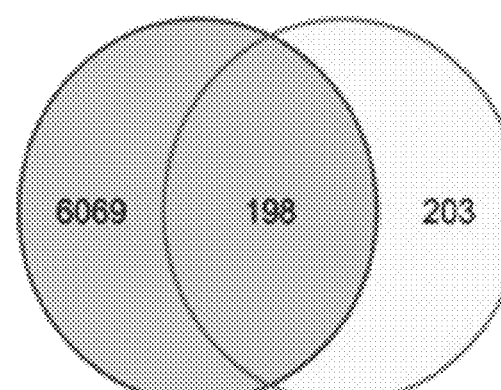
FIG. 5D and FIG. 5E show Venn diagram illustrating the overlapping genes between UVR transcriptomic signature and DEGs in two different human SCC cases.
Figure 5E:
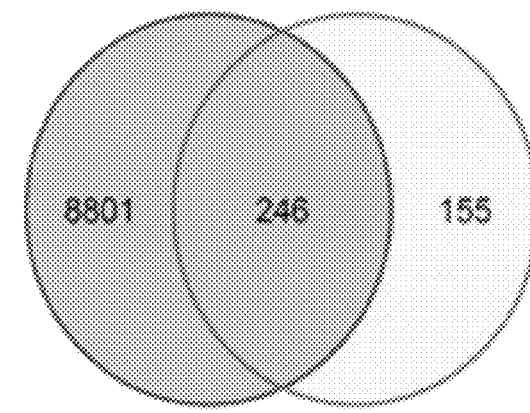

UVR is a potent regulator of the transcriptome, but its effect on the majority of genes is often transient and diminishes with time after exposure. The time-dependent kinetic changes illustrated in FIG. 2, nevertheless, suggested that UVR might exert persistent effects on a subset of genes that might serve as UVR transcriptomic signature. We speculated that such UVR signature may persist in the progeny cells of UVR-exposed cells and may have important biomarker values in assessing UVR-induced molecular damages. To characterize the genes consisting the UVR transcriptomic signature, we focused on DEG lists derived from 30 mJ/cm$^2$ UVR exposure to identify UVR-induced DEGs that were common among different keratinocyte lines (N0, N1, N2, and N6) at Days 1 and 3 after exposure. Through rigorous bioinformatics and statistical analyses, we identified 401 conserved UVR-induced DEGs that we designated as UVR transcriptomic signature (Table 6). To test whether protein-protein interactions (PPIs) exist among these UVR signature gene products, we performed network analysis using the Pajek software (version 3.1) (Batagelj 2004) based on the known and predicted protein interactions available in the STRING database (version 10). (Szlarczyk 2015) A STRING cutoff score at 0.7 was used to select PPIs with high confidence. Altogether, we found 54 vertices (genes) and 106 edges (interactions) among the UVR signature gene products (FIG. 4). Clustering analysis using the VOS algorithm (van Eck 2010) to maximize modularity within each cluster further revealed eleven modules that were all connected among each other except the histone protein cluster (FIG. 4). Among the UVR signature genes, 13 of them showed more than five interacting neighbors (degree), also known as the hubs on the PPI network, including IL6, PTGS2, IL1B, CDKN1A, BCL2L1, ICAM1, HMOX1, VAV1, PLA2G16, MMP1, HIST1H4H, CYP4F3, and CD8A, highlighting the potentially central roles of these genes in mediating UVR responses.

TABLE 6

Conserved UVR signature genes in response to 30
mJ/cm$^2$ UVR among different keratinocyte lines ABCD1
ABLIM3
ADAMTS14
AGAP11
ALG1L
ALOX5
ANGPTL4
ANKRD20A5P
ANKRD29
ANKRD33
ANKRD56
APOBEC3H
ARC
ARHGAP30
ARNT2
ASPRV1
ATG9B
B3GNT3
BCAN
BCL2L1
BMF
BMP7
C10orf10
C14orf34
C15orf48
C15orf52
C17orf28
C17orf67
C1orf228
C1orf68
C20orf195
C2orf54
C3orf25
C6orf15
C7orf10
CAMP
CAPN12
CARD18
CASKIN1
CATSPERG
CCDC110
CCDC62
CCIN
CD68
CD70
CD8A
CDH16
CDKN1A
CDKN2D
CDSN
CEACAM1
CEACAM6
CELF5
CHRNA9
CLCF1
CLDN17
CLDN23
CLDN4
CLDN7
CLDN9
CLEC18B
CLEC3B
CLGN
CLIC6
CNFN
CRCT1
CRISPLD2
CRYM
CSF3
CST6

TABLE 6-continued

Conserved UVR signature genes in response to 30 mJ/cm² UVR among different keratinocyte lines CT62
CTSL3
CYGB
CYP24A1
CYP4F3
CYTH4
DAPK1
DEFB1
DHRS9
DKK4
DPP4
DUSP13
ELF3
ENKUR
ENTPD3
EPHB2
ESM1
FA2H
FAM110C
FAM115C
FAM167B
FAM182B
FAM25A
FAM46C
FAM65C
FAM83E
FBP1
FER1L4
FLJ34208
FLJ43663
FLNC
FOXA1
FTL
FUT2
FUT3
GABBR2
GAD1
GAS7
GAST
GCKR
GDA
GDF15
GDNF
GEM
GGT1
GJB4
GLRX
GOLT1A
GPR172B
GPRC5A
GREB1
GRIN3B
GRIP2
HAP1
HCAR3
HIST1H1C
HIST1H2AC
HIST1H2AE
HIST1H2BC
HIST1H2BD
HIST1H2BG
HIST1H3D
HIST1H4H
HIST2H2BE
HIST2H2BF
HLA-G
HMOX1
HPGD
HRASLS
HSD17B14
HSD17B2
HSPB8
ICAM1
IGFL1
IGFN1
IGSF22
IL13RA2
IL1B
IL1RL1
IL23A
IL36B
IL6
IL8
ILDR1
INSC
KC6
KCNG1
KCNN4
KHDC1L
KIAA1239
KIAA1683
KIF26A
KISS1
KLHL34
KLK10
KLK14
KLK6
KPNA7
KPRP
KRT13
KRT19
KRT23
KRT34
KRT37
KRT38
KRT4
KRT7
KRT78
KRT80
KRT81
KRTAP19-1
KYNU
LBH
LCE1A
LCE1B
LCE1D
LCE1E
LCE1F
LCE2A
LCE3A
LCE3D
LCE3E
LCE6A
LCN2
LDB3
LEMD1
LGI2
LIF
LINC00086
LINC00303
LOC100049716
LOC100128342
LOC100129617
LOC100130331
LOC100287036
LOC100287082
LOC100289251
LOC100505623
LOC100505639
LOC100505710
LOC100505974
LOC100505994
LOC100506328
LOC100506377
LOC100506411
LOC100506801
LOC100506810
LOC100507025
LOC100507065
LOC100507140
LOC100507145
LOC100507452
LOC100653024
LOC145757

TABLE 6-continued

Conserved UVR signature genes in response to 30 mJ/cm² UVR among different keratinocyte lines LOC151475
LOC152225
LOC284080
LOC284804
LOC285095
LOC388282
LOC440993
LOC643401
LOC646329
LOC692247
LOC728741
LOC728975
LRRC4
LYPD5
MAP1LC3A
MARCO
MCHR1
MEOX1
MESP1
MIR23A
MIR29A
MIR614
MME
MMP1
MMP3
MSH4
MSX1
MUC20
MUC3A
MUM1L1
MYBPHL
MYH16
MYO7A
MYPN
NCCRP1
NCF4
NDRG4
NFE2
NKAIN4
NKD2
NLGN3
OCLN
OXER1
PADI1
PAPL
PCDH1
PCDHAC1
PCDHGB8P
PDE4C
PDE9A
PDGFRA
PIK3R5
PKD2L2
PLA2G10
PLA2G16
PLA2G2F
PLA2G4C
PLAC8L1
PLEKHB1
PNLIPRP3
PNMAL1
POLD4
POSTN
POU4F1
PRPS1L1
PRR9
PRSS22
PRSS27
PSCA
PSG2
PSG6
PSG7
PTCH2
PTGS2
PTPN22
PVRL4
RAB6B
RASSF5
REN
RET
RGS16
RNASE7
RNF182
RNF222
RNF223
RNF224
RPLP0P2
RPTN
RRAD
RRAGD
RUNDC3A
S100A12
S100A5
S100A6
S100A7
S100P
SALL4
SCARF1
SCARNA16
SCG2
SCN3B
SCNN1B
SCNN1D
SCNN1G
SEMA3B
SERPINB1
SERPINB2
SHBG
SHC2
SHC4
SIGLEC15
SLAMF7
SLC22A14
SLC25A41
SLC25A45
SLC40A1
SLC44A4
SLC6A14
SLC6A20
SLC6A9
SLC7A11
SLCO2A1
SLPI
SMOC1
SNORD119
SNX32
SOD3
SPNS2
SPP1
SPRR2B
SPRR2G
SPRR3
SPRR4
STC2
STRC
STX16-NPEPL1
SULT1A1
SULT1A2
SYNPO2L
SYT5
TCTEX1D4
TIMP2
TJP3
TLCD2
TM4SF19
TMEM125
TMEM22
TMEM38A TABLE 6-continued Conserved UVR signature genes in response to 30 mJ/cm² UVR among different keratinocyte lines TMEM40
TMEM88
TMIE
TMPRSS11B
TMPRSS11E
TMPRSS13
TNFAIP2
TNFRSF10C
TNXB
TP53INP2
TREML1
TRIM63
TRPV3
TSPAN1
TTC9
UCA1
UPK2
USP2
USP44
VAV1
VNN1
VWCE
ZEB2
ZMYND15
ZNF425
ZP4
ZPLD1
ZSCAN1
ZSCAN4

Example 6

Similarities Between UVR Transcriptomic Signature and Human SCC Signature

Compelling evidence supports that UVR is the main etiological factor in SCC pathogenesis. (Fartasch 2012) To test whether the identified UVR signature genes were dysregulated in human SCCs, we performed similar RNA-Seq analyses to generate DEGs in human SCC tumor tissues compared to matched normal skin tissues from patients with SCC tumors in the upper back or facial areas. We then performed gene set enrichment analysis (GSEA) (Subramanian 2005) between the UVR signature gene set and the SCC DEG set to determine the enrichment of the UVR signature in the SCC signature, or vice versa. As shown in FIG. 4A and FIG. 4B, GSEA analyses revealed a significant mutual enrichment between the UVB signature and the SCC signature (p=0.006 and 0.02, respectively). When we used a SCC signature discovered by microarray-based analyses (Hudson 2010), we observed a significant enrichment between the SCC signature and our UVR signature as well (p=5.19e-05 by fisher exact test analysis), reinforcing the molecular similarities between UVR signature and SCC signature.

To test whether the identified UVR signature is specific for skin cancer, we performed additional GSEA analyses to compare the UVR signature with gene sets dysregulated in 14 other human cancer types (obtained from the TGCA RNA-Seq database). Each cancer type contained at least six pairs of matched primary tumor and normal control tissues (Table 7). Using paired t-test, we generate DEG sets specific for each cancer type using RNA-Seq data from matched primary tumor and normal tissues. Each of resulting cancer DEG set was then used in GSEA analyses to assess the mutual enrichment between the UVR signature and the respective cancer DEG set. As summarized in Table 7, there was no significant enrichment between the UVR signature and DEG sets of other cancers (p >0.05) except for thyroid cancer (p=0.0222, Table 7). The similarity between the UVR signature and thyroid cancer-specific gene set might be related to the fact that ionizing radiation is a significant risk factor for thyroid cancer (Boice 2005) and that UVR and other radiations may share common gene signatures involved in pathways such as DNA damage and inflammation. A recent prospective study also found a non-linear association between UVR and thyroid cancer (Lin 2012). Further studies are warranted to determine whether UVR may truly increase thyroid cancer risk.

TABLE 7

Summary of GSEA results between UVR signature genes and gene sets dysregulated in different human cancer derived from the TCGA database.

| Cancer tissue origin | # of matched tumor/normal samples | NES of tumor gene set on UVR signature genes | NES of UVR signature genes on tumor gene set | Average NES | p-value (lower T = F) |
| --- | --- | --- | --- | --- | --- |
| Bladder | 19 | −2.96 | −1.93 | −2.445 | 0.993 |
| Breast | 110 | −3.11 | −1.43 | −2.27 | 0.988 |
| Colon | 41 | −1.47 | −0.762 | −1.116 | 0.868 |
| Head & Neck | 40 | −1.87 | −1.46 | −1.665 | 0.952 |
| Kidney (renal) | 72 | 1.64 | 1.47 | 1.555 | 0.06 |
| Kidney (papillary) | 32 | −0.999 | −1.22 | −1.1095 | 0.866 |
| Liver | 50 | −3.19 | −2.17 | −2.68 | 0.996 |
| Lung (adeno) | 57 | −2.54 | −1.41 | −1.975 | 0.976 |
| Lung (Squamous) | 50 | −3.29 | −1.96 | −2.625 | 0.996 |
| Prostate | 52 | −1.42 | −1.44 | −1.43 | 0.924 |
| Rectal | 8 | −0.944 | −1.08 | −1.012 | 0.844 |
| Stomach | 29 | −1.85 | 0.356 | −0.747 | 0.772 |
| Thyroid ** | 59 | 2.17 | 1.85 | 2.01 | 0.0222 |
| Uterine | 23 | −3.35 | −1.1 | −2.225 | 0.987 |

NES: normalized enrichmetn score

To test the stability of the UVR transcriptomic signature over an extended period after exposure, we performed RNA-Seq on keratinocytes exposed to 30 mJ/cm$^2$ of UVR to generate a UVR-induced DEG list at Day 21 after exposure. Cross comparison of the UVR signature with the D21 DEG list revealed an overlap of 144 genes (FIG. 4C and Table 8) ($p<2.2e-16$ per Fisher's exact test), suggesting that a significant portion of the UVR signature genes maintained their initial UVR responsiveness long after exposure. Similar analyses revealed that the UVR transcriptomic signature gene set were significantly enriched in two SCC-specific DEGs sets ($p<2.2e-16$ per Fisher's exact test) (FIG. 4D and FIG. 4E), highlighting their potential as biomarkers in UVR damage assessment and skin cancer risk prediction.

TABLE 8

Overlapping genes between UVR transcriptomic gene set and the DEG set from 21 days after UVR exposure ADAMTS14
ANGPTL4
ANKRD20A5P
ANKRD56
ARHGAP30
ATG9B
BCAN
C10orf10
C14orf34
C15orf52
C1orf68
C20orf195
C7orf10
CAPN12
CCDC62
CD8A
CEACAM1
CLDN4
CLDN7
CLEC18B
CLEC3B
CRCT1
CRYM
CSF3
CST6
CT62
CYGB
DEFB1
DPP4
ENTPD3
FER1L4
FLJ43663
FLNC
FUT3
GAD1
GDA
GLRX
GOLT1A
GPR172B
GRIP2
HCAR3
LOC152225
LOC646329
HIST1H2AC
HIST1H2AE
HIST1H2BC
HIST1H2BD
HIST1H2BG
HIST1H3D
HIST1H4H
HIST2H2BE
HIST2H2BF
HMOX1
HSD17B2
ICAM1
IL13RA2
IL1RL1
IL23A TABLE 8-continued Overlapping genes between UVR transcriptomic gene set and the DEG set from 21 days after UVR exposure IL6
IL8
KIAA1239
KLK10
KPRP
KRT13
KRT19
KRT23
KRT7
KRTAP19-1
KYNU
LBH
LCE1F
LCE3D
LCN2
LEMD1
LGI2
LIF
LINC00086
LOC100129617
LOC100130331
LOC100287036
LOC100506377
LOC100506801
LOC100507025
LOC100507452
MCHR1
MIR23A
MME
MMP1
MMP3
MYPN
OCLN
PADI1
PCDHAC1
PKD2L2
PLAC8L1
POSTN
PRSS22
PSCA
PTCH2
PTGS2
PVRL4
RGS16
RPLP0P2
RRAD
S100A12
S100A7
SCARF1
SCARNA16
SCNN1D
SHC2
SHC4
SLAMF7
SLC22A14
SLC44A4
SPNS2
SPP1
STX16-NPEPL1
SULT1A2
TM4SF19
TMEM88
TMPRSS11E
TMPRSS13
TNXB
TREML1
VNN1

Example 7

Role of UVR Signature Genes in Skin Cancer Cell Proliferation and Viability

Project Achilles leverages both biological and computational analyses to identify genes that affect cancer cell survival and/or proliferation using a genome-wide shRNA library screening in over 200 cancer cell lines. (Cowley 2014) Based on the degree of depletion of a specific shRNA following infection into cancer cells, a depletion score is assigned to each shRNA. The depletion score is therefore inversely correlated with the role of its target gene in cancer cell survival based on the assumption that loss of a key cancer survival gene (as a result of RNAi triggered by its targeting shRNA) is detrimental to the infected cells. (Cowley 2104) Given that Achilles data were derived from loss-of-function analysis, we focused on 67 UVR signature genes that were up-regulated in both SCC cases and by UVR (FC >2). 25 of the 67 genes have been validated in the Achilles database in multiple cancer cells lines. We queried the Achilles database with these 25 genes to determine which genes may play a role in skin cancer cell proliferation and/or survival. By Wilcox test, we determined that 11 out of the 25 genes had significantly lower depletion scores in skin cancer cell lines compared to other non-skin cancer lines ($p<0.05$, Table 9), indicating that this subset of UVR signature genes may play key roles in skin carcinogenesis. The depletion scores of the shRNAs targeting these 11 genes in five skin cancer cell lines, together with the median depletion scores of the same shRNAs in non-skin cancer lines, and the p-values from Wilcox tests were summarized in Table 9. These analyses highlighted the potential of these UVR signature genes as molecular targets in future skin cancer prevention and therapeutic development.

keratinocyte lines. We further demonstrate that alterations in the mRNA expression of the UVR signature genes persisted 21 days after exposure, underscoring the stability and reliability of the identified UVR biomarker panel in future clinical applications. The UVR dose-dependent response among some of the UVR signatures genes also suggests that this novel UVR biomarker panel may offer quantitative assessments of UVR damage and stratification of individual's risk of developing skin cancer.

Figure 3:
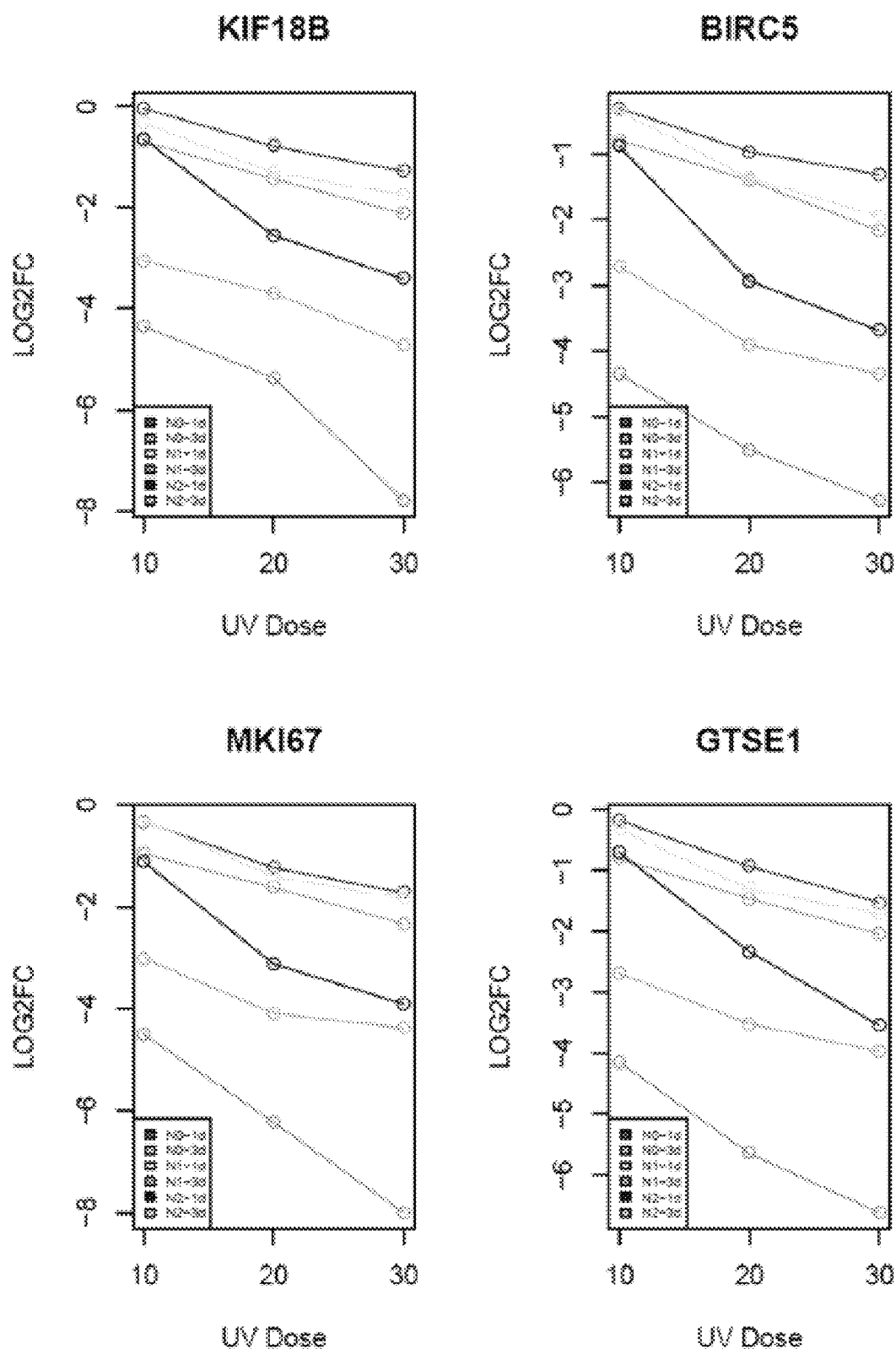
FIG. 3 shows plots of dose-dependent down-regulation (upper two panels) and up-regulation (lower two panels) of UVR-induced differentially expressed genes. Each point represents a sample at the corresponding UVR dose. X-axis represents three different UVR doses; Y-axis represents the log 2 fold change of gene expression between irradiated and non-irradiated control cells. N0-1d, N0-3d, N1-1d, N1-3d, N2-1d, and N2-3d were shown, respectively.
Figure 3:
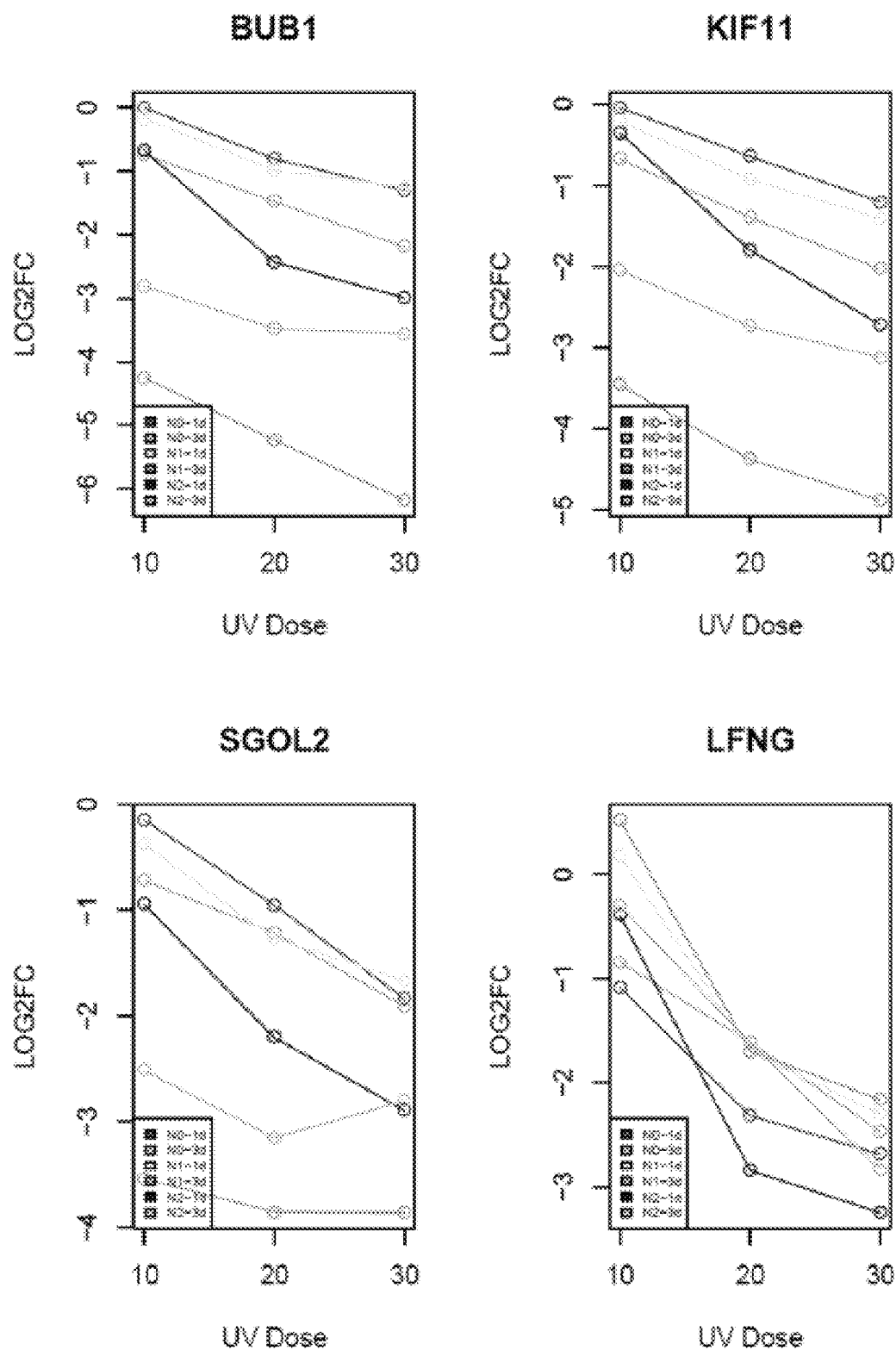
Figure 3:
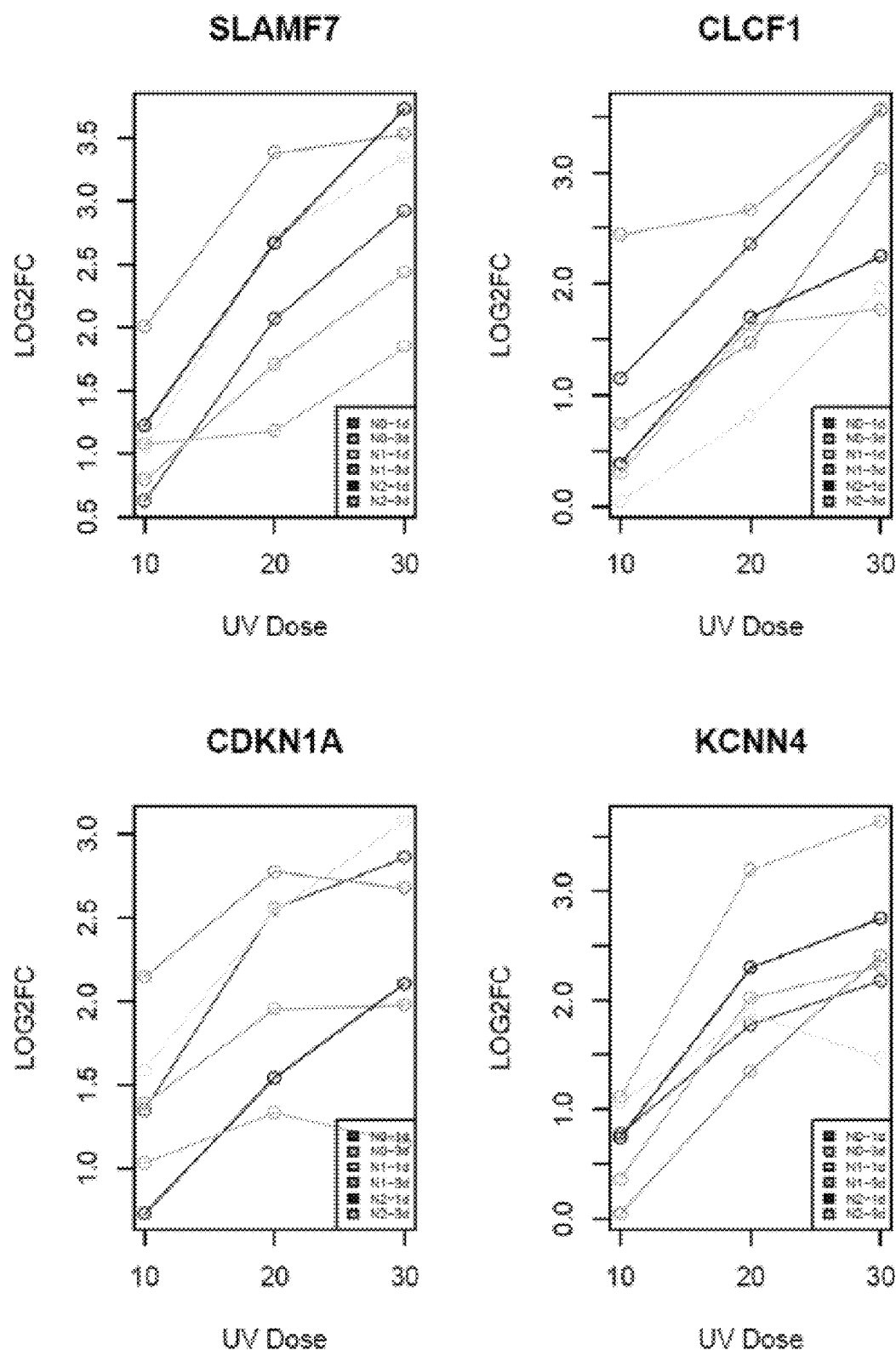
Figure 3:
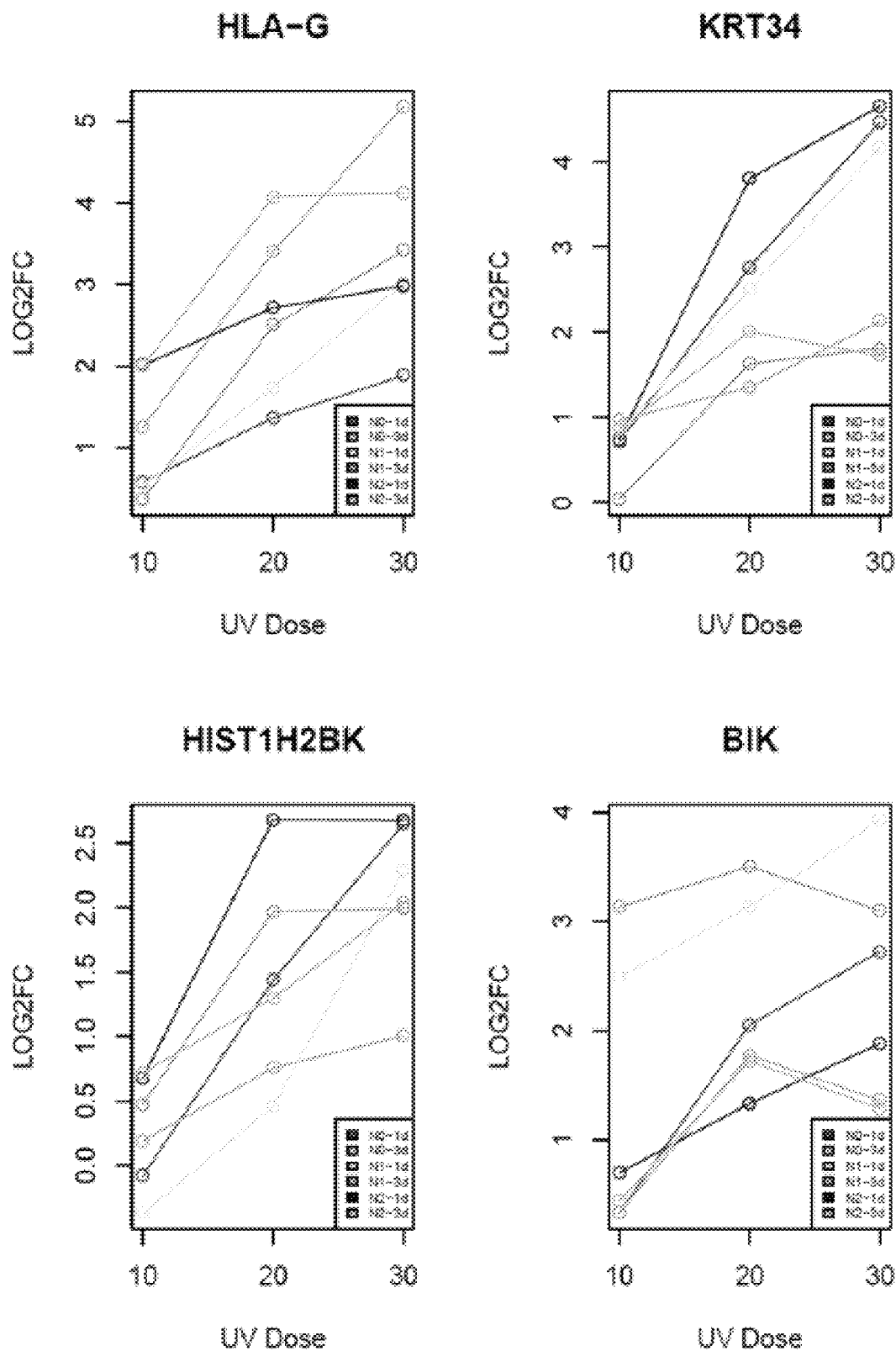

Different UVR target genes have been reported in previous studies. (Dawes 2014; da le Fuente 2009; Yang 2006; Rieger 2004; Dazard 2003; Takao 2002) Our UVR biomarker panel contains both previously identified UVR-responsive genes and many new UVR target genes, owing to the comprehensive coverage of the entire transcriptome by RNA-Seq compared to previous microarray-based analyses. Our comprehensive UVR experimental designs also provide detailed characterization of the UVR-responsive kinetics in the keratinocyte transcriptome (FIG. 2 and FIG. 3). An important application of the identified UVR biomarker panel is in sun screen testing, where it is expected provide better sensitivity and accuracy at the molecular level to replace the MED-based standard in determining the UVR-protective efficacy of sunscreen products to enhance preventative efforts to reduce risky UVR exposures. In addition, the significant similarity between the UVR signatures and SCC signatures suggests that the UVR biomarker panel may also facilitate

TABLE 9

Summary of UVR signature genes critical for skin cancer cell survival

| Genes | Skin cancer vs. other cancer lines Wilcox. test P-value | Skin Cancer Cell Lines (depletion score) | | | | | Other cancer lines (depletion score) Median |
|---|---|---|---|---|---|---|---|
| | | A2058 | C32 | COLO741 | HS944T | SKMEL5 | |
| SLPI | 0.00141 | −1.4 | −1.33 | −1.07 | −0.875 | −1.68 | −0.599 |
| KLK7 | 0.00468 | −0.311 | −0.375 | −0.962 | −0.706 | −0.93 | 0.0862 |
| KRT13 | 0.00621 | −0.439 | −0.159 | −1.18 | 0.0826 | −0.877 | 0.54 |
| NHLH2 | 0.00933 | −0.882 | −1.78 | −0.864 | −0.98 | −1.63 | −0.449 |
| GPRC5A | 0.0106 | −1.53 | −1.78 | −2.63 | −1.29 | −1.63 | −0.963 |
| HIST1H2BK | 0.0167 | −1.3 | −0.579 | −1.02 | −1.44 | −0.65 | −0.361 |
| IGFBP3 | 0.017 | 0.277 | −1.22 | 0.332 | 0.677 | 0.286 | 0.765 |
| SPOCD1 | 0.022 | −0.833 | −1.45 | −0.861 | −0.639 | −1.21 | −0.342 |
| IFI27 | 0.0273 | −0.0243 | −2.92 | −1.26 | −1.13 | −2.22 | −0.528 |
| KLK11 | 0.0286 | −1.14 | −1.63 | −0.566 | −0.914 | −1.07 | −0.577 |
| TNFSF4 | 0.0374 | −1.35 | −2.3 | −1.87 | −1.33 | −1.3 | −1.17 |

Discussion

UVR is a potent environmental carcinogen that can cause dysregulations of thousands of genes in skin cells exposed to sub-erythema UVR doses. Despite decades of research, there is no consensus panel of molecular biomarkers available for accurate assessment of UVR damage and prediction of skin cancer risk after exposure. Gene transcription is a dynamic process, which allows cells to respond and adapt promptly to environmental or physiological cues. mRNA transcripts have been successfully used as molecular biomarkers to offer early and more accurate prediction and diagnosis of disease and disease progression and to identify individuals at risk. To address the currently unmet clinical need of sensitive methods for assessing UVR damage and skin cancer risk, we employed RNA-Seq to identify UVR-induced transcriptomic signatures to establish transcriptome-based next-generation UVR biomarker panel. By means of rigorous bioinformatics and statistical analyses, we obtained a UVR biomarker panel consisting of 401 genes whose UVR-responsiveness was conserved among different clinical diagnosis and risk assessment of skin cancer in individuals following repeated sunburns or subjected to regular occupational UVR exposure. (Fartasch 2012)

Our transcriptome-based UVR biomarker panel consists of significantly more genes (401) than other biomarker panels currently used in clinical diagnosis of various diseases. (You 2015; Zanotti 2014; Gyorffy 2015) Due to the steep decreases in RNA-Seq run times and costs, profiling an individual's transcriptome has also become a feasible clinical undertaking within a reasonable time frame. A larger biomarker panel will undoubtedly offer better coverage and accuracy in assessing UVR impact and cancer risk. To facilitate future clinical and industrial applications of the UVR biomarker panel, computational algorithms can be developed to automate transcriptomic data analysis to quantify UVR damage and generate risk scores. With more transcriptomic data being generated and incorporated into the UVR transcriptomic data sets, continuous improvement and perfection of the algorithm can be achieved to produce more accurate risk reports. In addition, skin type-specific algorithms can be developed to generate more precise UVR sensitivity and risk report. We anticipate that the UVR transcriptomic signature panel together with the ever-improving RNA-Seq and bioinformatics tools will offer sensitive and reliable next-generation diagnostic tools to help enforce effective skin cancer prevention, pinpoint individual's susceptibility to UVR, identify skin cancer early, and monitor health status and therapy success to reduce skin cancer-related illness and healthcare costs.

Second Series of Experiments

Example 8

Introduction

Gene and environment interactions play pivotal roles in human disease pathogenesis and etiology. Skin serves as the major barrier structure between the body and the environment to protect the body from environmental stressors. Skin has also been shown to function as a peripheral neuroendocrine organ that regulates both local and global homeostasis through its melatoninergic system, steroidogenic system, and a peripheral equivalent of the hypothalamus-pituitary-adrenal (HPA) axis. The epidermis of the skin interfaces directly with the outside environment. This strategic location makes the epidermis an ideal in vivo model organ for studying the mechanisms underlying gene and environment interactions in development and human diseases. Frequent exposure of the epidermis to environmental carcinogens greatly increases the risk and incidence of skin cancers, including both melanoma and non-melanoma skin cancers. In fact, skin cancers are the most common cancer in the United States, affecting more people than all other cancers combined which underscores the adverse effects of direct exposure to environmental carcinogens in human health and cancer susceptibility.

Solar UV radiation (UVR) is an established environmental carcinogen in skin tumorigenesis. Excessive exposure to solar UVR, particularly its UVB component, can cause a variety of harmful effects on human skin including sunburn, photoaging, immune suppression, and increased susceptibility to cancers. The skin pigmentary system serves as the primary defense against the harmful effects of UVR. The secosteroids produced by epidermal keratinocytes can also protect against the DNA damaging effects of UVB radiation. Furthermore, UVR may alter whole-body homeostasis via activation of the skin HPA axis to increase serum levels of corticosterone. At the molecular level, UV can exert its harmful effects via DNA damage, epigenetic lesions, and dysregulated gene expression. While each of these events may arise independently, they may also impinge on each other in response to UVR. The mutagenic effects of UV have been studied extensively and the mechanisms are relatively well characterized. In contrast, the impact of UV on the epigenome and its contribution to transcriptome regulation remain poorly understood. Recent DNA methylomics studies have provided some preliminary but interesting insights into how chronic solar UVR may contribute to skin photoaging via aberrant DNA methylation. However, repeated exposures of normal human skin cells to low doses of UVR have no recognizable effects on global DNA methylation. Additional studies are needed to further elucidate the role of epigenetic mechanisms underlying the pathophysiological impact of UVR in the skin.

We and others have reported previously that acute UV exposures can cause substantial transcriptomic instability affecting thousands of genes. Our recent RNA-seq studies have generated a large cohort of UV-responsive transcriptomic data using keratinocytes from different genetic background. Furthermore, meta-analysis of the transcriptomic cohorts reveals that UV-induced changes in the transcription of a subset of genes are highly conserved and persistent over time. These findings prompt us to test whether UV may induce genetic and/or epigenetic changes to cause persistent target gene dysregulation.

In this study, we performed concurrent RNA-seq, exome-seq, and H3K27ac (histone 3 lysine 27 acetylation) ChIP-seq studies to simultaneously characterize UV-induced genetic, epigenetic, and transcriptional changes in isogenic human keratinocytes under identical UVR experimental settings. We then performed bioinformatics and statistical analyses on the resulting omics data to decipher the interactions among the genome, epigenome and transcriptome following UVR. These analyses provide new molecular insights into the complex interactions between UV and skin cells. Furthermore, comparison of the UV gene expression signature with a human squamous cell carcinoma (SCC) signature identifies several novel UV target genes for developing targeted prevention and therapy of UV-induced skin cancers.

Example 9

Materials and Methods

Human Keratinocytes, SCC Tissues and Adjacent Normal Skin Tissues.

Primary human keratinocytes from a neonatal foreskin (Caucasian donor) were obtained through the Columbia University Skin Disease Research Center (SDRC) Tissue Culture Core facility as described previously. The SDRC routinely collects neonatal foreskins from healthy newborns through the Children's Hospital at Columbia University Medical Center (CUMC) under an IRB protocol (# AAAD6866) that was approved by the CUMC Institutional Review Board. All foreskin samples were de-identified prior to being received by researchers and designated as non-human subject research under 45 CFR Part 46. UV radiation was supplied by 4 FS20T12/UVB tubes (National Biological Corp., Beachwood, Ohio), which emit UV rays between 290 and 340 nm with 75% emission in the UVB, and 25% emission in the UVA spectra, with an emission peak at 313 nm wavelength. The UVR dose was measured using an IL1700 radiometer and a SED240 UVB detector (International Light, Newburyport, Mass.) at a distance of 27 cm from the UV source to the cell culture dishes. Cells were irradiated with 30 mJ/cm2 UVR, and then collected at 4 h or 72 h after exposure. Five pairs of primary human SCC tumors with matched adjacent normal skin tissues were collected through the Molecular Pathology Shared Resource/Tissue Bank of the Herbert Irving Comprehensive Cancer Center at CUMC under IRB protocol AAAB2667. The age, gender, and race of the patients along with information on tumor stages and surgical sites of the SCC and control skin are summarized in Table 8.

RNA Isolation and RNA-Seq Analysis.

Total RNA was isolated from cultured keratinocytes, primary SCC tumors or adjacent normal skin tissues using the RNeasy Kit (QIAGEN, Gaithersburg, Md.). All RNA samples were subsequently analyzed using an RNA 6000 nano chip (Agilent Technologies, Wilmington, Del.) to confirm that the RNA integrity index was 8.0 or above. Total RNA (500 ng) from each sample was subjected to poly-A pull-down to enrich mRNAs for library preparation by using Illumina TruSeq RNA prep kit (Illumina, San Diego, Calif.). The resulting libraries were sequenced using Illumina HiSeq2000 at Columbia Genome Center. Sequencing reads were mapped to the human reference genome (NCBI/build37.2) using Tophat (version 2.0.4). Differentially gene expression (DGE) between irradiated and non-irradiated keratinocytes were determined using the DESeq software package, with a fold change (FC) cutoff set at >2 or <0.5.

H3K27ac ChIP-Seq Analysis.

For ChIP-seq studies, cells were fixed with 1% (final concentration) freshly prepared formaldehyde at 37° C. for 15 min. The fixation was stopped by incubation in 125 mM (final concentration) glycine solution for 5 min at RT. Cells were washed with PBS containing proteinase inhibitor cocktail (1x final concentration), scraped and collected as cell pellets in Eppendorf tubes. Subsequent ChIP assays and sequencing were performed by Active Motif using the H3K27ac HistonePath™ Kit following standard protocols (Active Motif, Carlsbad, Calif.). The 75-nt sequence reads generated by Illumina sequencing were mapped to the human reference genome hg19 using the BWA algorithm with default settings. Duplicate reads were removed, and the number of aligned reads ("tags") was adjusted to 24.2 million for each sample (by down sampling the larger data sets). These normalized tag files were used in all downstream analysis. ChIP-seq tags were extended at their 3'-ends to 200 bp. We used the model-based analysis of ChIP-seq (MACS) algorithm for peak calling to identify chromatin regions with H3K27ac tags compared to the input control33. Using a p-value cutoff at 1e-7, approximately 38,000 to 40,500 peaks were identified for each sample. Genes were annotated if the distance between peak-interval and gene body-interval was within 10 kb. MACS peaks (excluding promoter peaks) were used as "constituent enhancers" input into the ROSE (Rank Ordering of Super Enhancers) software to identify super enhancers (SEs). Default settings were used for the stitching (12.5 kb distance). Genes were annotated to be associated with SEs if they were within 25 kb upstream or downstream of a SE. To identify UV-induced enrichment of transcription factor (TF) motifs, we used the HOMER software for motif analysis by comparing the enhancer regions from the irradiated sample with those from the control sample.

Whole Exome-Seq (WES) Analysis.

Genomic DNA was isolated from UV-irradiated and control samples using the Wizard Genomic DNA Purification Kit (Promega). WES was performed at the Columbia Genome Center following standard Illumina TruSeq multiplexing protocol to generate targeted number of reads with more than 85% coverage of the targeted regions by =15 reads and 90% covered by =10 reads. The resulting reads were mapped to the human reference genome hg19 using the BWA algorithm with default settings. Mapped reads were sorted and indexed using the Samtools program. Duplicate reads were marked using Picard-tools. UV-induced somatic mutations between the paired UV-4h vs. control or UV-72h vs. control were called using Samtools mpileup and bcftools with default settings. Variants with fewer than 10 reads depth were discarded from the analysis.

Identification of UV Target Genes in Skin Carcinogenesis in the Achilles Database.

To identify UV target genes that are critical to skin cancer cell proliferation or survival, we queried the Achilles database with genes that were upregulated by UV. A gene was considered essential to skin cancer cell survival if their corresponding shRNAs became depleted after 40 days or 16 population doublings following shRNA infection40. We downloaded the raw normalized shRNA depletion score (DS) (Normalized shRNA value=log 2 [(Raw read value for shRNA)/(Total raw read value for Replicate)×1e6]+1) from the Achilles database. We normalized each shRNA DS by subtracting the median DS of the negative control shRNAs, including luciferase, GFP, RFP, and LacZ in the same sample. We then performed Wilcoxon tests to compare the distribution of DS among the shRNAs targeting the same gene to the distribution of the pairwise DS of all shRNAs (the null model). If the DS of shRNAs targeting the same gene was significantly similar when compared to that of the null model (p<0.1), we took the median DS of these shRNAs in the replicate samples as the gene-level DS for every cell line. Finally, we used the Wilcoxon test to identify genes whose DS was significantly lower in skin cancer cells than non-skin cancer cells (p<0.05), which were considered as skin cancer-specific cancer genes. All statistical analyses were performed using the R software package.

Immunofluorescence staining.

Primary antibodies were purchased from Abcam (SLAMF7, ab202840) or One World Lab (PTGS2, TA805307_OWL; CYP24A1: 52761_OWL; GJA5: 5361_OWL). Immunofluorescence staining was performed as we previously reported. Briefly, cultured cells on glass coverslips or frozen tissue sections (8 µM thickness) were fixed in 4% paraformaldehyde for 10 min or in cold acetone for 20 min. Fixed cells or tissue sections were then washed 3 times with PBS and then incubated with blocking buffer (0.1% Triton X-100 and 10% normal serum in PBS) for 1 h before being incubated with primary antibodies overnight at 4° C. in a humidified chamber. After 3 consecutive 5-min washes with PBS, cells or tissue sections were incubated with secondary antibodies for 1 h before being washed with PBS and mounted with gelvatol mounting media containing 4,6-diamidino-2-phenylindole dihydrochloride (DAPI). Images were acquired using a fluorescence confocal microscope (Zeiss, Thornwood, N.Y., USA).

Statistics.

Statistical analysis of each omics data set between UV-irradiated and non-irradiated keratinocytes was performed using methods included in each software package as described above. A false discovery rate <0.05 wa s used to control for false discoveries. The gene depletion scores between skin cancer cells and non-skin cancer cells were compared using Wilcoxon tests (R software package) and p<0.05 was considered significant.

Example 10

Multi-Omics Analysis of UV-Induced Molecular Abnormalities

Figure 6A:
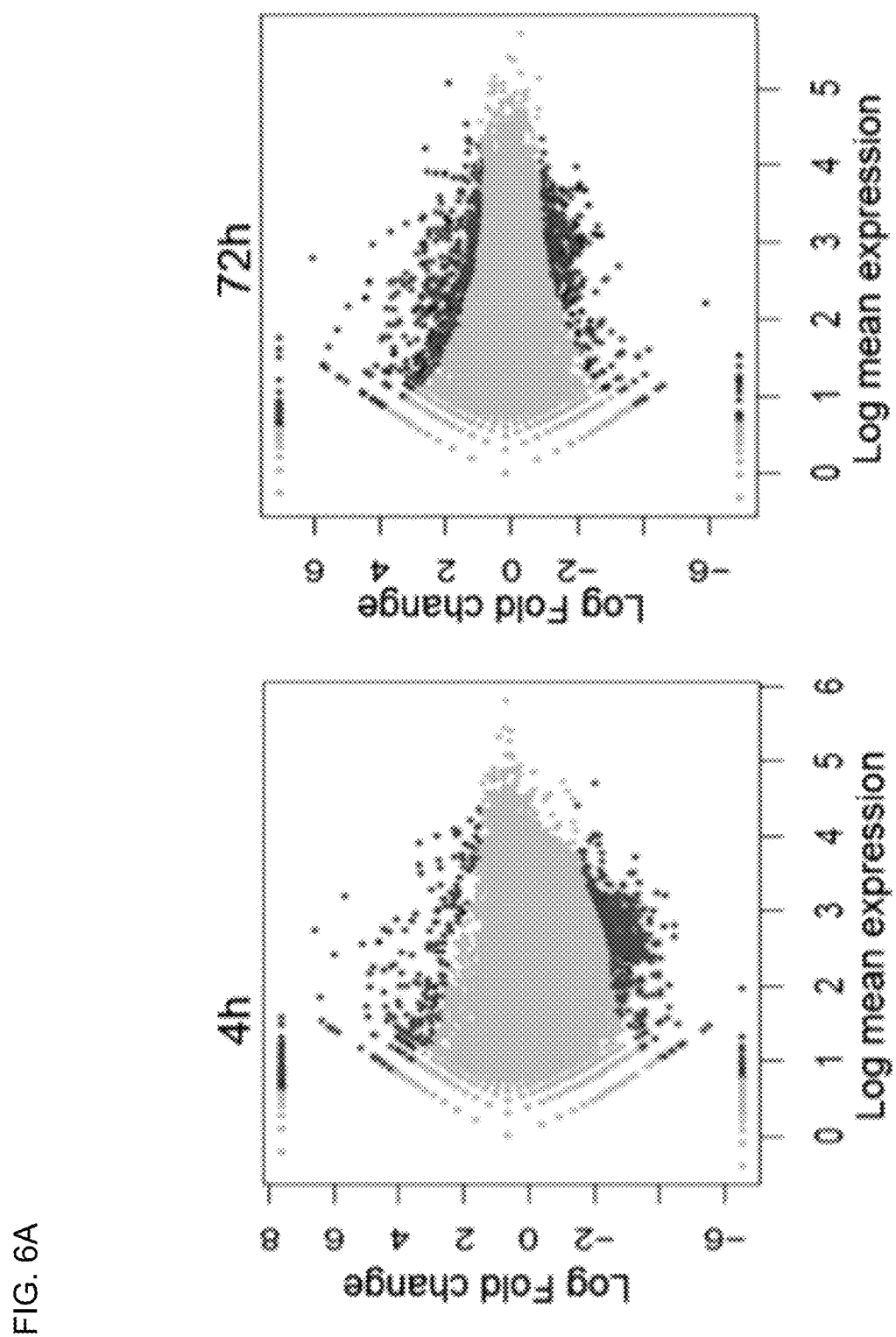
FIG. 6A shows differential gene expression plots demonstrating transcriptomic changes in human keratinocytes following UVR. DGE 4 h or 72 h following UVR and DGE that displays differential H3K27 acetylation following UVR are shown.
Figure 6B:
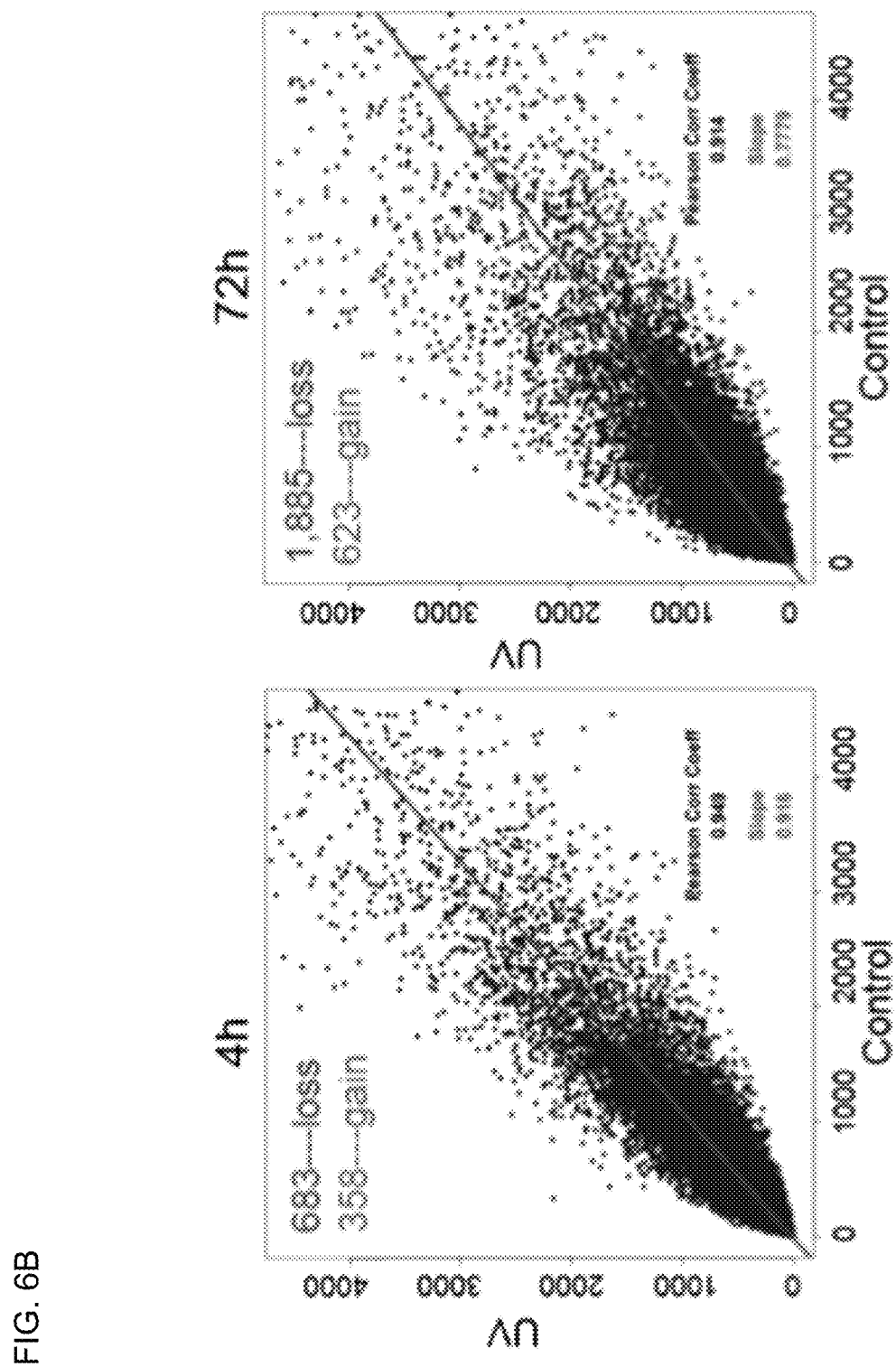
FIG. 6B shows UV induced progressive losses of H3K27ac in human keratinocytes at 4 h and 72 h after UVR. x/y-values are tag numbers in merged peak regions. Slope value <1 indicates a net loss of H3K27ac.

The mutagenic and transcriptional effects of UV have been studied extensively in the past, but relatively few studies have investigated the impact of UV on the epigenome. H3K27ac is an epigenetic mark that is frequently present at promoters or enhancers, which also separates active enhancers from poised enhancers. To test whether UV-induced differential gene expression (DGE) may be functionally linked with differential H3K27 acetylation (DHA), we performed parallel RNAseq and ChIP-seq studies to profile global DGE and DHA in UV-irradiated human keratinocytes. As shown in FIG. 6A, UV induced substantial transcriptomic changes as highlighted in the DGE plots by red or blue dots (representing significant DGEs, p<0.05). Similarly, ChIP-seq analysis revealed that UV caused a genome-wide loss of H3K27ac with regional gains in H3K27ac levels (FIG. 6B, slope value <1). T o isolate genes associated with DHA, we calculated the FC between the average peak value of H3K27ac peaks assigned to a specific gene (within 10 kb of the start or end of a nearby gene) in the UV-irradiated sample and that in the control sample. DHA was defined using a FC cutoff at 2. Altogether, we obtained 1,041 DHA genes at 4 h and 2,508 DHA genes at 72 h following UVR, suggesting a progressive genome-wide redistribution of H3K27ac marks. Genes with significant changes in both mRNA expression (DGE) and H3K27ac (DHA) are highlighted in blue in the DGE plots in FIG. 6A.

Figure 6C:
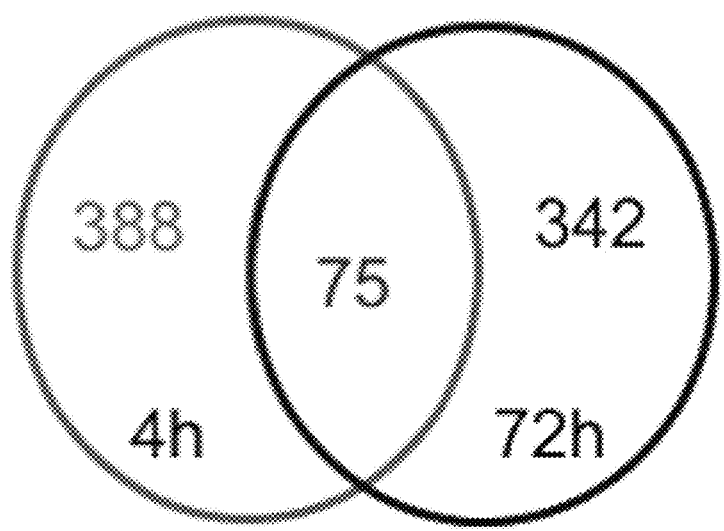
FIG. 6C shows Venn diagram showing that 75 SNVs are common between the 4 h and 72 h SNV sets.
Figure 6D:
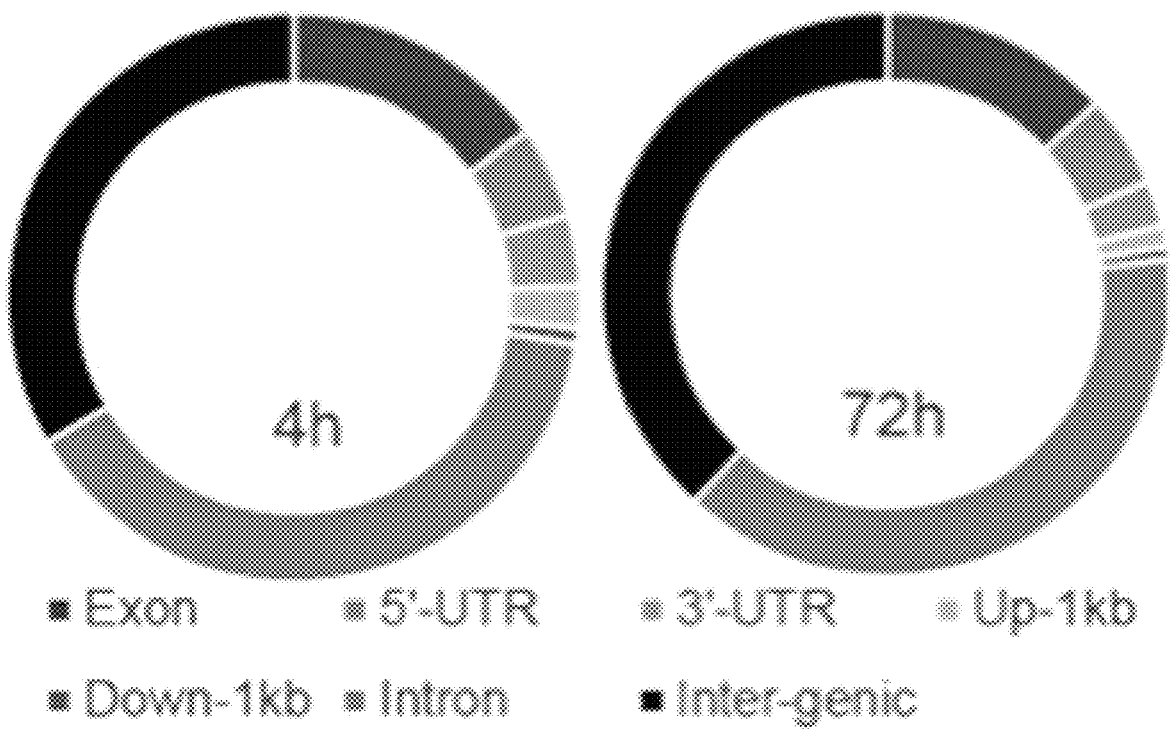
FIG. 6D shows a schematic illustration of genomic distributions of UV-induced SNVs at 4 h and 72 h after UVR.

In addition to DGE and DHA analyses, we performed concurrent WES studies using cells from the same experiment. Mutation calling using the Samtools program identified 463 and 417 single nucleotide variations (SNVs) at 4 h and 72 h (FIG. 6C, and Tables 1-3), respectively, revealing a relatively moderate mutagenic effect compared to the substantial changes in global gene expression and H3K27ac in response to UVR. There were 75 common SNVs between the 4 h and 72 h mutation profiles, with 54 of them mapped within or near genes (26 in introns, 15 in exons, 2 in the 3'-UTR, 9 in the 5'-UTR, 2 in 1 kb upstream, Table 4), and 21 in intergenic regions. Genomic distribution of UV-induced SNVs is schematically illustrated in FIG. 6D. Overall, SNVs mostly occurred in introns and intergenic regions, followed by exons, 5'-UTR, 3'-UTR, and 1 kb upstream or downstream of the genes.

Figure 6E:
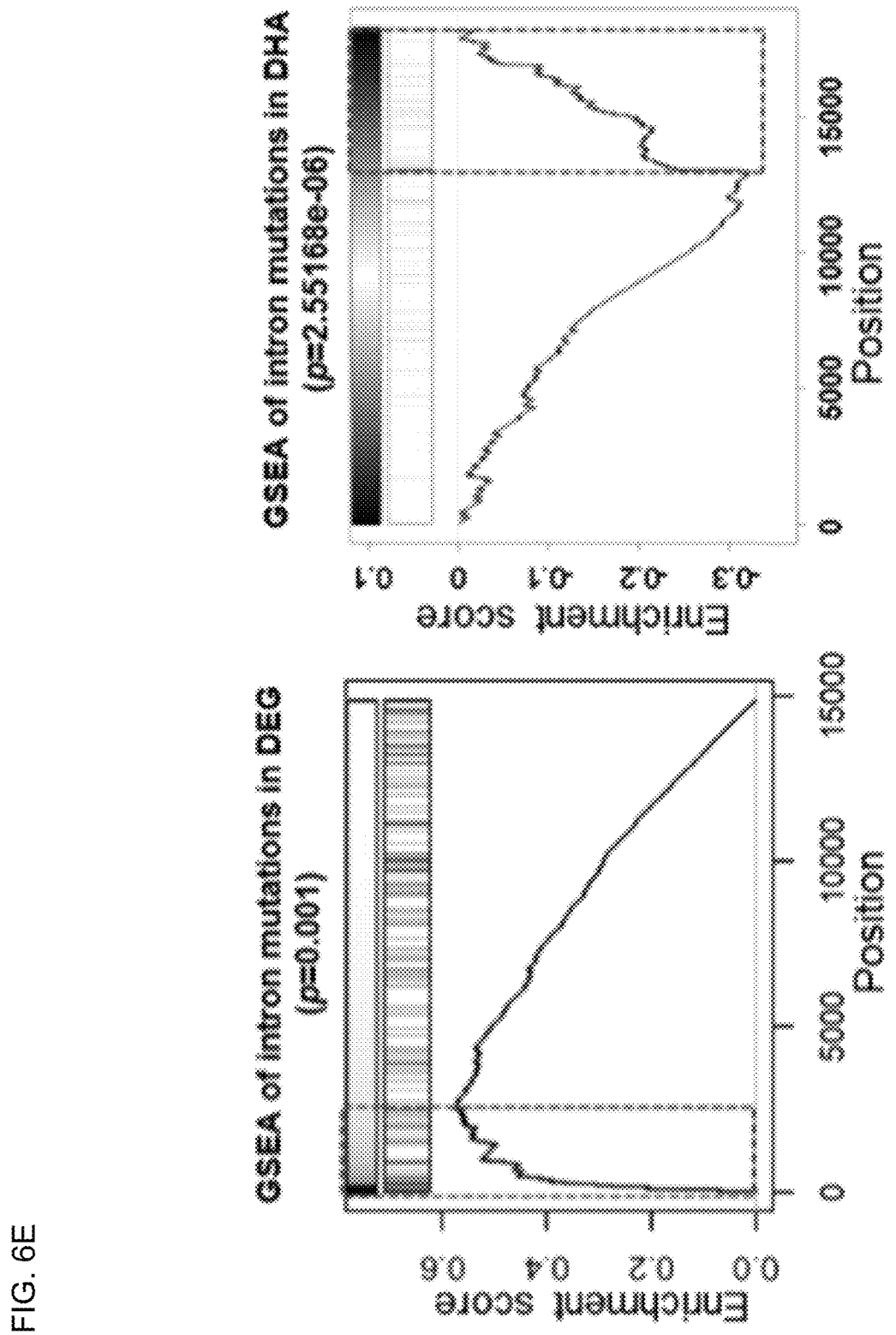
FIG. 6E shows GSEA analysis showing that genes containing intron mutations are significantly enriched in the DGE gene set (left panel) or DHA gene set (right panel) as highlighted by the dotted rectangles. GSEA was based on the Kolmogorov-Smirnov test. The p-values were estimated from permutation tests by randomly shuffling genes.

Accumulating evidence supports the role of introns in regulating gene expression through cis-acting elements. The predominant distribution of SNVs in introns and intergenic regions indicated that UV-induced mutations might alter gene activities transcriptionally. Indeed, GSEA analysis revealed that genes with intronic mutations were significantly enriched in the DGE list at 72 h after exposure (p=0.001, FIG. 6E, left panel). Among them, CYP24A1 was dramatically upregulated by UVR (Log 2FC=7). CYP24A1 is an enzyme that can metabolize vitamin D3 to generate biologically active hydroxyderivatives with efficient anti-tumorigenic activities on melanoma cells. Elevated levels of CYP24A1 are associated with increased aggressiveness and proliferative potential of colorectal and prostate tumors. Besides the effect of intronic mutation on gene expression, GSEA also revealed a significant overlap between genes with intronic mutations and genes showing reduced H3K27ac marks (p=2.6e-06, FIG. 6E, right panel), consistent with the accumulating evidence supporting the role of chromatin conformation in modulating DNA repair activity during UV-induced mutagenesis.

Example 11

UV Induced Dynamic Reorganization of Super Enhancers (SEs).

Figure 7A:
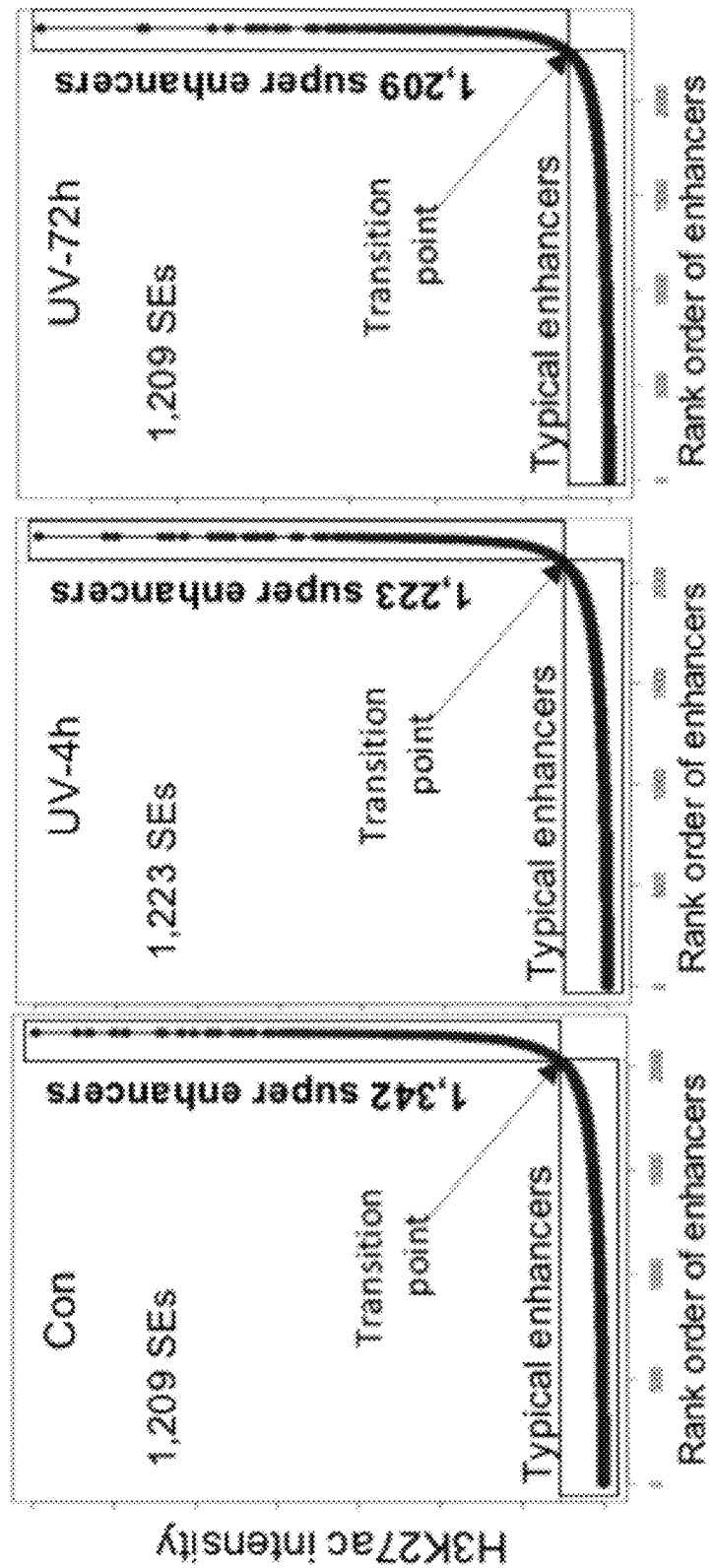
FIG. 7A shows SE profiles in control and UV-irradiated keratinocytes showing that UV decreased the total number of SEs marked by H3K27ac.
Figure 7B:
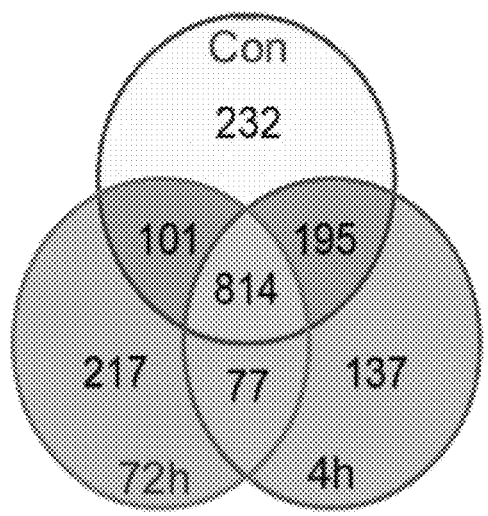
FIG. 7B shows Venn diagram showing the number of common and distinctive Ses among control, UV-4 h, and UV-72 h.
Figure 7C:
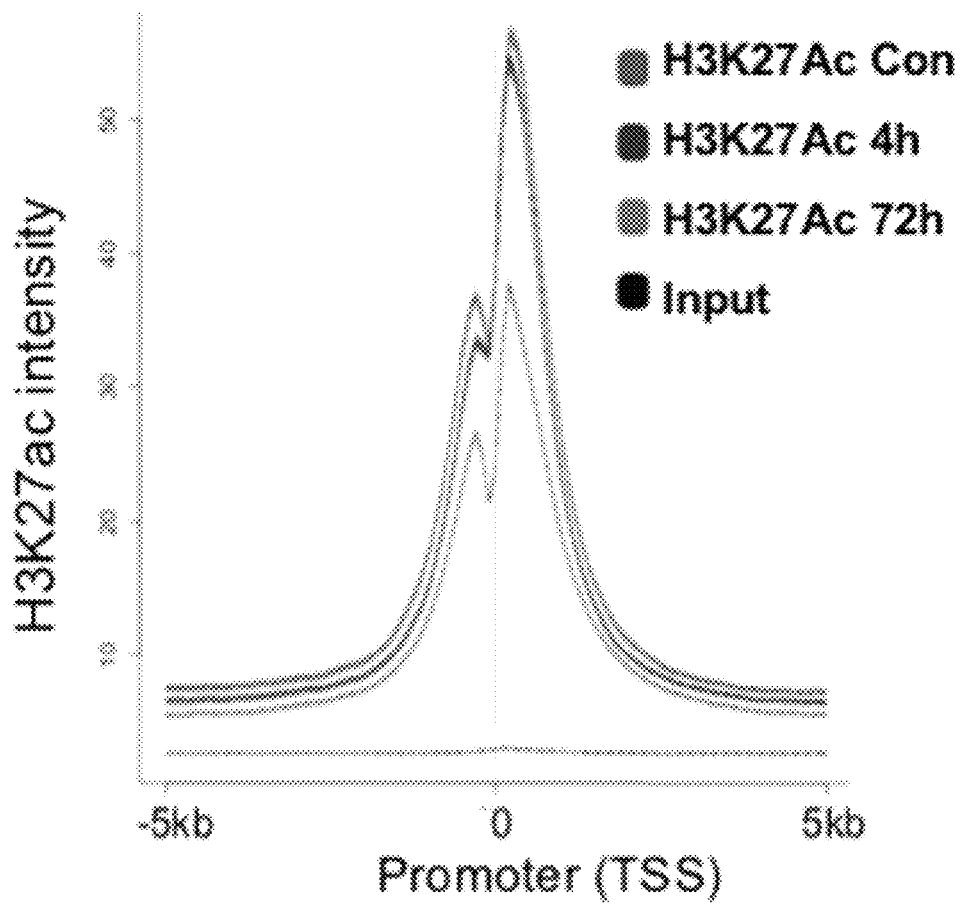
FIG. 7C shows Genome-wide H3K27ac signals in promoter regions showing a pronounced loss of 72 h following UVR.
Figure 7D:
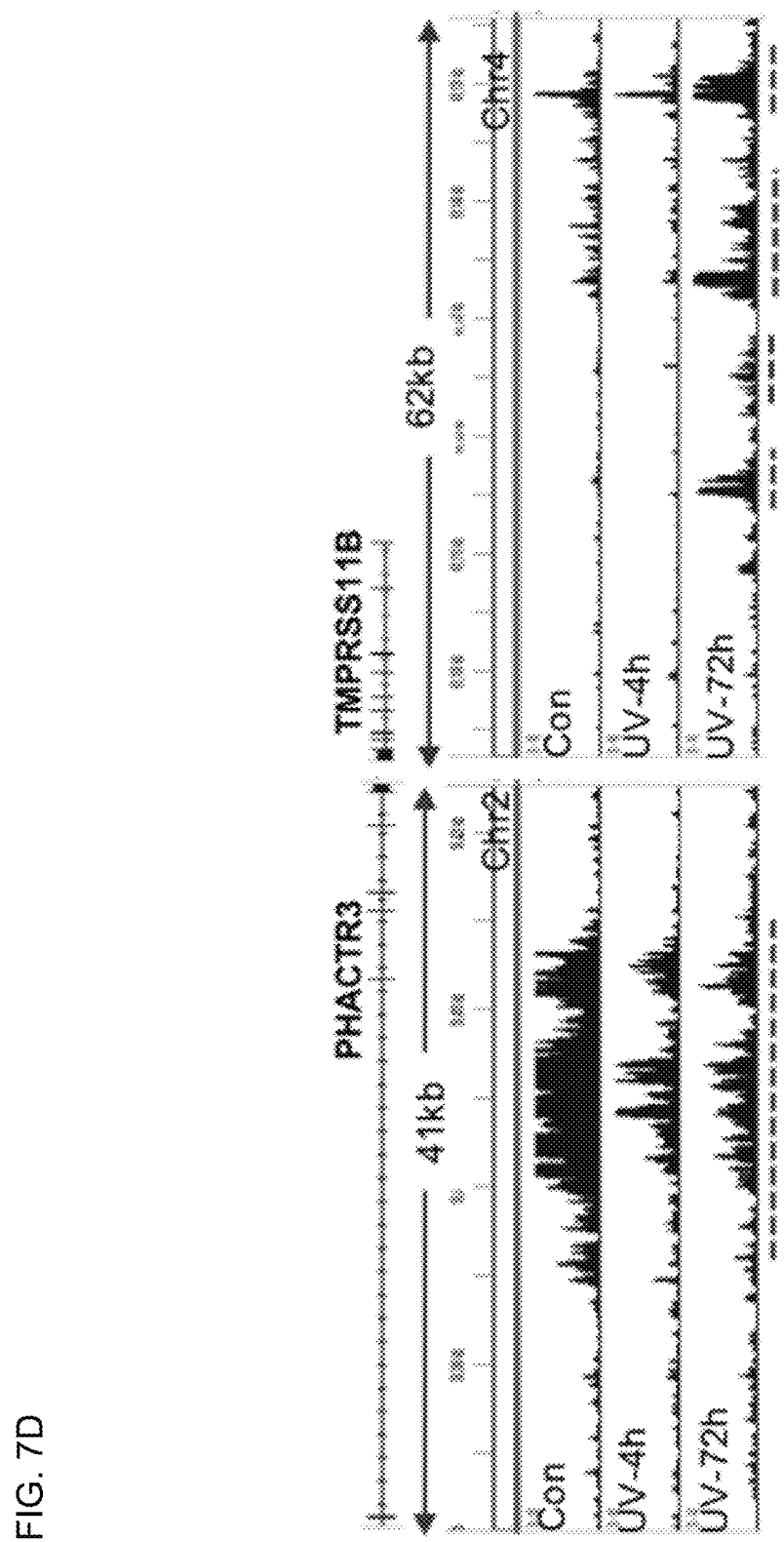
FIG. 7D shows gene tracks of H3K27ac ChIP-seq exemplifying that UVR increased H3K27ac at the PHACTR3 gene locus but reduced H3K27ac at the TMPRSS11B gene locus. PHACTR3: phosphatase and actin regulator 3; TMPRSS11B: transmembrane protease, serine 11B (HATL5).

SEs are large clusters of enhancers that regulate the activity of key genes during development and disease pathogenesis. H3K27ac is one of the best characterized epigenetic marks for mapping genome-wide SE structures. To test whether UVR may alter SEs to modulate its target gene activities, we used the ROSE algorithm to map SEs in both control and UV-irradiated keratinocytes. We sorted the enhancer regions based on their H3K27ac signals from the lowest to the highest. Enhancers whose signals were higher than the transition point of the curve (FIG. 7A) were designated as SEs. A total of 1,342 SEs were identified in control keratinocytes. Following UV irradiation, the total number of SEs decreased to 1,223, and 1,209 SEs at 4 h and 72 h after exposure, respectively (FIG. 7A), revealing a net loss of SEs following UVR. Venn diagram in FIG. 7B illustrates that UV induced 214 unique SEs at 4 h, and 294 unique SEs at 72 h after UV exposure, with 77 UV-specific SEs conserved between the 4 h and 72 h SE sets. The majority of the SEs in non-irradiated cells (814 out of 1,342), however, remained intact after UVR. Separate analyses further revealed that UVR also decreased global H3K27ac signals at promoter regions (FIG. 7C).

Next, we isolated genes associated with either the common SEs or UV-induced SEs as indicated in FIG. 7B. We used the ToppGene Suite program to identify top biological pathways in which each group of SE-associated genes were enriched. As summarized in Table 10, many of the SE-associated genes play important roles in tumorigenesis. The common SE-associated genes were enriched in integrin-dependent signaling pathways, which are essential in epidermal development and homeostasis. In contrast, genes associated with UV-induced SEs were enriched in cancer-, DNA damage-, and endocytosis-related pathways (Table 10). Examples of UV-induced changes in SEs are shown in Table 10, where UV reduced H3K27ac signal of the SE associated with PHACTR3 but increased H3K27ac signal of the SE associated with TMPRSS11B. DNA hypermethylation of PHACTR3 is frequently observed in HPV-induced immortalization of keratinocytes and in human cancers, highlighting the importance of epigenetic regulation of its activity in human diseases.

TABLE 10

Top biological pathways and relevant disease pathways in which the conserved SE-associated genes or UV-induced SE-associated genes are enriched. P-values were obtained using the hypergeometric distribution test to examine the overlap between the identified gene sets and the known pathways. Bonferroni correction was used to have adjusted p-values.

| | p-Value | Bonferroni |
|---|---|---|
| Conserved SE-associated genes | | |
| Biological pathway | | |
| α6β1 integrin signaling | 3.868E−10 | 8.598E−7 |
| Integrin signaling pathway | 6.761E−10 | 1.503E−6 |
| α6β4 integrin signaling pathway | 8.588E−10 | 1.909E−6 |
| Regulation of actin cytoskeleton | 7.360E−9 | 1.636E−5 |
| Focal adhesion | 2.159E−7 | 4.800E−4 |
| Disease relevance | | |
| Tumor Progression | 8.248E−21 | 5.306E−17 |
| Mammary Neoplasms | 9.842E−17 | 6.333E−13 |
| Malignant neoplasm of lymph node | 3.622E−15 | 2.331E−11 |
| Non-Small Cell Lung Carcinoma | 4.468E−15 | 2.874E−11 |
| Ovarian Carcinoma | 6.162E−15 | 3.965E−11 |
| UV-induced SE-associated genes | | |
| Biological pathway | | |
| Pathways in cancer | 7.319E−7 | 1.273E−3 |
| Androgen receptor signaling pathway | 1.323E−5 | 2.301E−2 |
| FOXM1 transcription factor network | 1.816E−5 | 3.158E−2 |
| DNA damage response (only ATM dependent) | 9.396E−5 | 1.634E−1 |
| Endocytosis | 1.522E−4 | 2.647E−1 |
| Disease relevance | | |
| Leukemia | 1.023E−12 | 4.460E−9 |
| Tumor Progression | 4.283E−12 | 1.867E−8 |
| Glioblastoma | 8.107E−10 | 3.534E−6 |
| Malignant neoplasm of pancreas | 5.226E−9 | 2.278E−5 |
| Pancreatic carcinoma | 1.252E−8 | 5.458E−5 |

Example 12

Functional Associations Between Global H3K27ac and Gene Expression Regulation.

Figure 8A:
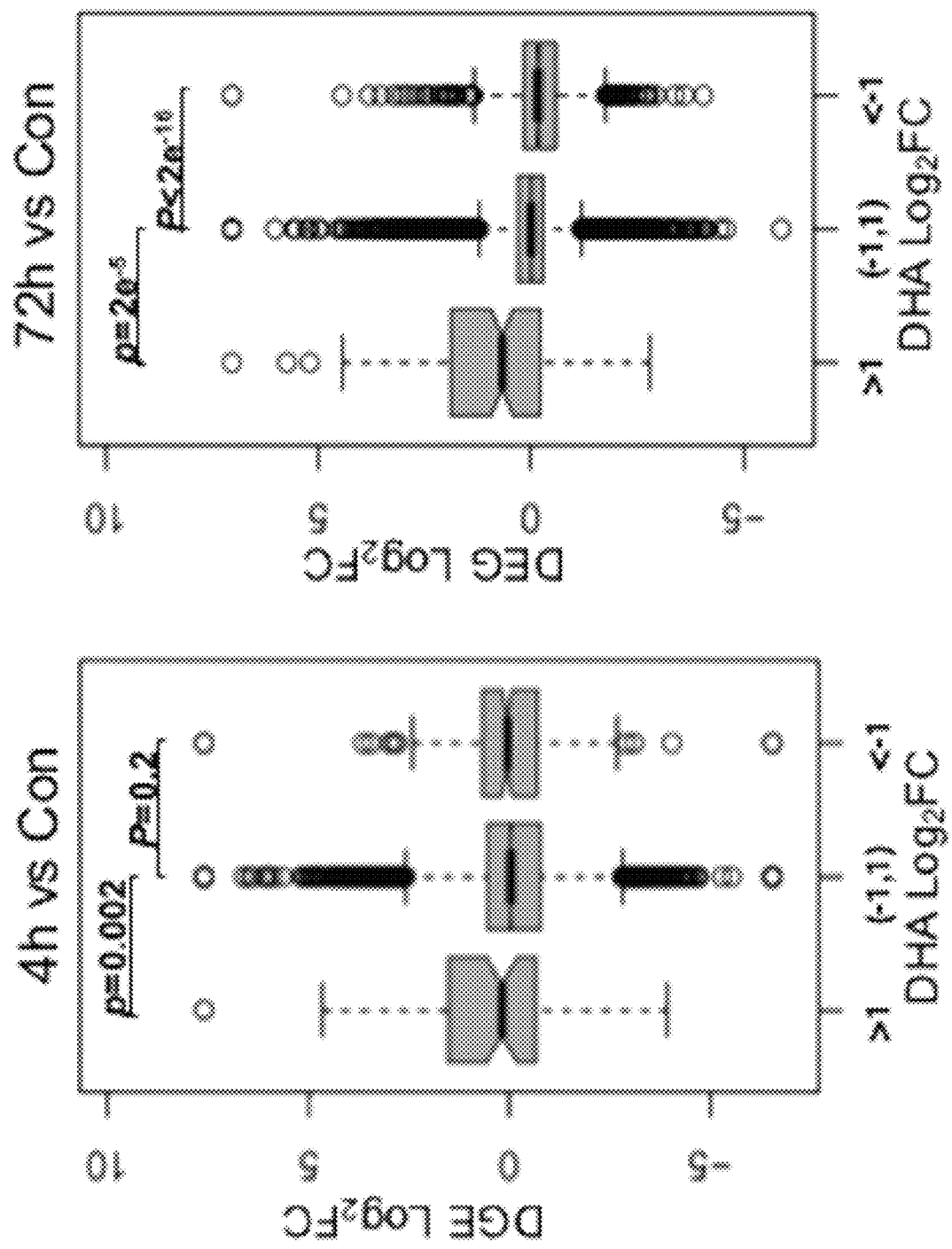
FIG. 8A shows integrative analyses of the DGE and H3K27ac DHA gene sets at 4 h or 72 h after UVR. Correlations between gene expression and H3K27ac are considered significant if p<0.05. P-values were obtained using Student's t-test by comparing the log 2FC of the expression values of the genes from the three DHA groups.
Figure 8B:
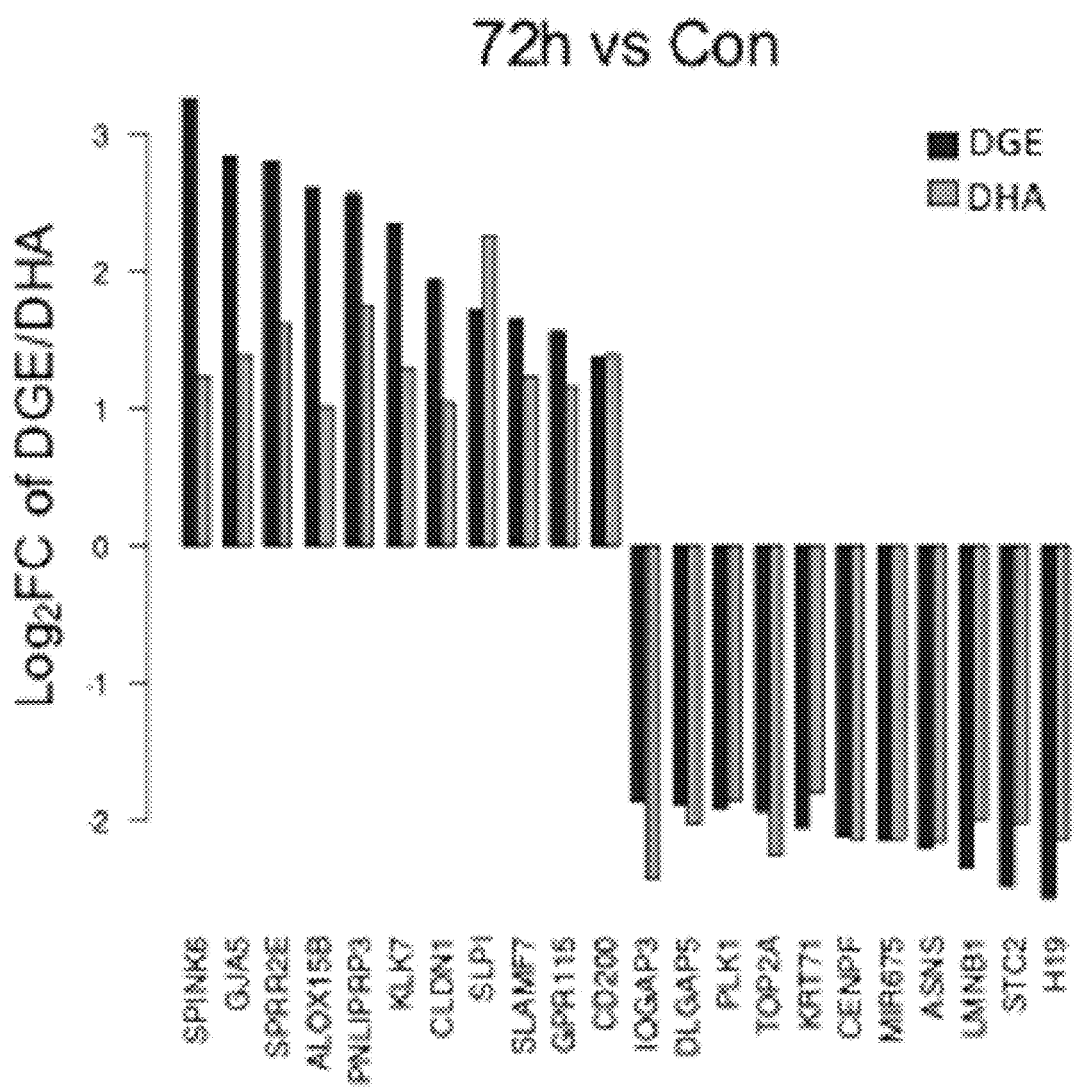
FIG. 8B shows representative genes showing concordant changes in gene expression and H3K27ac following UVR. Cutoff is set at Log 2FC>1 or <−1 for both DGE and DHA.
Figure 8D:
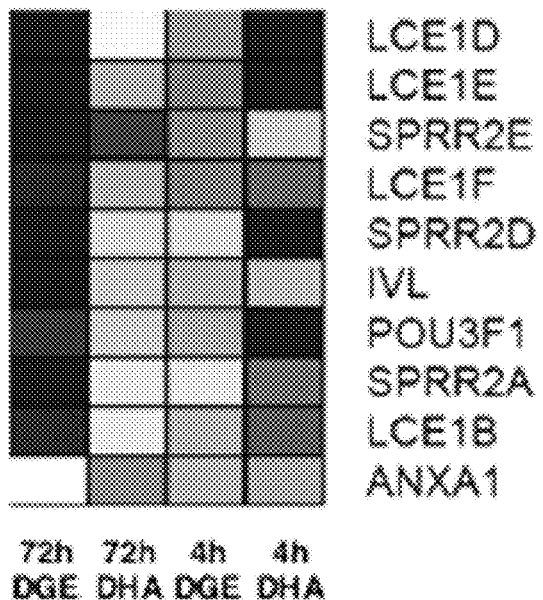
FIG. 8D shows parallel analysis of H3K27 DHA status of the DGEs that are enriched in top UV-responsive biological pathways.
Figure 8D:
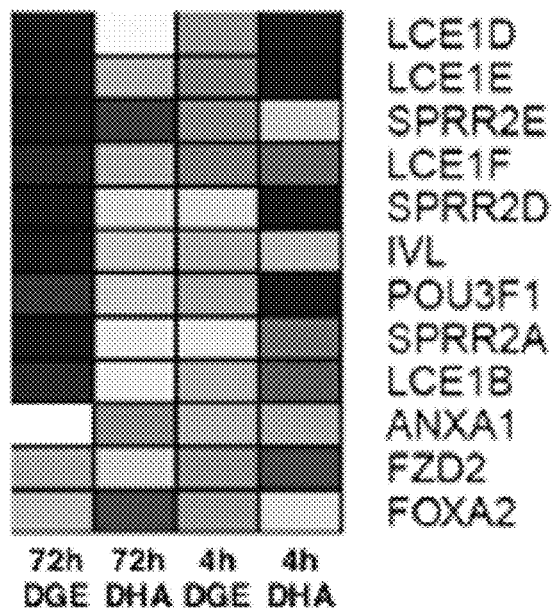
Figure 8D:
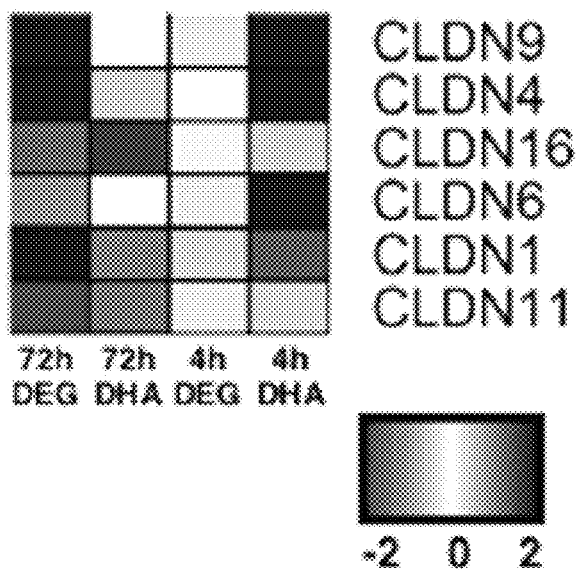
Figure 8D:
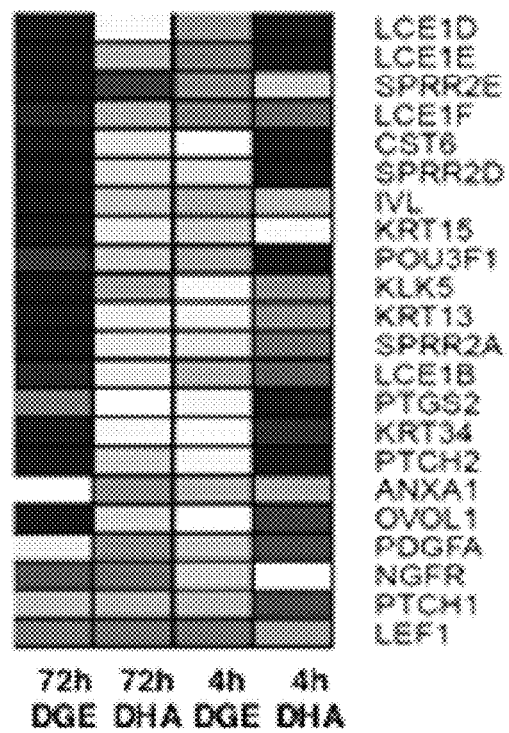

To test the impact of H3K27ac redistribution on transcriptome dysregulation following UVR, we divided DHA gene set and DGE gene set into three groups based on their respective Log 2FC values, including Log 2FC >1, Log 2FC <−1, or −1<Log 2FC <1 (which was considered less or non-responsive to UVR). We plotted UV-induced DGE set against DHA set at 4 h or 72 h using the R software package. As shown in FIG. 8A, we found significant correlations between genes showing increased H3K27ac (Log 2FC >1) and upregulated expression at both 4 h and 72 h after UVR. In contrast, significant correlations existed between decreased H3K27ac (Log 2FC <−1) and reduced gene expression only at 72 h but not 4 h after UVR, suggesting a time-dependent effect on H3K27ac change on gene expression regulation. Representative genes with concordant changes in gene expression and H3K27ac are shown in FIG. 8B. Genome-wide associations between H3K27ac and gene expression of UV target genes are summarized in FIG. 8C, where positive correlations are highlighted in pink and inverse correlations are highlighted in green. The majority of the UV-responsive genes displayed discordant changes in H3K27ac and expression regulation. DAVID Pathway analysis of the UV target genes using the DAVID program identified top-ranked UV-responsive pathways including keratinocyte differentiation, epithelial cell differentiation, calcium-independent cell-cell adhesion, and epidermal development (FIG. 8D). A parallel H3K27ac analysis of the genes involved in these pathways demonstrated, however, the regulation of their gene expression was largely independent of H3K27ac changes, suggesting that other transcription regulatory mechanisms were involved to alter UV target gene expression.

Example 13

UV-Responsive TF Motifs and Target Genes in Skin Cancer Cell Growth and Survival.

Figure 9B:
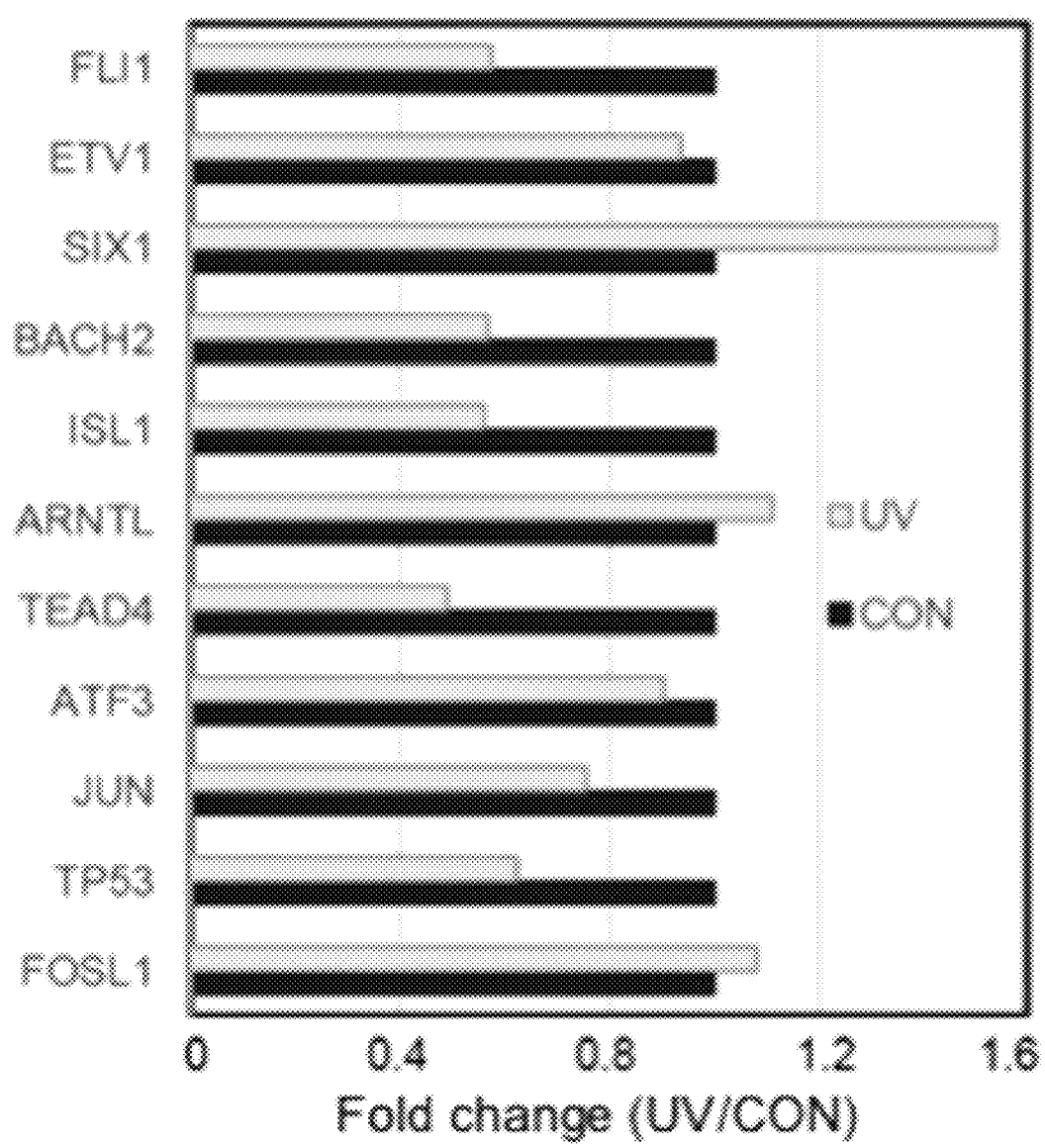
FIG. 9B provides the RNA-seq results showing mRNA expression changes of the TFs identified in FIG. 9A between UV-irradiated and control keratinocytes.

Previous chromatin accessibility analysis shows that UV can induce genome-wide chromatin compaction, which coincides with the global loss of H3K27ac after UVR. To test whether UVR-induced changes in chromatin accessibility may occur at TF binding sites, we performed TF motif analysis focusing on H3K27 DHA regions using the HOMER algorithm. We found a significant enrichment of multiple TF motifs occurred at UV-induced DHA regions (FIG. 9A), suggesting that binding of these TFs was modulated by UVR. The majority of the identified UV-responsive TFs, such as JUN, TP53 and FOSIL1, showed moderate changes in their mRNA levels (FIG. 9B). They may contribute to the differential expression of UV target genes through chromatin accessibility changes after UVR.

Figure 9C:
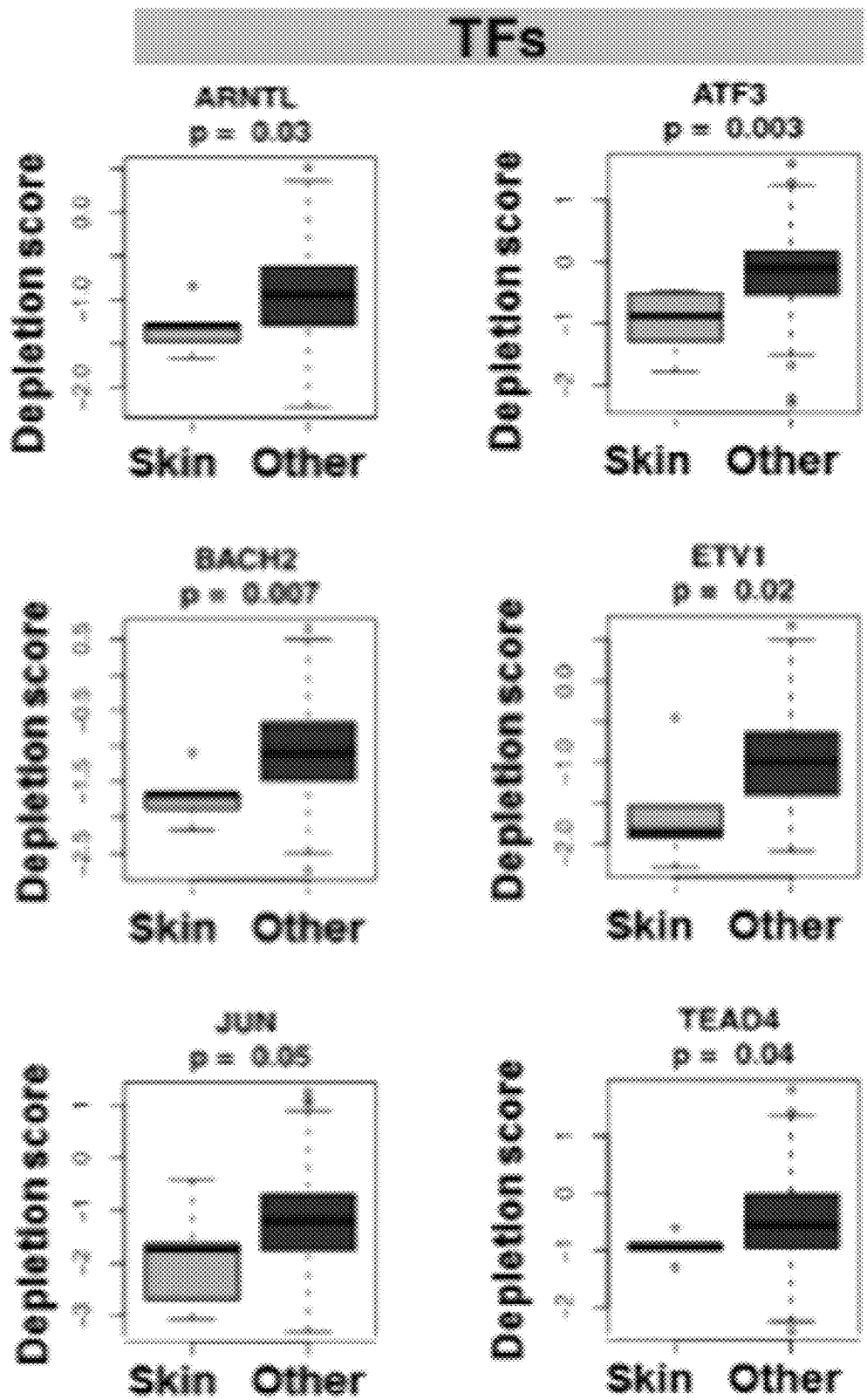
FIG. 9C shows that loss of function of selected UV-responsive TFs is significantly more detrimental to skin cancer cells than non-skin cancer cells.
Figure 9D:
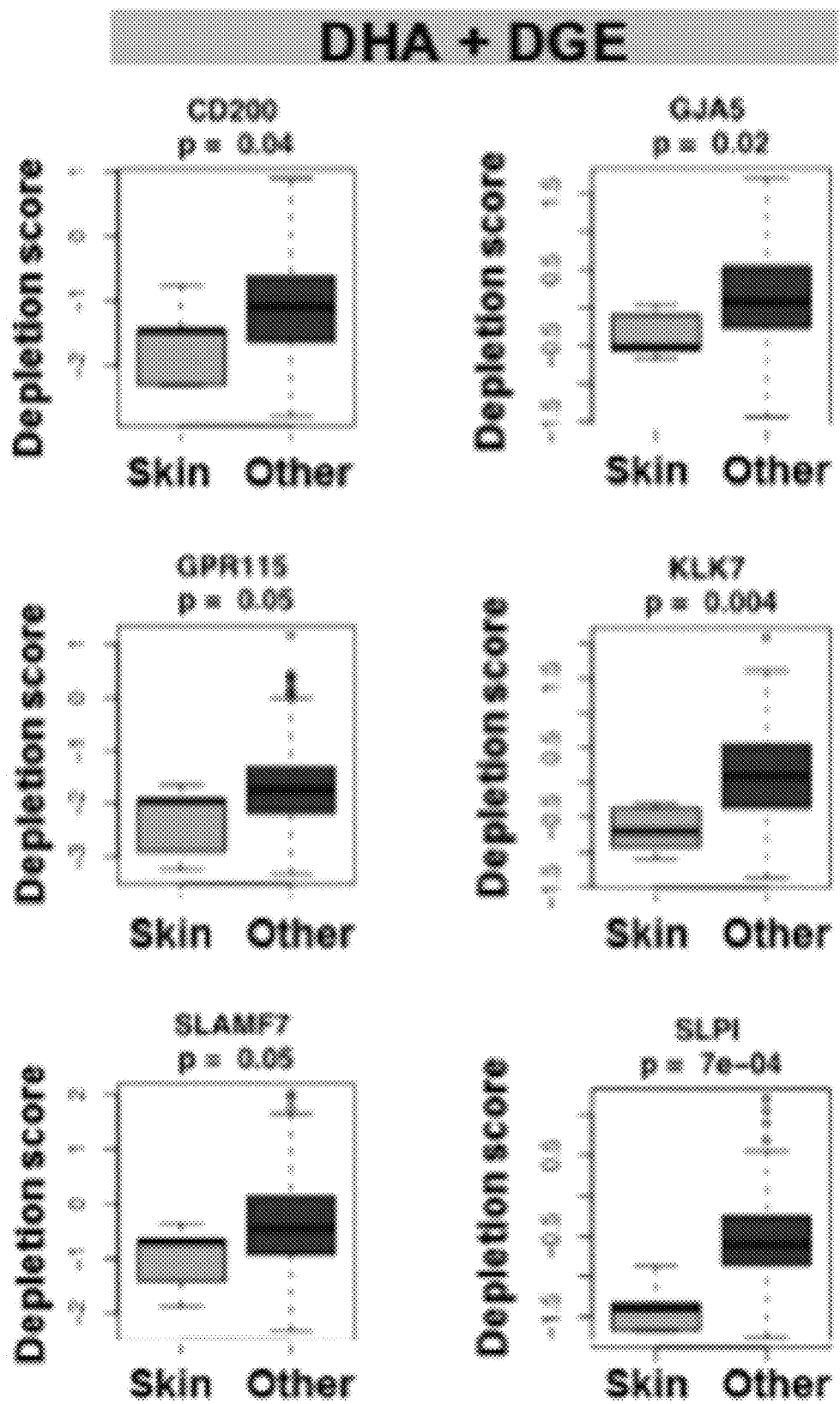
FIG. 9D shows that loss of function of selected UV target genes in FIG. 8B (more than 2-fold increases in both DGE and DHA) is significantly more detrimental to skin cancer cells than non-skin cancer cells. P-values were obtained using the Wilcoxon test by comparing the gene depletion scores between the skin cancer cells versus the non-skin cancer cells.
Figure 9E:
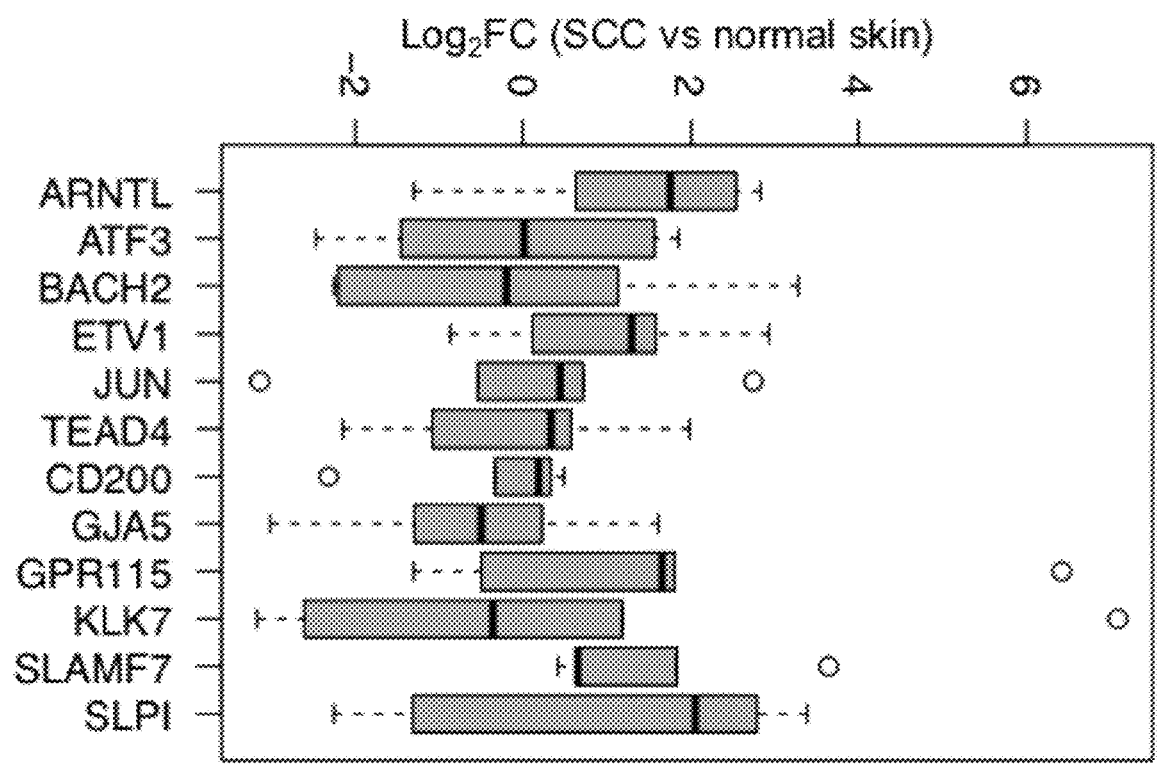
FIG. 9E is a box plot illustrating the Log 2FC in the expression of the genes shown in FIG. 9C and FIG. 9D among 5 pairs of SCC and normal skin tissues. SLAMF7, ARNTL, ETV1, and GPR115 show more consistent upregulation in SCCs.

Project Achilles focuses on identifying genetic vulnerabilities and generating high quality gene essentiality datasets and rigorous analytical tools. The Achilles database consists of experimental data on the function of selected genes in cancer cell growth and/or survival based on genome-wide shRNA screenings studies. To test the role of UV-responsive TFs in skin carcinogenesis, we queried the Achilles database for experimental evidence on which TFs are critical to skin cancer cell growth and survival. As shown in FIG. 9C, shRNA-mediated knockdown of 6 UV-responsive TFs were significantly more toxic for cutaneous melanoma cells (A2058, C32, HS944T, SKMEL5) than other types of cancer cells (p<0.05). Similarly, we queried the Achilles database to test the role of UV target genes in skin cancer growth and survival. We found multiple UV target genes to be critical to the survival of skin cancer cells, including CD200, GJA5, GPR115, KLK7, SLAMF7 and SLP1 (FIG. 9D). Given the lack of RNA-seq data on cutaneous SCCs in The Cancer Genome Atlas (TOGA), we performed RNA-seq studies on 5 pairs of cutaneous SCC tumors and matched adjacent normal skins to generate a SCC-specific DGE cohort containing genes that were dysregulated in SCCs. We then queried this SCC DGE cohort to determine the expression of the UV-responsive TF genes and UV target genes shown in FIG. 9C and FIG. 9D. As illustrated in FIG. 9E, many of these TF genes and UV target genes displayed individual variations in their DGE status among the SCC patients. SLAMF7, ARNTL, ETV1, and GPR115 were consistently upregulated in SCCs and in response to UVR, whereas GJA5 was frequently downregulated in SCCs but upregulated by UVR in keratinocytes.

Example 14

Validation of Selected UV Target Genes in Human SCCs.

Figure 10A:
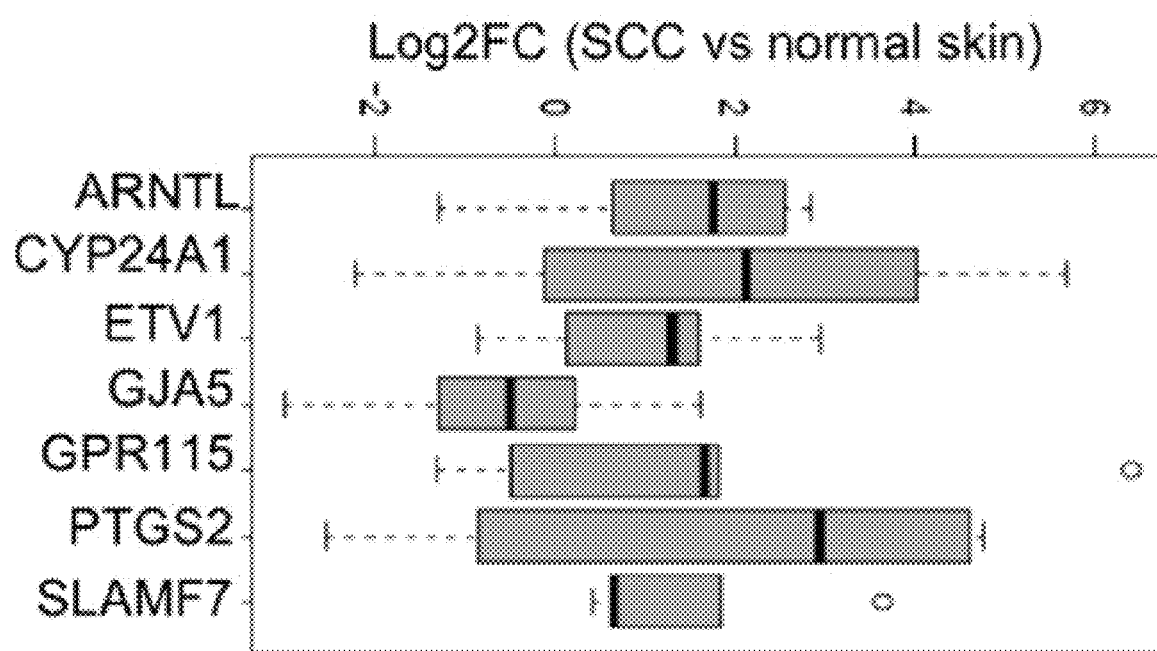
FIG. 10A is a box plot illustrating the Log 2FC in the expression of selected UV target genes between the 5 matched pairs of SCC and normal skin tissues.
Figure 10B:
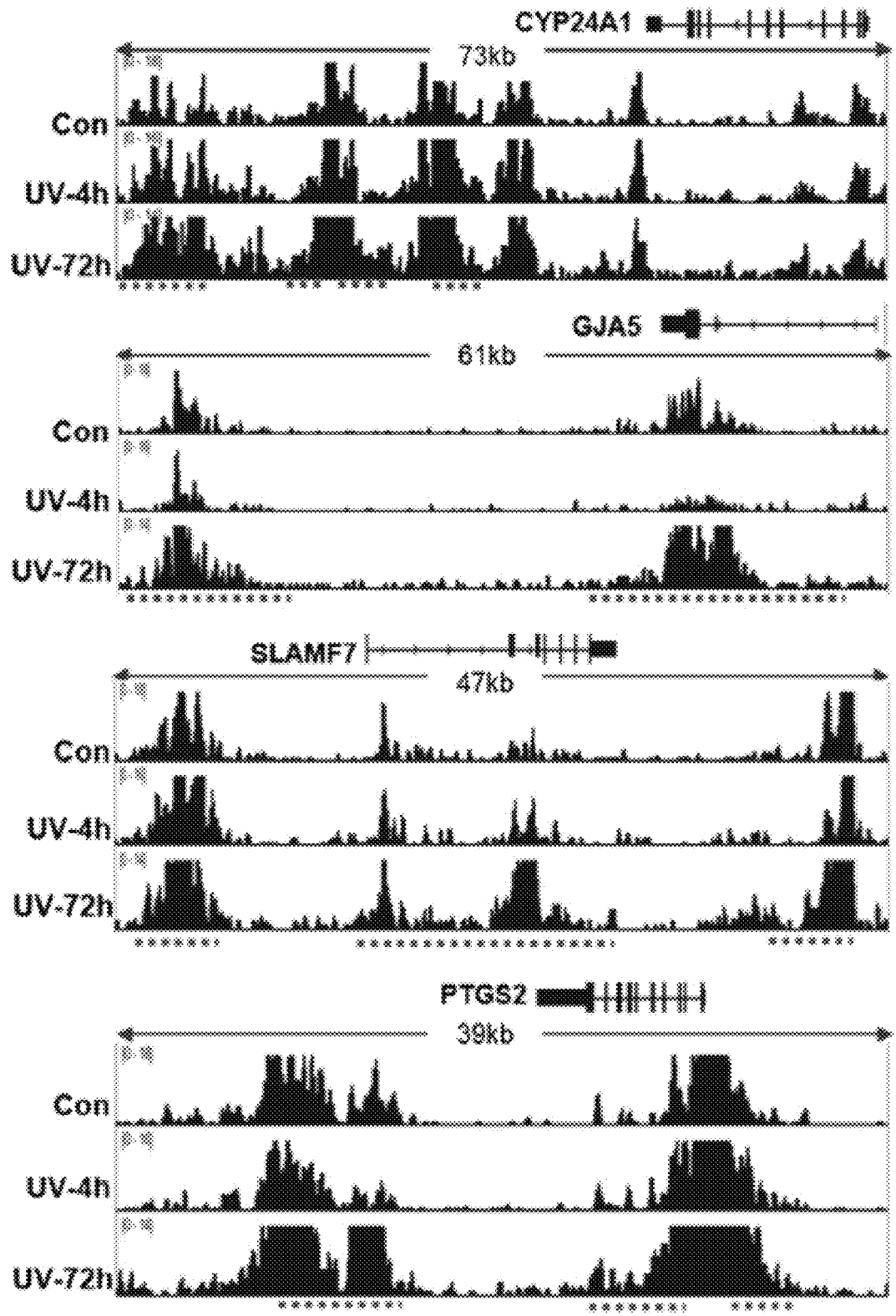
FIG. 10B provides the gene tracks of H3K27ac profiles showing that UVR increased H3K27ac levels at CPY24A1, PTGS2, GJA5, and SLAMF7 chromatin regions 72 h after UVR, which are highlighted by dotted lines under each gene track.
Figure 10C:
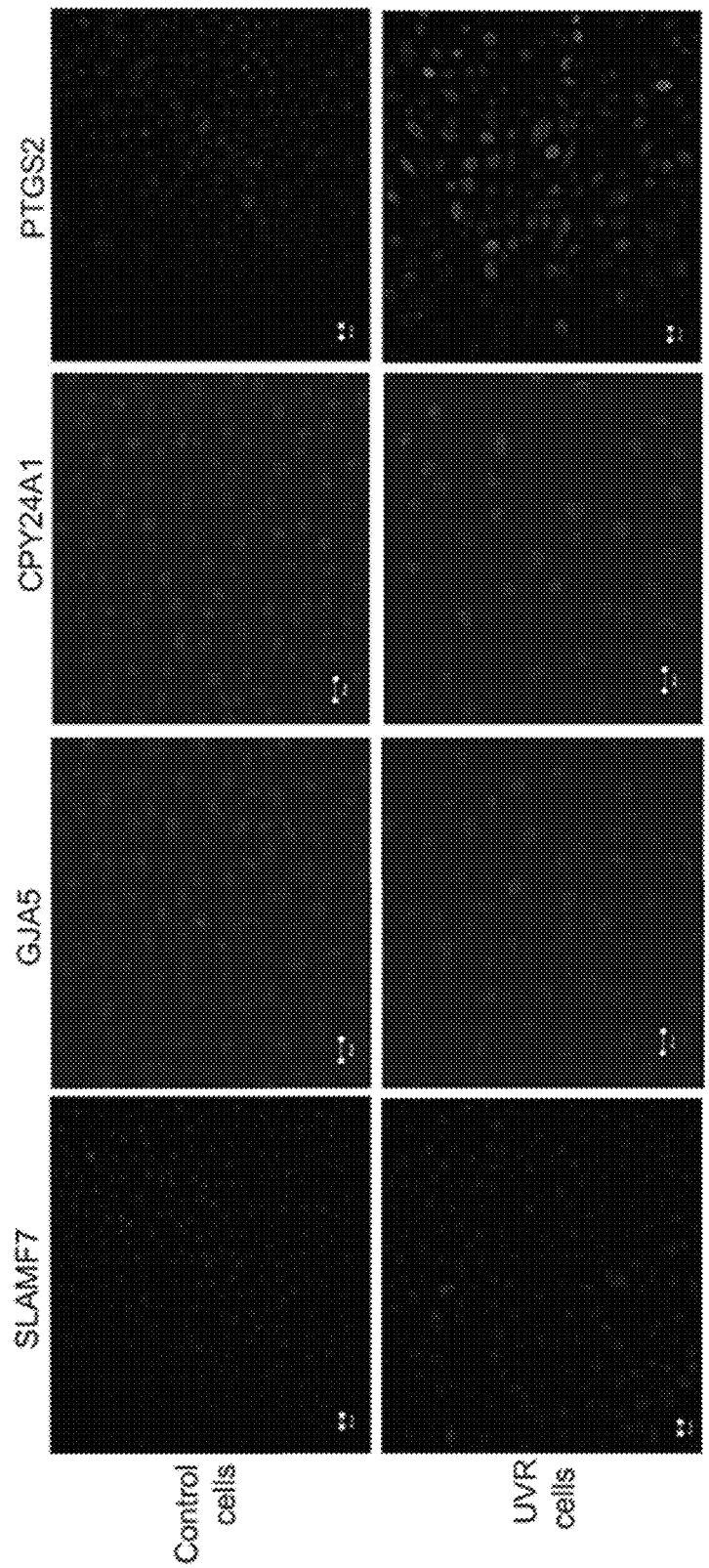
FIG. 10C is the immunofluorescence staining showing protein expression of selected UV target genes in UV-irradiated keratinocytes.
Figure 10D:
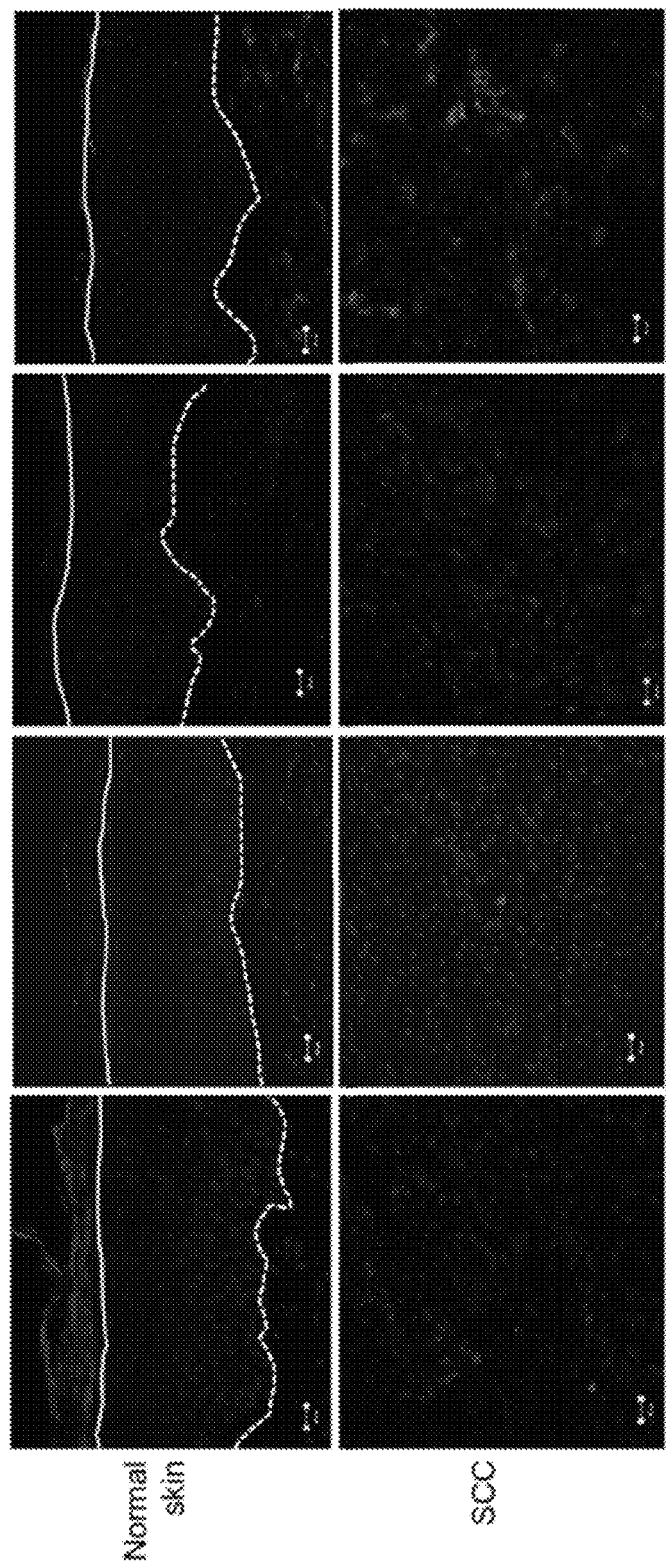
FIG. 10D is the immunofluorescence staining showing protein expression of selected UV target genes in matched human SCC tumors and adjacent normal skin tissues. Blue: DAPI staining. Basement membrane in the normal skin is highlighted by the white dotted line. The stratum corneum is separated by the solid line. Scale bar=20 μm.

Comparison of the UV gene expression signature derived in keratinocytes with the SCC signature revealed numerous UV target genes to be consistently dysregulated in human SCCs. mRNA expression changes of selected UV target genes in SCCs relative to matched normal tissues are shown in FIG. 10A. ChIP-seq profiles at these selected gene loci demonstrated that UV induced pronounced increases in H3K27ac 72 h after UVR (FIG. 10B), consistent with the upregulation of their mRNA expression by UVR. By immunofluorescence staining, we confirmed that protein expression of SLAMF7, GJA5, CYP24A1 and PTGS2 were all elevated in UV-irradiated keratinocytes (FIG. 10C). PTGS2 is a well-characterized UV target gene that is frequently upregulated in skin carcinogenesis. Next, we performed immunofluorescence staining to compare the protein expression of the UV target genes between SCC tumors and normal skins. We found that PTGS2, SLAMF7, and CYP24A1 protein levels were elevated in human SCC tissues, but GJA5 was decreased in SCCs (FIG. 10D). SLAMF7 is an established therapeutic target for multiple myeloma, and a monoclonal antibody (elotuzumab) targeting SLAMF7 can activate natural killer cells to selectively kill myeloma cells. The GJA5 protein is a component of gap junctions. The biological significance of its inverse regulation by UVR and in SCCs awaits further investigations. CYP24A1 mRNA expression is elevated in multiple malignancies. In addition to the UV-induced mutation in CYP24A1 intron, increased H3K27ac may also contribute to its aberrant upregulation in skin SCC.

Discussion

Elucidating the complex molecular mechanisms underlying UV-gene interaction will offer new insights into how UVR modulates skin homeostasis and disease pathogenesis to help improve the prevention of UV-induced skin diseases. Our study represents the first concurrent multi-omics analysis of UV interactions with the genome, epigenome and transcriptome using isogenic cells from the same UV experiment, which minimizes genetic and experimental variations. While our analysis reveals a positive functional correlation between DHA and DGE among a subset of UV target genes, the majority of the UV target genes display discordant changes or, in some cases, inverse correlations between DHA and DGE after UVR, suggesting that H3K27ac alone is insufficient to predict gene expression. UV may cause other epigenetic changes such as DNA methylation and differential histone modifications to dynamically modulate its target gene activity. In this study, we focused on H3K27ac mainly because it is one of the best-characterized epigenetic marks associated with active enhancer and promoter regions. The open chromatin regions marked by H3K27ac may be indicative of frequent binding of transcription factors. The ultimate outcome of gene expression regulation may be co-determined by a combination of other histone modifications including acetylation of H3K9 and H3K18, or methylation of H3K4me1/3, H3K9me3, H3K27me3 that are linked with either active or poised enhancers and promoters. The diverse repertoire of histone modifications together with their interacting regulatory proteins underscore the importance and need of systematic omics-based studies to better understand the mechanisms underpinning UV-gene interactions in skin disease pathogenesis.

UV irradiation is a primary risk factor for both melanoma and non-melanoma skin cancers. Excessive exposure to solar UVR can cause cumulative genetic and epigenetic damages that disrupt gene expression preceding malignant transformation in sun-exposed skin areas. We have validated that some of the novel UV target genes discovered by our RNA-seq studies are dysregulated in human SCCs, which may also have important implications for melanomagenesis. CYP24A1, for example, is an enzyme that can metabolize vitamin D3 to generate biologically active hydroxyderivatives of 20(OH)D3, which possesses efficient anti-tumorigenic activities on melanoma cells. Paradoxically, elevated levels of CYP24A1 have been reported in melanocytic nevi and early stage melanomas, highlighting the complex role of CYP24A1 in skin tumorigenesis. SLAMF7 is a receptor present on immune cells including natural killer (NK) cells that mediates inhibition of NK cells in the absence of EAT-2. Elotuzumab, a monoclonal antibody targeting SLAMF7, has been approved recently as an immunotherapy agent for treating multiple myeloma. SLAMF7 expression is undetectable in normal skin. SLAMF7 mRNA and protein levels are elevated in a subset of human melanoma tissues (data from The Cancer Genome Atlas and The Human Protein Atlas), making SLAMF7 an attractive immunotherapeutic target in for treating SLAMF7-positive melanoma patients. UV-induced epigenetic effects via H3K27ac may persist in UV-irradiated cells and contribute to the malignant transformation of UV-damaged cells over time. While regional gains of H3K27ac occur following UVR, UV induces progressive global losses of H3K27ac that are especially pronounced at 72 h after exposure. The genomewide loss of H3K27ac may be due to suppressed HATs activities, while the regional gain in H3K27ac may occur due to the binding of UV-responsive TFs such as JUN/FOS or TP53 that in turn recruits HATs to their target regions. A survey of mRNA expression of 17 histone acetyltransferases (HATs) and 18 histone deacetylases (HDACs) based on the RNA-seq results reveals an initial downregulation of HAT members (CLOCK, KATE, KAT7 and NCOAs) and HDAC members (HDAC4, HDAC7, HDAC9, SIRT1) at 4 h after UVR (Tables 2 and 3). By 72 h, however, there are no pronounced changes in mRNA levels of either HATs or HDACs except a 2.9-fold increase in SIRT4 (Table 5). SEs are crucial regions of the genome consisting of clusters of enhancer elements that are enriched in H3K27ac and TFs. Despite the dynamic H3K27ac redistribution, the amount of SEs defined by H3K27ac signal peaks following UVR remains relatively stable. Pathway analyses of genes associated with common SEs in control and UV-irradiated keratinocytes reveal a significant enrichment of genes in epidermal development and function. In contrast, genes associated with UV-induced SEs are enriched in pathways of DNA damage response (CDKN1B, TP73, CDC42), consistent with the proposed function of SEs in the regulation of cell identity and state.

Our concurrent omics analyses also show that the mutagenic effect of UV is relatively moderate compared to the extensive epigenomic and transcriptomic changes affecting thousands of genes. While WES is primarily used to identify mutations in coding regions, WES also generates high-quality sequence reads from noncoding regions including introns, UTRs, and intergenic regions. Our study reveals that approximately 13% of UV-induced SNVs are located in exons, whereas the rest are found in introns or intergenic regions. While mutations in protein-coding regions have been the primary focus in disease research, there are growing interests in understanding the role of non-coding mutations after multiple studies demonstrating that the overwhelming majority of mutations, both somatic and germline, occur in non-coding portions of the genome. Our GSEA analysis identifies a significant correlation between UV-induced intron mutations with both DGE and H3K27ac DHA, indicating that intron mutations may interact with the epigenetic machinery in gene regulation. The C to G mutation at the Chr20:52789743 site in the CYP24A1 intron is within a region containing the binding sites of multiple chromatin modifiers such as EZH2, RBBP5, and USF1, highlighting the potential role of this CYP24A1 mutation in its expression regulation. Our WES analysis demonstrates that C>T/G>A are the most common UV-induced SNVs (Table 6), consistent with the UV signature mutation as seen in skin cancers. The percentage of C>T mutations identified in our WES analysis, however, is lower than the percentage observed in skin cancers. The discrepancy may be due to that the mutation profile discovered in our study represents the effect of one single UV exposure event, whereas the mutation profiles in skin tumors reflect long-term cumulative effects of UV exposures. In support of this possibility, the UV-induced mutation profile in our study is highly similar to the one observed in mouse melanomas that are induced by one single neonatal UV exposure.

In summary, our concurrent multi-omics studies provide new insights into the complex molecular mechanisms underlying UV photobiological effects, which have important implications in understanding its impact on skin homeostasis and disease pathogenesis. Our analysis also identified several new UV target genes, including CYP24A1 and SLAMF7, which are aberrantly expressed in human SCCs. The new UV target genes and UV-responsive TFs that we have identified have important clinical implications in skin carcinogenesis, making them attractive targets for developing novel approaches for skin cancer prevention and treatment.

REFERENCES

Afaq, F., Adhami, V. M. & Mukhtar, H. Photochemoprevention of ultraviolet B signaling and photocarcinogenesis. Mutation research 571, 153-173, doi: 10.1016/j.mrfmmm.2004.07.019 (2005).

Anders, S. & Huber, W. Differential expression analysis for sequence count data. Genome biology 11, R106, doi: 10.1186/gb-2010-11-10-r106 (2010).

Anders, S., and Huber, W. (2010) Differential expression analysis for sequence count data. Genome biology 11, R106

Aubin, F. Mechanisms involved in ultraviolet light-induced immunosuppression. European journal of dermatology: EJD 13, 515-523 (2003).

Batagelj, V., and Mrvar, A. (2004) Pajek—Analysis and visualization of large networks. Math Visual, 77-103

Bens, G. (2014) Sunscreens. Advances in experimental medicine and biology 810, 429-463

Besaratinia, A. et al. Wavelength dependence of ultraviolet radiation-induced DNA damage as determined by laser irradiation suggests that cyclobutane pyrimidine dimers are the principal DNA lesions produced by terrestrial sunlight. FASEB journal: official publication of the Federation of American Societies for Experimental Biology 25, 3079-3091, doi: 10.1096/fj.11-187336 (2011).

Boice, J. D., Jr. (2005) Radiation-induced thyroid cancer—what's new? Journal of the National Cancer Institute 97, 703-705

Bonn, S. et al. Tissue-specific analysis of chromatin state identifies temporal signatures of enhancer activity during embryonic development. Nature genetics 44, 148-156, doi: 10.1038/ng.1064 (2012).

Brash, D. E. UV signature mutations. Photochemistry and photobiology 91, 15-26, doi: 10.1111/php.12377 (2015).

Brozyna, A. A. et al. CYP24A1 expression inversely correlates with melanoma progression: clinic-pathological studies. International journal of molecular sciences 15, 19000-19017, doi: 10.3390/ijms151019000 (2014).

Calo, E. & Wysocka, J. Modification of enhancer chromatin: what, how, and why? Molecular cell 49, 825-837, doi: 10.1016/j.molcel.2013.01.038 (2013).

Cowley, G. S. et al. Parallel genome-scale loss of function screens in 216 cancer cell lines for the identification of context-specific genetic dependencies. Scientific data 1, 140035, doi: 10.1038/sdata.2014.35 (2014).

Cowley, G. S., Weir, B. A., Vazquez, F., Tamayo, P., Scott, J. A., Rusin, S., East-Seletsky, A., Ali, L. D., Gerath, W. F., Pantel, S. E., Lizotte, P. H., Jiang, G., Hsiao, J., Tsherniak, A., Dwinell, E., Aoyama, S., Okamoto, M., Harrington, W., Gelfand, E., Green, T. M., Tomko, M. J., Gopal, S., Wong, T. C., Li, H., Howell, S., Stransky, N., Liefeld, T., Jang, D., Bistline, J., Hill Meyers, B., Armstrong, S. A., Anderson, K. C., Stegmaier, K., Reich, M., Pellman, D., Boehm, J. S., Mesirov, J. P., Golub, T. R., Root, D. E., and Hahn, W. C. (2014) Parallel genome-scale loss of function screens in 216 cancer cell lines for the identification of context-specific genetic dependencies. Scientific data 1, 140035

Creyghton, M. P. et al. Histone H3K27ac separates active from poised enhancers and predicts developmental state. Proceedings of the National Academy of Sciences of the United States of America 107, 21931-21936, doi: 10.1073/pnas.1016071107 (2010).

Dawes, J. M. et al. Genome-wide transcriptional profiling of skin and dorsal root ganglia after ultraviolet-B-induced inflammation. PLoS one 9, e93338, doi: 10.1371/journal.pone.0093338 (2014).

Dawes, J. M., Antunes-Martins, A., Perkins, J. R., Paterson, K. J., Sisignano, M., Schmid, R., Rust, W., Hildebrandt, T., Geisslinger, G., Orengo, C., Bennett, D. L., and McMahon, S. B. (2014) Genome-wide transcriptional profiling of skin and dorsal root ganglia after ultraviolet-B-induced inflammation. PLoS one 9, e93338

Dazard, J. E., Gal, H., Amariglio, N., Rechavi, G., Domany, E., and Givol, D. (2003) Genome-wide comparison of human keratinocyte and squamous cell carcinoma responses to UVB irradiation: implications for skin and epithelial cancer. Oncogene 22, 2993-3006 de la Fuente, H., Lamana, A., Mittelbrunn, M., Perez-Gala, S., Gonzalez, S., Garcia-Diez, A., Vega, M., and Sanchez-Madrid, F. (2009) Identification of genes responsive to solar simulated UV radiation in human monocyte-derived dendritic cells. PLoS one 4, e6735

Dennis, L. K., Beane Freeman, L. E., and VanBeek, M. J. (2003) Sunscreen use and the risk for melanoma: a quantitative review. Annals of internal medicine 139, 966-978

Djebali, S. et al. Landscape of transcription in human cells. Nature 489, 101-108, doi: 10.1038/nature11233 (2012).

Elbediwy, A. et al. Integrin signalling regulates YAP and TAZ to control skin homeostasis. Development 143, 1674-1687, doi: 10.1242/dev.133728 (2016).

Ernst, J. et al. Mapping and analysis of chromatin state dynamics in nine human cell types. Nature 473, 43-49, doi: 10.1038/nature09906 (2011).

Fartasch, M., Diepgen, T. L., Schmitt, J., and Drexler, H. (2012) The Relationship Between Occupational Sun Exposure and Non-Melanoma Skin Cancer. Dtsch Arztebl Int 109, 715-U714

Gronniger, E. et al. Aging and chronic sun exposure cause distinct epigenetic changes in human skin. PLoS genetics 6, e1000971, doi: 10.1371/journal.pgen.1000971 (2010).

Guo, Y. et al. Exome sequencing generates high quality data in non-target regions. BMC genomics 13, 194, doi: 10.1186/1471-2164-13-194 (2012).

Guy, G. P., Jr., Mechlin, S. R., Ekwueme, D. U., and Yabroff, K. R. (2015) Prevalence and costs of skin cancer treatment in the U.S., 2002-2006 and 2007-2011. American journal of preventive medicine 48, 183-187

Gyorffy, B., Hatzis, C., Sanft, T., Hofstatter, E., Aktas, B., and Pusztai, L. (2015) Multigene prognostic tests in breast cancer: past, present, future. Breast cancer research: BCR 17, 11

Hacker, E., Boyce, Z., Kimlin, M. G., Wockner, L., Pollak, T., Vaartjes, S. A., Hayward, N. K., and Whiteman, D. C. (2013) The effect of MC1R variants and sunscreen on the response of human melanocytes in vivo to ultraviolet radiation and implications for melanoma. Pigment cell & melanoma research 26, 835-844

Heckman, C. J., Chandler, R., Kloss, J. D., Benson, A., Rooney, D., Munshi, T., Darlow, S. D., Perlis, C., Manne, S. L., and Oslin, D. W. (2013) Minimal Erythema Dose (MED) testing. Journal of visualized experiments: JoVE, e50175

Heintzman, N. D. et al. Distinct and predictive chromatin signatures of transcriptional promoters and enhancers in the human genome. Nature genetics 39, 311-318, doi: 10.1038/ng1966 (2007).

Hnisz, D. et al. Super-enhancers in the control of cell identity and disease. Cell 155, 934-947, doi: 10.1016/j.cell.2013.09.053 (2013).

Hobaus, J. et al. Impact of CYP24A1 overexpression on growth of colorectal tumour xenografts in mice fed with vitamin D and soy. International journal of cancer. Journal international du cancer 138, 440-450, doi: 10.1002/ijc.29717 (2016).

Hubers, A. J. et al. DNA hypermethylation analysis in sputum for the diagnosis of lung cancer: training validation set approach. British journal of cancer 112, 1105-1113, doi: 10.1038/bjc.2014.636 (2015).

Hudson, L. G., Gale, J. M., Padilla, R. S., Pickett, G., Alexander, B. E., Wang, J., and Kusewitt, D. F. (2010) Microarray analysis of cutaneous squamous cell carcinomas reveals enhanced expression of epidermal differentiation complex genes. Molecular carcinogenesis 49, 619-

629 Kadekaro, A. L. et al. Melanocortin 1 receptor genotype: an important determinant of the damage response of melanocytes to ultraviolet radiation. FASEB journal: official publication of the Federation of American Societies for Experimental Biology 24, 3850-3860, doi: 10.1096/fj.10-158485 (2010).

Khurana, E. et al. Role of non-coding sequence variants in cancer. Nature reviews. Genetics 17, 93-108, doi: 10.1038/nrg.2015.17 (2016).

Konger, R. L., Martel, K. C., Jernigan, D., Zhang, Q. & Travers, J. B. The peroxisome proliferator-activated receptor gamma system regulates ultraviolet B-induced prostaglandin e(2) production in human epidermal keratinocytes. PPAR research 2010, 467053, doi: 10.1155/2010/467053 (2010).

Lahtz, C. et al. UVB irradiation does not directly induce detectable changes of DNA methylation in human keratinocytes. F1000Research 2, 45, doi: 10.12688/f1000re5earch.2-45.v1 (2013).

Lautenschlager, S., Wulf, H. C., and Pittelkow, M. R. (2007) Photoprotection. Lancet 370, 528-537

Lin, S. W., Wheeler, D. C., Park, Y., Cahoon, E. K., Hollenbeck, A. R., Freedman, D. M., and Abnet, C. C. (2012) Prospective study of ultraviolet radiation exposure and risk of cancer in the United States. International journal of cancer. Journal international du cancer 131, E1015-1023

Liu, L. et al. Hairless is a histone H3K9 demethylase. FASEB journal: offcial publication of the Federation of American Societies for Experimental Biology 28, 1534-1542, doi: 10.1096/fj.13-237677 (2014).

Loven, J. et al. Selective inhibition of tumor oncogenes by disruption of super-enhancers. Cell 153, 320-334, doi: 10.1016/j.cell.2013.03.036 (2013).

Mao, P., Smerdon, M. J., Roberts, S. A. & Wyrick, J. J. Chromosomal landscape of UV damage formation and repair at single nucleotide resolution. Proceedings of the National Academy of Sciences of the United States of America 113, 9057-9062, doi: 10.1073/pnas.1606667113 (2016).

Mukhopadhyay, P., Ferguson, B., Muller, H. K., Handoko, H. Y. & Walker, G. J. Murine melanomas accelerated by a single UVR exposure carry photoproduct footprints but lack UV signature C>T mutations in critical genes. Oncogene 35, 3342-3350, doi: 10.1038/onc.2015.386 (2016).

Niederriter, A. R., Varshney, A., Parker, S. C. & Martin, D. M. Super Enhancers in Cancers, Complex Disease, and Developmental Disorders. Genes 6, 1183-1200, doi: 10.3390/genes6041183 (2015).

Osterwalder, U., and Herzog, B. (2009) Sun protection factors: world wide confusion. The British journal of dermatology 161 Suppl 3, 13-24

Palumbo, A. & Sonneveld, P. Preclinical and clinical evaluation of elotuzumab, a SLAMF7-targeted humanized monoclonal antibody in development for multiple myeloma. Expert review of hematology 8, 481-491, doi: 10.1586/17474086.2015.1053866 (2015).

Pentland, A. P., Schoggins, J. W., Scott, G. A., Khan, K. N. & Han, R. Reduction of UV-induced skin tumors in hairless mice by selective COX-2 inhibition. Carcinogenesis 20, 1939-1944 (1999).

Perera, D. et al. Differential DNA repair underlies mutation hotspots at active promoters in cancer genomes. Nature 532, 259-263, doi: 10.1038/nature17437 (2016).

Pfeifer, G. P., You, Y. H. & Besaratinia, A. Mutations induced by ultraviolet light. Mutation research 571, 19-31, doi: 10.1016/j.mrfmmm.2004.06.057 (2005).

Pickering, C. R. et al. Mutational landscape of aggressive cutaneous squamous cell carcinoma. Clinical cancer research: an official journal of the American Association for Cancer Research 20, 6582-6592, doi: 10.1158/1078-0432.CCR-14-1768 (2014).

Pleasance, E. D., Cheetham, R. K., Stephens, P. J., McBride, D. J., Humphrey, S. J., Greenman, C. D., Varela, I., Lin, M. L., Ordonez, G. R., Bignell, G. R., Ye, K., Alipaz, J., Bauer, M. J., Beare, D., Butler, A., Carter, R. J., Chen, L., Cox, A. J., Edkins, S., Kokko-Gonzales, P. I., Gormley, N. A., Grocock, R. J., Haudenschild, C. D., Hims, M. M., James, T., Jia, M., Kingsbury, Z., Leroy, C., Marshall, J., Menzies, A., Mudie, L. J., Ning, Z., Royce, T., Schulz-Trieglaff, O. B., Spiridou, A., Stebbings, L. A., Szajkowski, L., Teague, J., Williamson, D., Chin, L., Ross, M. T., Campbell, P. J., Bentley, D. R., Futreal, P. A., and Stratton, M. R. (2010) A comprehensive catalogue of somatic mutations from a human cancer genome. Nature 463, 191-196

Rada-Iglesias, A. et al. A unique chromatin signature uncovers early developmental enhancers in humans. Nature 470, 279-283, doi:10.1038/nature09692 (2011).

Rieger, K. E., and Chu, G. (2004) Portrait of transcriptional responses to ultraviolet and ionizing radiation in human cells. Nucleic acids research 32, 4786-4803

Rippa, A. L., Vorotelyak, E. A., Vasiliev, A. V. & Terskikh, V. V. The role of integrins in the development and homeostasis of the epidermis and skin appendages. Acta naturae 5, 22-33 (2013).

Robinson, J. K. (2005) Sun exposure, sun protection, and vitamin D. Jama 294, 1541-1543

Rogers, H. W., Weinstock, M. A., Feldman, S. R. & Coldiron, B. M. Incidence Estimate of Nonmelanoma Skin Cancer (Keratinocyte Carcinomas) in the U.S. Population, 2012. JAMA dermatology 151, 1081-1086, doi: 10.1001/jamadermatol.2015.1187 (2015).

Rogers, H. W., Weinstock, M. A., Feldman, S. R., and Coldiron, B. M. (2015) Incidence Estimate of Nonmelanoma Skin Cancer (Keratinocyte Carcinomas) in the US Population, 2012. JAMA dermatology 151, 1081-1086

Schick, S. et al. Dynamics of chromatin accessibility and epigenetic state in response to UV damage. Journal of cell science 128, 4380-4394, doi: 10.1242/jcs.173633 (2015).

Schutze, D. M. et al. Longitudinal assessment of DNA methylation changes during HPVE6E7-induced immortalization of primary keratinocytes. Epigenetics 10, 73-81, doi: doi: 10.4161/15592294.2014.990787 (2015).

Seite, S., Fourtanier, A., Moyal, D., and Young, A. R. (2010) Photodamage to human skin by suberythemal exposure to solar ultraviolet radiation can be attenuated by sunscreens: a review. The British journal of dermatology 163, 903-914

Shain, A. H. et al. The Genetic Evolution of Melanoma from Precursor Lesions. The New England journal of medicine 373, 1926-1936, doi: 10.1056/NEJMoa1502583 (2015).

Shen, Y., Kim, A. L., Du, R. & Liu, L. Transcriptome Analysis Identifies the Dysregulation of Ultraviolet Target Genes in Human Skin Cancers. PloS one 11, e0163054, doi: 10.1371/journal.pone.0163054 (2016).

Skobowiat, C. & Slominski, A. T. UVB Activates Hypothalamic-Pituitary-Adrenal Axis in C57BL/6 Mice. The Journal of investigative dermatology 135, 1638-1648, doi: 10.1038/jid.2014.450 (2015).

Slominski, A. et al. Steroidogenesis in the skin: implications for local immune functions. The Journal of steroid biochemistry and molecular biology 137, 107-123, doi: 10.1016/j.jsbmb.2013.02.006 (2013).

Slominski, A. T. et al. Key role of CRF in the skin stress response system. Endocrine reviews 34, 827-884, doi: 10.1210/er.2012-1092 (2013).

Slominski, A. T. et al. Local melatoninergic system as the protector of skin integrity. International journal of molecular sciences 15, 17705-17732, doi: 10.3390/ijms151017705 (2014).

Slominski, A. T. et al. Novel non-calcemic secosteroids that are produced by human epidermal keratinocytes protect against solar radiation. The Journal of steroid biochemistry and molecular biology 148, 52-63, doi: 10.1016/j.jsbmb.2015.01.014 (2015).

Slominski, A. T. et al. Sensing the environment: regulation of local and global homeostasis by the skin's neuroendocrine system. Advances in anatomy, embryology, and cell biology 212, v, vii, 1-115 (2012).

Slominski, A., Tobin, D. J., Shibahara, S. & Wortsman, J. Melanin pigmentation in mammalian skin and its hormonal regulation. Physiological reviews 84, 1155-1228, doi: 10.1152/physrev.00044.2003 (2004).

Stern, R. S. Prevalence of a history of skin cancer in 2007: results of an incidence-based model. Archives of dermatology 146, 279-282, doi: 10.1001/archdermatol.2010.4 (2010).

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005) Gene set enrichment analysis: a knowledge-based approach for interpreting genome-wide expression profiles. Proceedings of the National Academy of Sciences of the United States of America 102, 15545-15550

Sun, X., Kim, A., Nakatani, M., Shen, Y. & Liu, L. Distinctive molecular responses to ultraviolet radiation between keratinocytes and melanocytes. Experimental dermatology, doi: 10.1111/exd.13057 (2016).

Szklarczyk, D., Franceschini, A., Wyder, S., Forslund, K., Heller, D., Huerta-Cepas, J., Simonovic, M., Roth, A., Santos, A., Tsafou, K. P., Kuhn, M., Bork, P., Jensen, L. J., and von Mering, C. (2015) STRING v10: protein-protein interaction networks, integrated over the tree of life. Nucleic acids research 43, D447-452

Takao, J., Ariizumi, K., Dougherty, 11, and Cruz, P. D., Jr. (2002) Genomic scale analysis of the human keratinocyte response to broad-band ultraviolet-B irradiation. Photodermatology, photoimmunology & photomedicine 18, 5-13

Tannour-Louet, M. et al. Increased expression of CYP24A1 correlates with advanced stages of prostate cancer and can cause resistance to vitamin D3-based therapies. FASEB journal: offcial publication of the Federation of American Societies for Experimental Biology 28, 364-372, doi: 10.1096/fj.13-236109 (2014).

The Surgeon General's Call to Action to Prevent Skin Cancer, Washington (DC) (2014)

Thurman, R. E. et al. The accessible chromatin landscape of the human genome. Nature 489, 75-82, doi: 10.1038/nature11232 (2012).

Tieu, E. W. et al. Rat CYP24A1 acts on 20-hydroxyvitamin D(3) producing hydroxylated products with increased biological activity. Biochemical pharmacology 84, 1696-1704, doi: 10.1016/j.bcp.2012.09.032 (2012).

van Eck, N. J., Waltman, L., Dekker, R., and van den Berg, J. (2010) A Comparison of Two Techniques for Bibliometric Mapping: Multidimensional Scaling and VOS. J Am Soc Inf Sci Tec 61, 2405-2416

Vandiver, A. R. et al. Age and sun exposure-related widespread genomic blocks of hypomethylation in nonmalignant skin. Genome biology 16, 80, doi: 10.1186/s13059-015-0644-y (2015).

Wang, Y. et al. A complex network of factors with overlapping affnities represses splicing through intronic elements. Nature structural & molecular biology 20, 36-45, doi: 10.1038/nsmb.2459 (2013).

Warr, A. et al. Exome Sequencing: Current and Future Perspectives. G3 5, 1543-1550, doi: 10.1534/g3.115.018564 (2015).

Wei, Y. et al. SEA: a super-enhancer archive. Nucleic acids research 44, D172-179, doi: 10.1093/nar/gkv1243 (2016).

Whyte, W. A. et al. Master transcription factors and mediator establish super-enhancers at key cell identity genes. Cell 153, 307-319, doi: 10.1016/j.cell.2013.03.035 (2013).

Wu, S. et al. History of Severe Sunburn and Risk of Skin Cancer Among Women and Men in 2 Prospective Cohort Studies. American journal of epidemiology 183, 824-833, doi: 10.1093/aje/kwv282 (2016).

Wu, S., Han, J., Laden, F., and Qureshi, A. A. (2014) Long-term ultraviolet flux, other potential risk factors, and skin cancer risk: a cohort study. Cancer epidemiology, biomarkers & prevention: a publication of the American Association for Cancer Research, cosponsored by the American Society of Preventive Oncology 23, 1080-1089

Yang, G., Zhang, G., Pittelkow, M. R., Ramoni, M. & Tsao, H. Expression profiling of UVB response in melanocytes identifies a set of p53-target genes. The Journal of investigative dermatology 126, 2490-2506, doi: 10.1038/sj.jid.5700470 (2006).

Yang, G., Zhang, G., Pittelkow, M. R., Ramoni, M., and Tsao, H. (2006) Expression profiling of UVB response in melanocytes identifies a set of p53-target genes. The Journal of investigative dermatology 126, 2490-2506

You, Y. N., Rustin, R. B., and Sullivan, J. D. (2015) Oncotype DX((R)) colon cancer assay for prediction of recurrence risk in patients with stage II and III colon cancer: A review of the evidence. Surgical oncology 24, 61-66

Zanotti, L., Bottini, A., Rossi, C., Generali, D., and Cappelletti, M. R. (2014) Diagnostic tests based on gene expression profile in breast cancer: from background to clinical use. Tumour biology: the journal of the International Society for Oncodevelopmental Biology and Medicine 35, 8461-8470

Zentner, G. E., Tesar, P. J. & Scacheri, P. C. Epigenetic signatures distinguish multiple classes of enhancers with distinct cellular functions. Genome research 21, 1273-1283, doi: 10.1101/gr.122382.111 (2011).

Zhang, X. et al. Solar Simulated Ultraviolet Radiation Induces Global Histone Hypoacetylation in Human Keratinocytes. PloS one 11, e0150175, doi: 10.1371/journal.pone.0150175 (2016).

The invention claimed is:

1. A method for diagnosing and treating ultraviolet radiation (UVR)-induced skin damage in a subject comprising: analyzing a skin sample from the subject for mRNA expression levels of DPP4, CLDN4, CLDN7 and DEFB1; diagnosing the subject as having UVR-induced skin damage if the mRNA expression levels of DPP4, CLDN4, CLDN7 and DEFB1 in the skin sample are increased compared to mRNA expression levels of DPP4, CLDN4, CLDN7 and DEFB1 in a normal, control skin sample; and administering a treatment for UVR-induced skin damage to the diagnosed subject.

2. The method according to claim 1, wherein the subject is a mammal.

3. The method according to claim 1, wherein the subject is a human.

4. The method according to claim 1, wherein the UVR-induced skin damage is selected from photocarcinogenesis, photoaging, immunosuppression, and oxidative stress.

5. The method according to claim 1, wherein the skin sample comprises a skin equivalent or a human or non-human cultured cell selected from a keratinocyte, a melanocyte, a dermal fibroblast, a mast cell, an endothelial cell, a sebocyte, a hair papilla, and a matrix cell.

6. The method according to claim 1, wherein the skin sample comprises human keratinocytes.

7. The method according to claim 1, wherein the method further comprises analyzing the skin sample from the subject for the mRNA expression level of a gene selected from the group consisting of: IL-6, PTGS2, IL1B, CDKN1A, BCL2L1, ICAM1, HMOX1, VAV1, PLA2G16, MMP1, HIST1H4H, CYP4F3, and CD8A.

8. The method according to claim 1, wherein the method further comprises analyzing the skin sample from the subject for the mRNA expression level of a gene selected from the group consisting of: SLPI, KLK7, KRT13, NHLH2, GPRCSA, HIST1H2BK, IGFBP3, SPOCD1, IF127, KLK11, and TNFSF4.

* * * * *